United States Patent
Sapargaliyev et al.

(10) Patent No.: US 8,598,516 B2
(45) Date of Patent: Dec. 3, 2013

(54) METHOD OF MASS-SPECTROMETRY AND A DEVICE FOR ITS REALIZATION

(71) Applicants: Yerbol Aldanovich Sapargaliyev, Almaty (KZ); Aldan Asanovich Sapargaliyev, Almaty (KZ)

(72) Inventors: Yerbol Aldanovich Sapargaliyev, Almaty (KZ); Aldan Asanovich Sapargaliyev, Almaty (KZ)

(*) Notice: Subject to any disclaimer, the term of this patent is extended or adjusted under 35 U.S.C. 154(b) by 0 days.

(21) Appl. No.: 13/737,018

(22) Filed: Jan. 9, 2013

(65) Prior Publication Data

US 2013/0161508 A1    Jun. 27, 2013

(30) Foreign Application Priority Data

Jul. 9, 2010 (KZ) .................................. 2010/0907
Jul. 8, 2011 (WO) ................ PCT/KZ2011/000011

(51) Int. Cl.
*B01D 59/44*    (2006.01)

(52) U.S. Cl.
USPC .......... 250/282; 250/281; 250/283; 250/286; 250/287; 250/288; 250/290; 250/291; 250/292; 250/293; 250/294; 250/295; 250/296; 250/297

(58) Field of Classification Search
USPC .................. 250/281–283, 286–288, 290–297
See application file for complete search history.

(56) References Cited

U.S. PATENT DOCUMENTS

| | | | | |
|---|---|---|---|---|
| 4,694,168 | A * | 9/1987 | Le Beyec et al. | 250/287 |
| 7,385,187 | B2 * | 6/2008 | Verentchikov et al. | 250/287 |
| 2008/0272287 | A1 * | 11/2008 | Vestal | 250/282 |
| 2009/0166528 | A1 * | 7/2009 | Makarov | 250/282 |
| 2011/0186729 | A1 * | 8/2011 | Verentchikov et al. | 250/282 |

* cited by examiner

*Primary Examiner* — Jack Berman
*Assistant Examiner* — Meenakshi Sahu
(74) *Attorney, Agent, or Firm* — Michael J. Feigin, Esq.; Feigin & Associates, LLC

(57) ABSTRACT

The present invention relates to the analytical electronics used to identify compositions and structures of substances, in particular, to the analyzers comprising at least one mass-spectrometer (MS) and may be applied in such fields as medicine, biology, gas and oil industry, metallurgy, energy, geochemistry, hydrology, ecology.

Technical result provides the increase in MS resolution, gain in sensitivity, precision and measurement rates of substances compositions and structures concurrently with enhancement of analyzer functional capabilities, downsizing and mass reduction.

In claimed invention the ion flux generation and its guiding are performed in off-axis single-flow mode; parallel multi-stage mode; through use of three-dimensional field with mean meridian surface including without limitation three-dimensional reflecting and dual-zoned reflecting modes or by method of multi-reflection arrays.

Devices to implement the claimed method are embodied.

Proposed schematic ion optical diagrams allow developing different MS types notable for their minimized material intensity and geometrical dimensions.

220 Claims, 36 Drawing Sheets

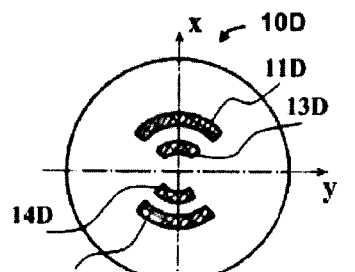
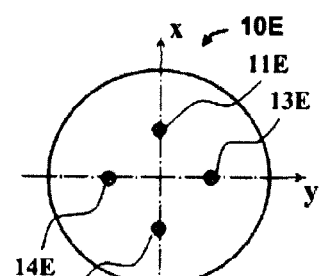
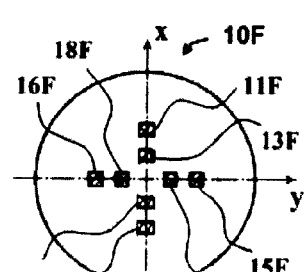
FIG. 8   FIG. 9   FIG. 10
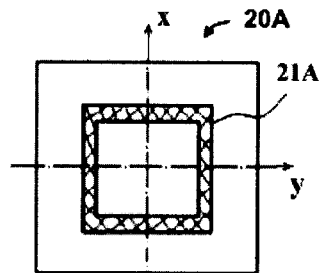
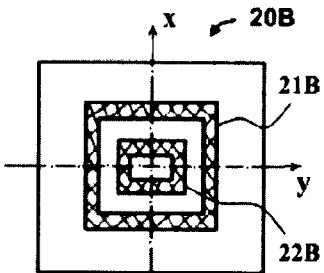
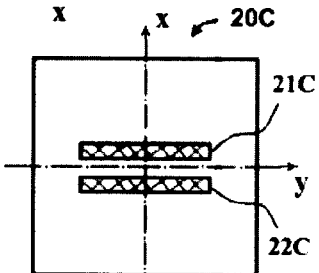
FIG. 11   FIG. 12   FIG. 13
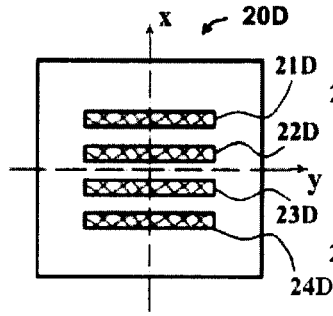
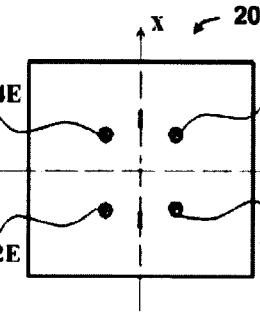
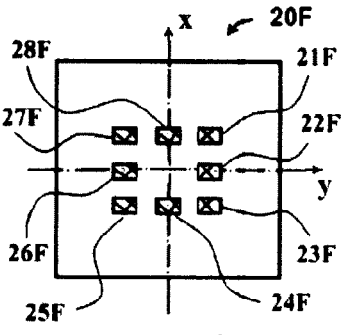
FIG. 14   FIG. 15   FIG. 16
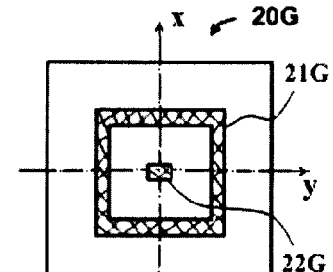
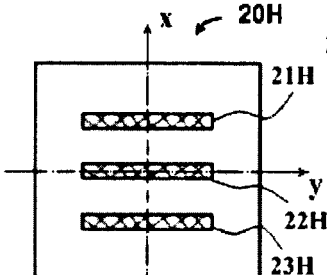
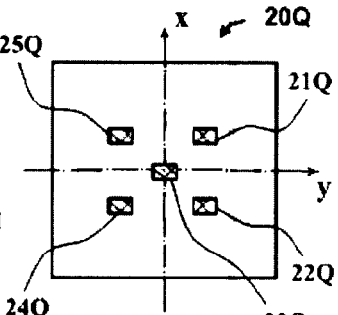
FIG. 17   FIG. 18   FIG. 19

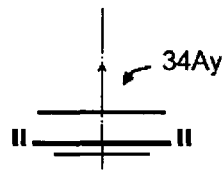 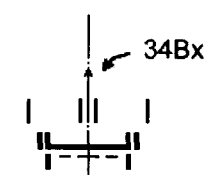 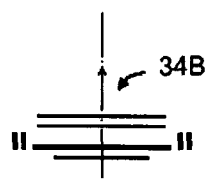 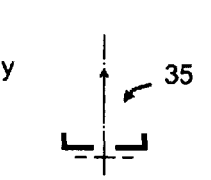 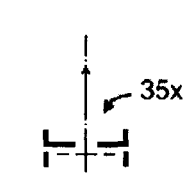
FIG. 48　　FIG. 49　　FIG. 50　　FIG. 51　　FIG. 52
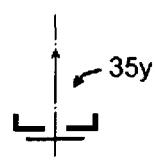 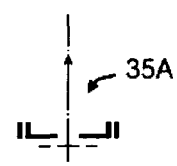 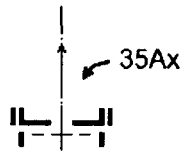 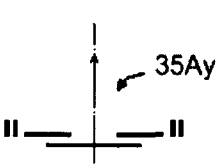 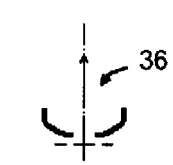
FIG. 53　　FIG. 54　　FIG. 55　　FIG. 56　　FIG. 57
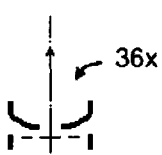 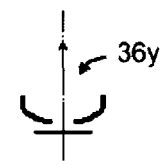 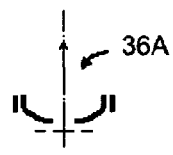 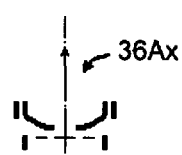 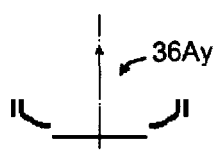
FIG. 58　　FIG. 59　　FIG. 60　　FIG. 61　　FIG. 62
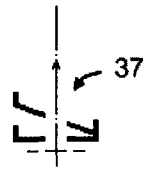 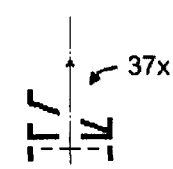 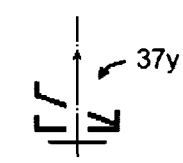 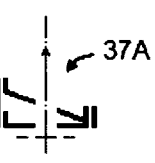 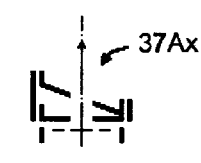
FIG. 63　　FIG. 64　　FIG. 65　　FIG. 66　　FIG. 67
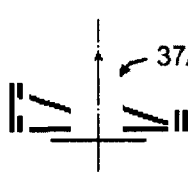 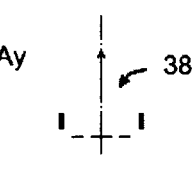 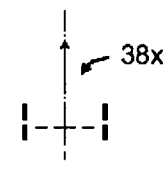 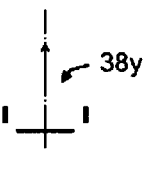 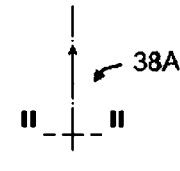
FIG. 68　　FIG. 69　　FIG. 70　　FIG. 71　　FIG. 72

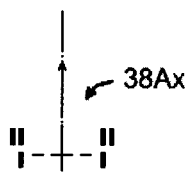 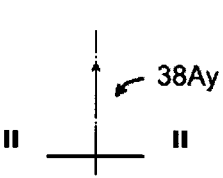 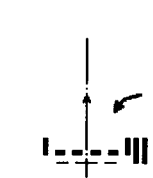 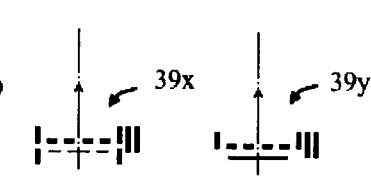
FIG. 73    FIG. 74    FIG. 75    FIG. 76    FIG. 77
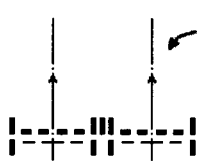 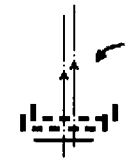  
FIG. 78    FIG. 79    FIG. 80    FIG. 81
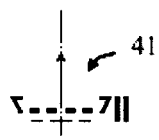 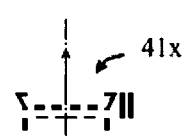  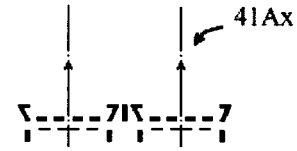
FIG. 82    FIG. 83    FIG. 84    FIG. 85
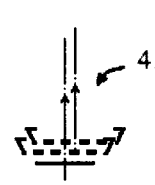 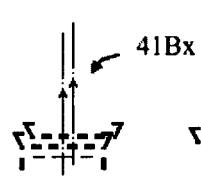 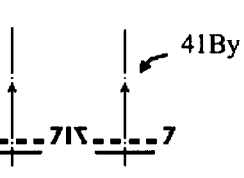 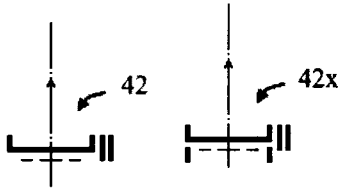
FIG. 86    FIG. 87    FIG. 88    FIG. 89    FIG. 90
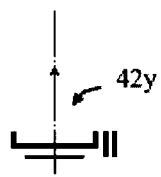 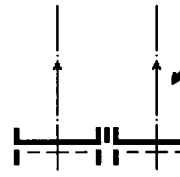 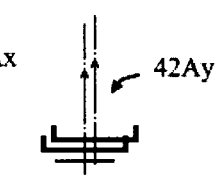 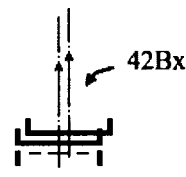
FIG. 91    FIG. 92    FIG. 93    FIG. 94

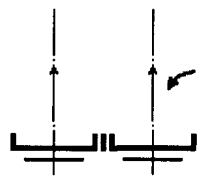 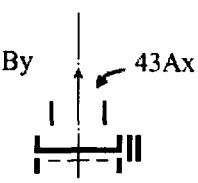 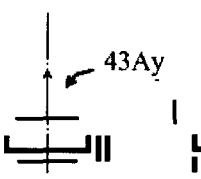 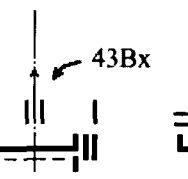 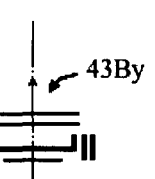
FIG. 95   FIG. 96   FIG. 97   FIG. 98   FIG. 99
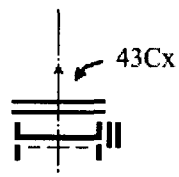 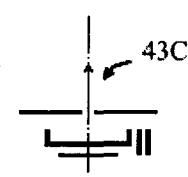 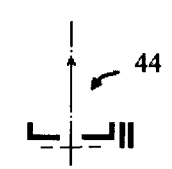 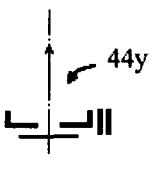
FIG. 100   FIG. 101   FIG. 102   FIG. 103   FIG. 104
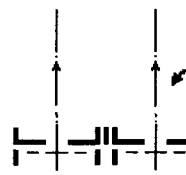 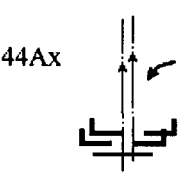 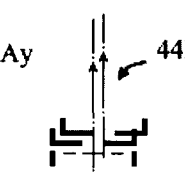 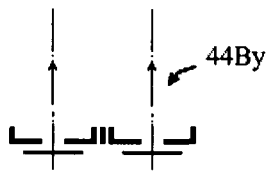
FIG. 105   FIG. 106   FIG. 107   FIG. 108
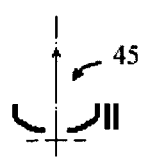 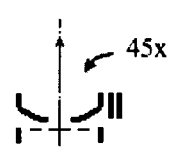 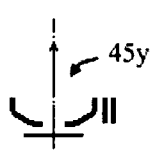 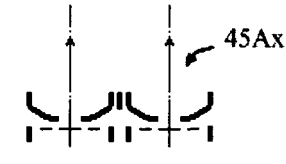
FIG. 109   FIG. 110   FIG. 111   FIG. 112
 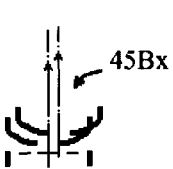 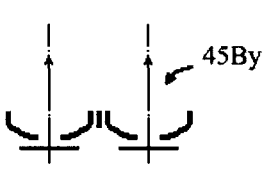 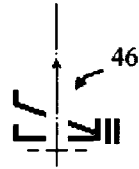
FIG. 113   FIG. 114   FIG. 115   FIG. 116

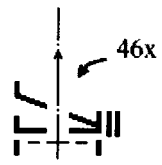
FIG. 117
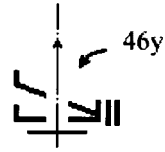
FIG. 118
FIG. 119
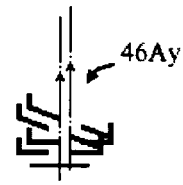
FIG. 120
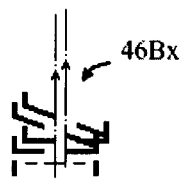
FIG. 121
FIG. 122
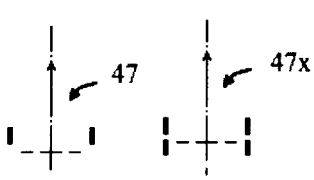
FIG. 123  FIG. 124  FIG. 125
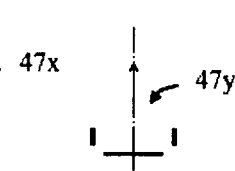
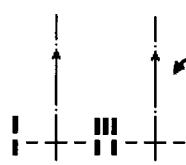
FIG. 126
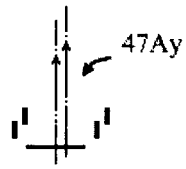
FIG. 127
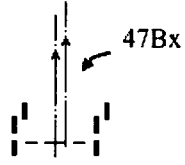
FIG. 128
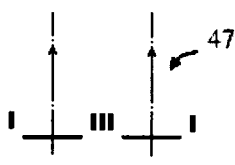
FIG. 129
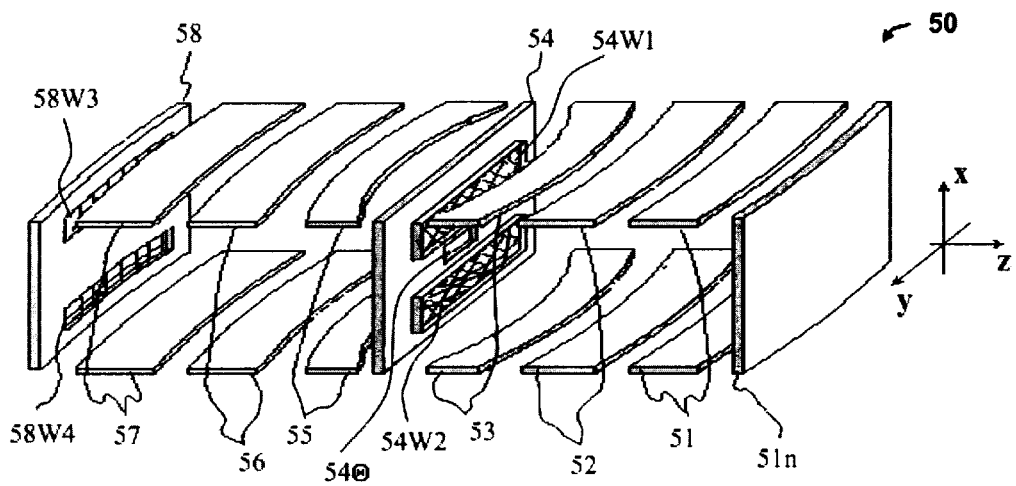
FIG. 130

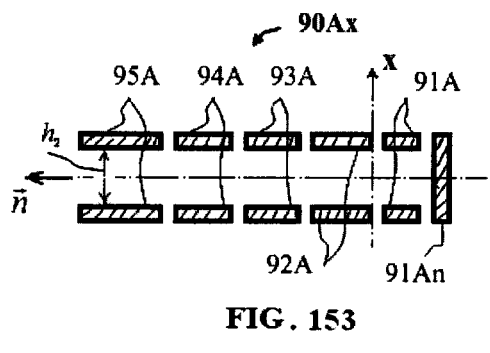
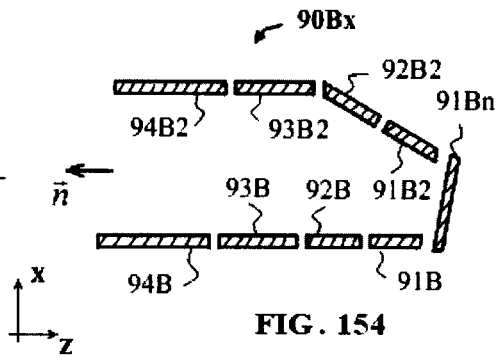
FIG. 153    FIG. 154
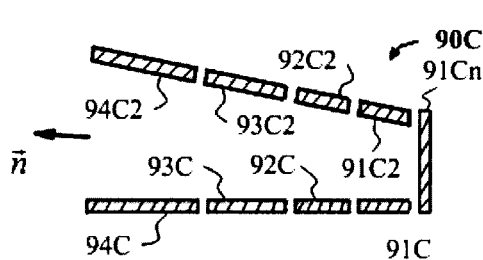
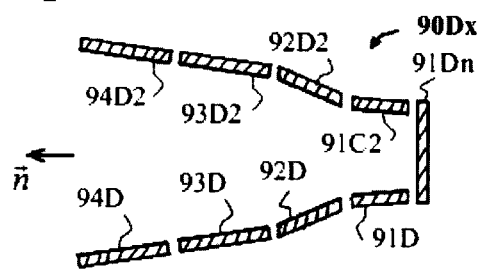
FIG. 155    FIG. 156
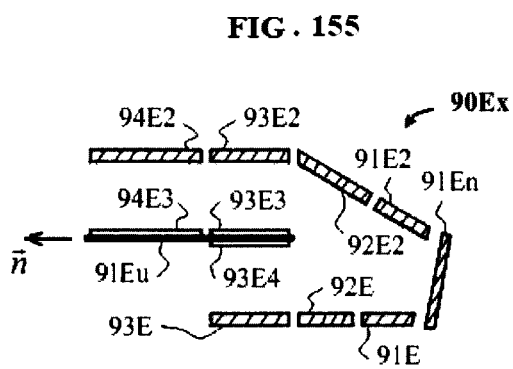
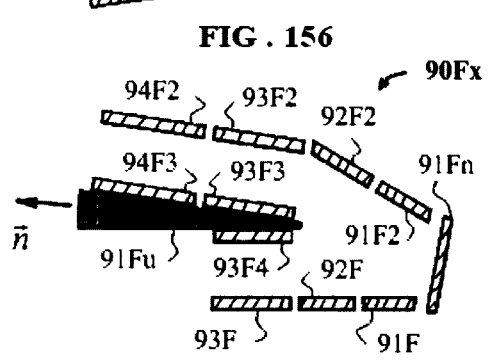
FIG. 157    FIG. 158
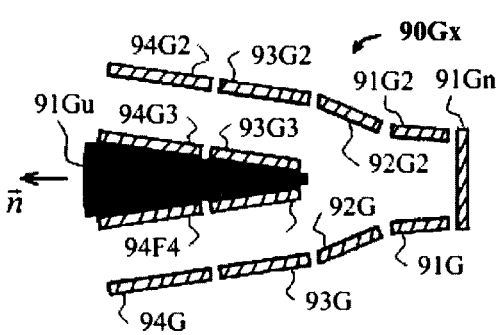
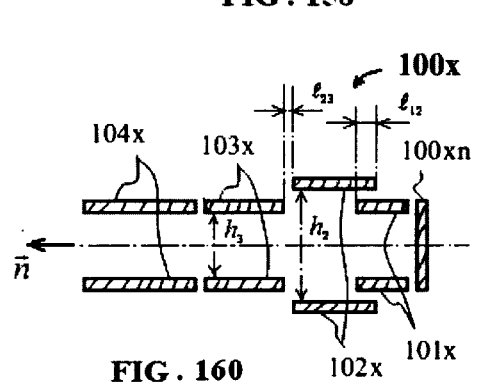
FIG. 159    FIG. 160

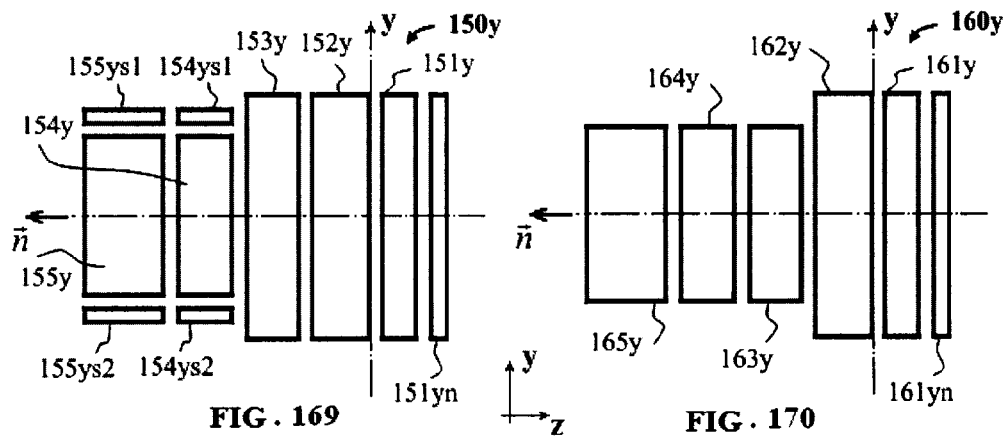
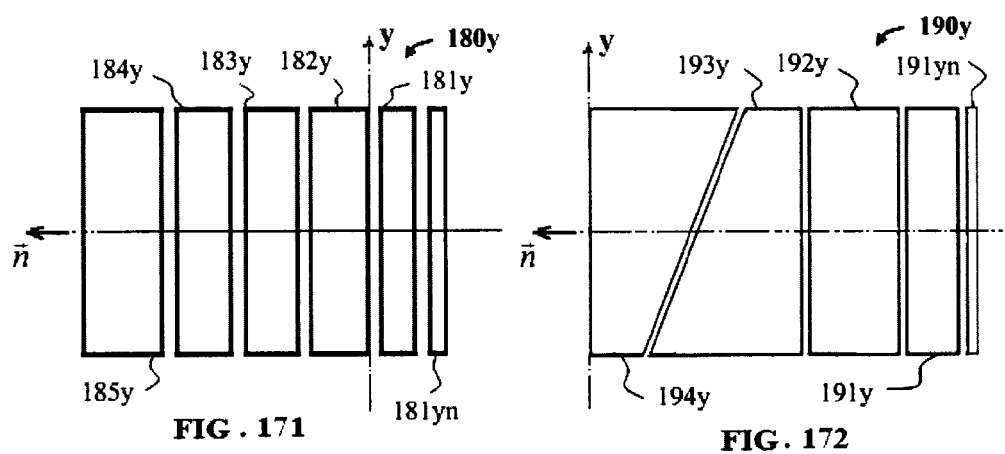
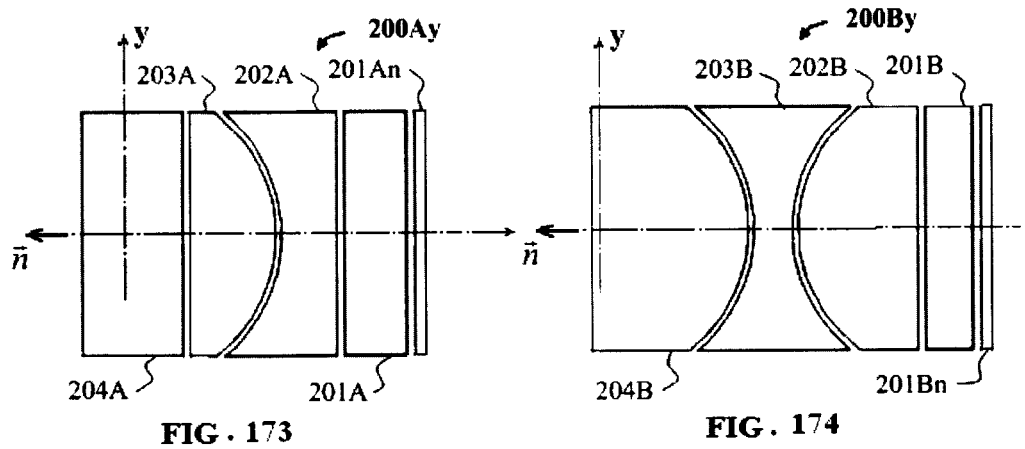

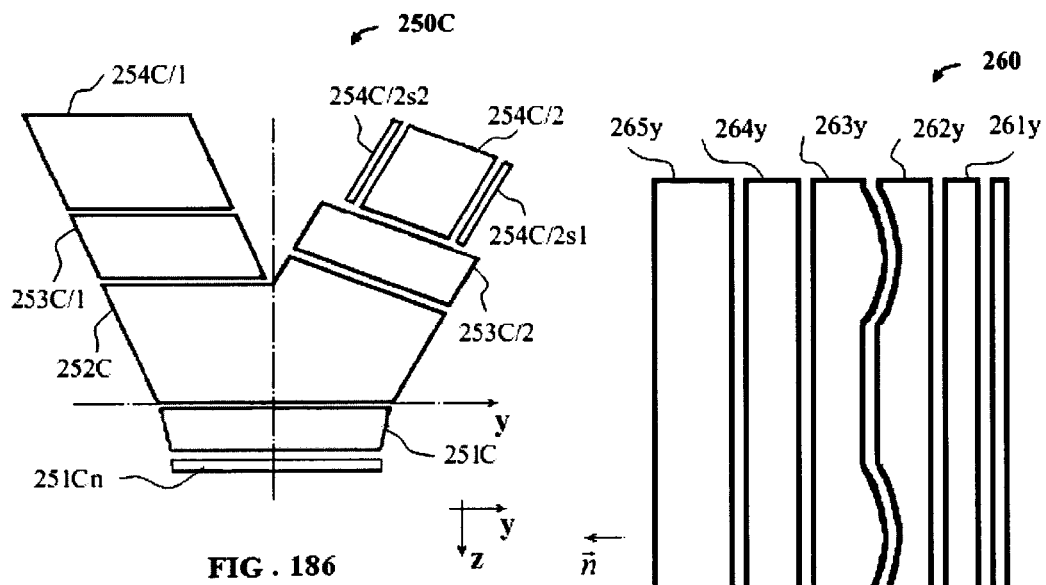
FIG. 186
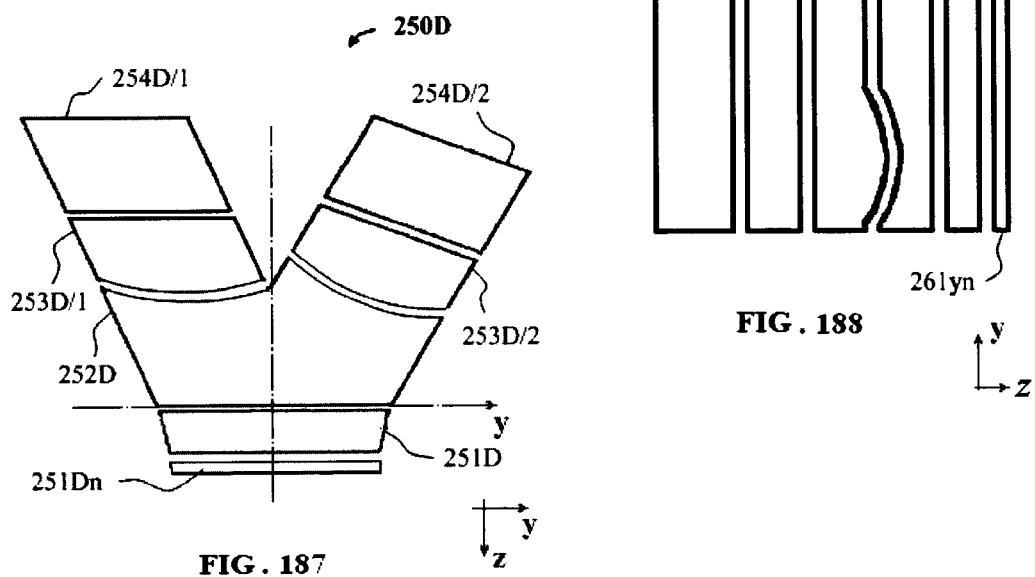
FIG. 187
FIG. 188

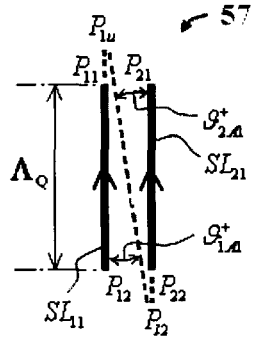
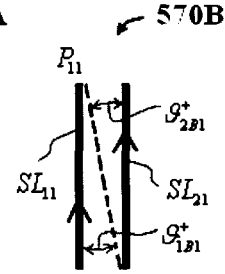
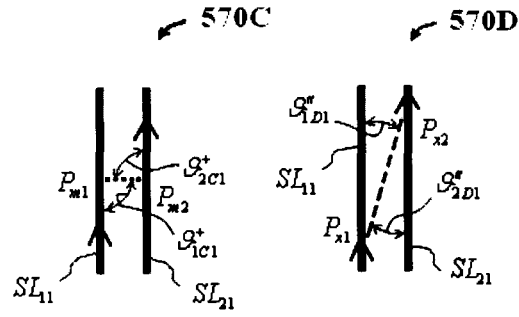
FIG. 239  FIG. 240  FIG. 241  FIG. 242
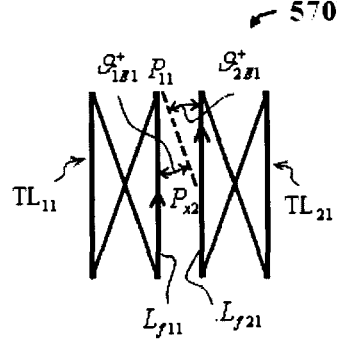
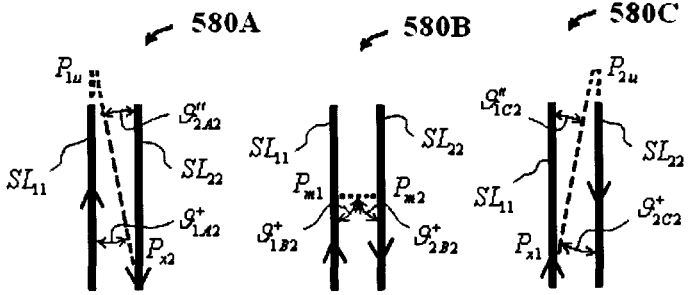
FIG. 243  FIG. 244  FIG. 245  FIG. 246
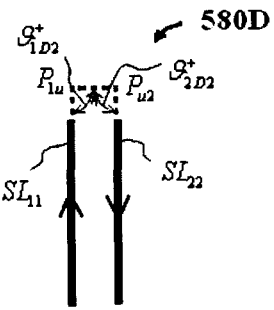
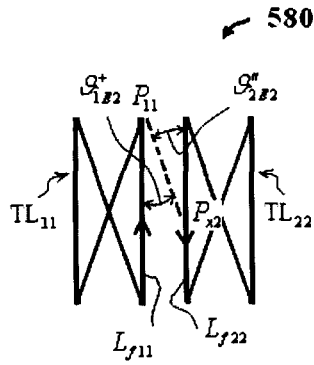
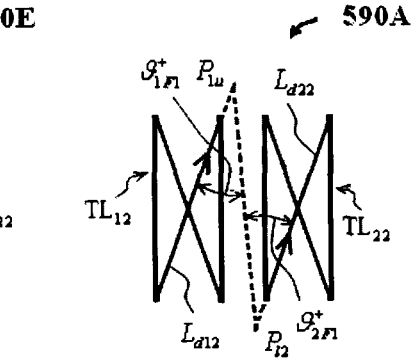
FIG. 247  FIG. 248  FIG. 249

METHOD OF MASS-SPECTROMETRY AND A DEVICE FOR ITS REALIZATION

FIELD OF THE DISCLOSED TECHNOLOGY

This invention may be applied in fields such as medicine, biology, gas and oil industry, metallurgy, energy, geochemistry, hydrology, ecology, food industry, narcotics control, and drug testing.

BACKGROUND OF THE DISCLOSED TECHNOLOGY

Terms used in this disclosure are explained in definitions included in the invention description. Several such terms, related mainly to novel objects proposed herein, require supplemental explanations for their single-valued interpretation which are offered herein. A P-element is defined as an IO (ion-optical) element that is configured to create a two-dimensional mean geometric surface (M-surface, hereinafter) of the IO element. The M-surface is formed by perpendicular displacement of a generated straight line. In a general case, the P-element may be created from a nonplanar two-dimensional mean surface. Particular embodiments of the P-elements are modes in which they combine geometric mean planes and a plane of electric field symmetry and/or of magnetic field antisymmetry.

The P-elements are divided into cartesian-two-dimensional P-elements and three-dimensional P-elements. All P-elements are considered to be three-dimensional P-elements with the exception of Cartesian-two-dimensional type P-elements having uniform or nonuniform heights, depending only on two coordinate axes in Cartesian coordinates. Cartesian-two-dimensional P-elements are divided into planar-two-dimensional P-elements with geometric mean planes and surface-two-dimensional P-elements, such as a M-surface, which is formed by parallel displacement of the straight-line along the bent line, zigzag line or bent-zigzag line.

Several examples of the P-elements are: cylindrical condensers, P-elements having asymmetrically nonuniform heights in a parallel front-edge arrangement of Cartesian-two-dimensional electrodes, plane condensers, P-elements with axially asymmetric horizontal orientation of electrodes and with symmetrically nonuniform height or uniform height of electrodes arrangement, sectoral magnetic P-elements, and conic P-elements (V-shaped, conic).

Extensions of the M-surface off the field of the P-element at its input and output are referred to respectively as the input and output mean planes of the P-element.

The P-elements extended in either direction are referred to as extended P-elements. Extended P-elements are designed for simultaneous or successive actions on a single path or multipath ion flux at different segments along the length of the extended P-element.

Any IO system or sub-system interacting three or more times with an ion flux, such as single multi-reflectors, and any IO system or sub-system comprising three or more P-elements, may be described using projections on two or three mutually perpendicular characteristic planes, e.g., a base plane, an incremental plane or longitudinal-incremental plane, and a transverse-incremental plane.

The base plane of an incremental IO system or sub-system is a plane that is perpendicular to the linear axes of extended P-elements parallel to each other.

At least three quarters of the components of planar IO systems or sub-systems, also referred to as the supporting portion of planar IO systems or sub-systems, may be located on a single plane, e.g., their supporting plane. The base plane of a planar IO system is a plane parallel to the ion flux between three or more conjoined sections of supporting P-elements of the IO system, such that the ion flux passes from one section to the other, and this base plane has the smallest angle relative to the supporting plane of the IO system.

The incremental plane of the IO system or subsystem is a plane perpendicular to the base plane of the IO system or subsystem.

The IO systems are divided into two-dimensional systems and three-dimensional systems. IO systems configured to provide ion motion, mainly close upon one or around one plane, are typically two-dimensional systems (for example, IO planar systems and R-multi-reflectors of rectilinear reflecting type), while other IO systems are typically three-dimensional systems.

A planar IO system or sub-system (e.g., planar R-multi-reflector or planar control subsystem) is considered to be open (non-closed type), if it is configured to provide an out-of-base-plane arrangement of descending and outgoing branches of ion paths in the IO system or sub-system. IO systems or subsystems of a non-closed type are considered to be single-plane systems or sub-systems provided that the descending and outgoing branches of ion paths are arranged in one plane. Any other IO systems or sub-systems of non-closed type, which do not meet these conditions are considered to be non-coplanar.

An open IO system or sub-system is defined as a system or sub-system with parallel-projective symmetrically non-coplanar input/output, if it is configured to provide arrangement of descending and outgoing branches of ion paths in one or more planes, the arrangement being one of a typical line components of this IO system or sub-system and perpendicular to the IO system or sub-system base plane.

In a multinodal reflecting IO system, e.g., in a control subsystem (reflection or reflection/refraction subsystem) or in a R-multi-reflector, any constituent IO reflection units designed to receive the ion flux entering from the outside of the IO system and to remove the ion flux from the IO system are referred to as the first (or receiving) IO reflection unit and the last (or output) IO reflection unit, respectively. Other IO reflection units of the multimodal reflecting IO system are referred to as mean IO reflection units, or, each IO reflection unit is referred to by its number along the streamline of ion flux. For example, in a two-loop reflecting R-multi-reflector with four IO reflection units, the IO reflection unit located on one diagonal segment of a typical line with the receiving IO reflection unit is referred to as the second reflection unit, and the IO reflection unit located on one diagonal segment of a typical line with the output IO reflection unit is referred to as the third reflection unit.

In general, various mass-spectrometric methods and mass-spectrometers (MS) are known. In general, a mass-spectrometric method provides the following:

a) Ionize the substance sample in an ionic source unit and remove the ion flux (ions) out it and form the ion flux and control its motion, including its mass dispersion by ion masses (mass dispersion by values of ion mass/charge ratios, m/z), with the aid of static or variable components of magnetic and/or electric fields. The fields are typically generated by groups of ion-conducting blocks composed of ion-conducting IB-channels with boundary surfaces and channel IO subsystems (P-elements), each of which is a part of a MS-channel within an IO system (series-connected ion-conducting IB-channels and ionic source IB-channel of ionic source unit).

At that, the channel IO subsystem of each ion-conducting IB-channel comprises one or more control subsystems, or comprises a curve main axis in a cross-space dispersing mode or in a multi-reflecting mode;

b) Register ions by means of one or more sensors of a detector system;

c) Control and manage the operations of all blocks of the mass-spectrometer as well as support the data processing by means of a controller-computer system.

A mass-spectrometer (MS) to perform mass-spectrometry processes consists in general of the following:

a) MS-blocks: ionic source unit formed of a group of ion-conducting blocks, composed of a coupling module element and an analyzer-disperser block. The ionic source units include IB-channels with boundary surfaces and channel IO subsystems (P-elements), and each IB-channel of a block is a part of the MS-channel with the IO system, resulting in an ion-conducting IB-channels of ion-conducting blocks together with the ionic source IB-channel of the ionic source unit. The channel IO subsystems (P-elements) comprises one or more IO control subsystems, or comprises a curve main axis in a cross-space dispersing mode or in a multi-reflecting mode;

b) Detector circuit;

c) Controller-computer system. Each IB-channel serves to form and control motions of channel ion flux and includes a channel IO subsystem with one or more IO elements, each of which contains two or more electrodes and one or more boundary surfaces, the surfaces being surfaces of output or surfaces of input and output for channel ion flux. An ionic source type of an IB-channel, also referred to as an IB-channel of an ionic source unit or an ionic source IB-channel, includes surfaces of output, mainly, in coincidence with a boundary electrode of the ionic source IB-channel. An ion-conducting type of IB-channel, also referred to as an IB-channel of an ion-conducting module or an ion-conducting IB-channel, contains boundary surfaces and channel IO subsystems (IO elements), comprising a single control subsystem or more such subsystems; or comprising a curve main axis in a cross-space dispersing mode or in a multi-reflecting mode.

There are multiple alternatives of MS block-structured docking groups depending on specified tasks to be solved by proposed MS means. According to a quantitative module composition of block-structured docking groups, the MS may include different types of MS modularity levels: extended-multimodule and multimodule MS; MS of mean modularity level, medium modular MS and small-section modular MS.

Small-section modular MS are designed to be operated in a single-stage mass-spectrometry process. As such, a MS block-structured docking group is composed of minimum structural elements: a pre-shaping module and a distributing accelerator module. The block-structured docking group of a MS of mean modularity level is composed of a pre-shaping module, a distributing accelerator module and a module of a refinement cell or an ion trapping module.

The block-structured docking group of multimodule MS is composed of a pre-shaping module, a distributing accelerator module, a module of a refinement cell and an ion trapping module. The block-structured docking group of an extended-multimodule MS is composed of a pre-shaping module, a distributing accelerator module, a module of a refinement cell, an ion trapping module, and a module of further ion accumulation trapping.

The MS of mean modularity level including the module of the refinement cell, the multimodule MS, and the extended-multimodule MS allow to carry out molecule structure analyses based on multi-stage, e.g., tandem, mass-spectrometry (MS/MS) or to carry out the spectrometry with multiple-cycle ion accumulation of a certain mass range (MS$\langle n \rangle$).

All known MS, with the exception of parallel multi-channel quadrupole type MS, are single channel, channel-single-path, MS, ensuring simultaneous analysis of only single-path axial ion flux.

Known parallel multi-channel MS, containing, in one vacuum volume, at least several channels, and referred to as parallel MS, comprise a single-stage quadrupole MS. U.S. Pat. No. 7,381,947, Publ. Jun. 3, 2008 describes a single-stage quadrupole MS, including N channels, where N is a integer number greater than one, composed of the following: an ionic source module including N ionic source IB-channels, each of which has a single source of ions; a block-structured docking group provided with a pre-shaping module and a distributing accelerator module, each of which contains N IB-channels; a dispersing analyzer module which contains N dispersing analyzer IB-channels; a detector system, including N ion detectors; and a controller computer system. The dispersing analyzer module comprises N coupled quadrupole IB-channels having common interchannel electrodes, each of which is a single-path (single-flow) channel.

This MS type, just as all known single-stage MS with a quadrupole ion trap, is notable for its poor weighing accuracy, i.e., up to <20 ppm and shows a relatively low resolution power up to several tens of thousands.

The main disadvantage of this MS type is in the low value of resolution power/costs ratio. Moreover, this MS type is related to low-modular MS and does not allow to carry out structure analyses.

Known methods of spectrometry and mass-spectrometer (MS) described in the invention of A. Makarov (Pub. No.: US 2009/0166528 A1, Publ. Jul. 2, 2009) is the closest prototype to the claimed invention. The block-structured docking group of this MS prototype comprises a pre-shaping module, a distributing accelerator module, a refinement cell, and a module of ion trapping. Some MS versions optionally comprise a module of further ion accumulation. Each MS module comprises one IB-channel. Depending on the type of dispersing analyzer IB-channel, different MS versions comprise a different number of detector modules and outputs to them. The Makarov reference (trapping distribution module) is mainly used as a dispersing analyzer IB-channel. Additionally, this prior invention teaches other versions of dispersing analyzer IB-channel embodiment, e.g. in a multi-reflecting mode.

The Makarov prototype is notable for its high weighing precision in multi-reflecting mode up to <2 ppm (at internal calibrations). It has resolution power over 100000. Such a device costs several millions of US$.

The main disadvantage of this prototype is in low value of resolution power/costs ratio (marginal costs). It provides no MS versions assuring flexible configuration modification for specific tasks through varied levels of block-structured docking group modularity. Moreover, this prototype does not consider species of electric (nonmagnetic) time-of-flight (TOF) IB-channels and their characteristics promising to enhance values of resolution power/costs ratios.

Values of the resolution power/costs ratio and the MS power potentials are determined mainly by the MS modularity level as well as by the functional characteristics and by the cost of IB-channels (especially by the resolution power of dispersing analyzer IB-channel and the IB-channel of ion trapping, if any) suitable for assembly of such modules.

The MS with different modularity levels are commonly based on use of electric IB-channels of multi-resolution modes, such as nonmagnetic static electric fields or electric fields with variable components, by virtue of the resolution power/costs ratio in their operations as IB-channels of ions trapping and mass dispersing analyzer IB-channel. A nonmagnetic/electric IB-channel differs from other types of IB-channels (e.g., with double focusing, ion cyclotron resonance, sectoral-magnetic, Fourier analyzers etc.) by smaller geometrical dimensions, masses and power capacity, and by a simple and reliable design. Moreover they are relatively cheap. E.g., nonmagnetic time-of-flight MS (TOF MS) based on the electric time-of-flight IB-channel surpasses other MS types by its unlimited mass ranges (up to tens of millions of atomic mass) and higher analysis rates. These TOF MS functional capabilities allow to carry out analyses unreachable by means of other types of mass-spectrometers, e.g., analyze time-varying processes or organic matters which are mixtures of different individual compounds (e.g., oil).

Currently there are known electric TOF IB-channels used in MS, which may be classified by four main resolution levels, i.e.: first resolution level specifies the radio frequency TOF IB-channels of linear type (variable fields) and of electrostatic type with a straight main optical axis (static fields); second resolution level specifies the reflectron TOF IB-channels (with straight main optical axis and single-reflecting channels); third resolution level specifies the reflectron TOF IB-channels with a curved main axis (including single-, double-, and triple-reflection subsystems with a curve axis or reflection-refraction subsystem) and having vectors of input and output path ion flux spaced from each other; fourth resolution level specifies the multi-reflecting TOF IB-channels (over five reflections).

There are known linear radio frequency (variable fields) and electrostatic with straight main optical axis (static fields) TOF IB-channels used in different linear TOF MS (s-TOF MS)—such as AXIMA-LNR [www.analyt.ru], MSX-4 [www.niivt.ru] and those described in patent RU 2367053. In linear radio frequency IB-channels (e.g., RU 2367053) plate electrodes generating periodic two-dimensional linear high frequency (HF) fields are provided along the axis between ions source and ions detector. HF fields step up the path and time of ion movement in the TOF MS, enhancing ions dispersion by masses (i.e., enhancing MS resolution capacity) as compared to electrostatic IB-channels with a straight main optical axis (static fields).

Linear TOF IB-channels in the TOF MS provide only a low resolution level (resolution reaches some hundreds), but they are small-sized, simple in operations, and power and cost saving.

There are known reflectron TOF IB-channels (e.g.: RF patent No. 2 103 763 C, Publ. 27 Jan. 1998; U.S. Pat. No. 4,694,168, Publ. 15 Sep. 1987) used in the reflectron TOF MS (sR-TOF MS) where the area of all operating processes of ion flux covers the TOF MS straight main axis. The reflectron IB-channel in each such sR-TOF MS comprises a special area of a single reflection of ion packages within an electric field. Reflection of an ion package is used to enhance resolution power through time-of-flight focusing of the ion package by ionic energy. As with all known patents and manufactured devices related to the sR-TOF MS, in order to reflect ion packages there are applied uniform electric fields enclosed by one or several fine-meshed metal screens.

A method of single-reflecting spectrometry with straight main optical axis based on the reflectron IB-channel consists of directing ion packages towards one or several electric fields, enclosed by screens, at a right angle to the mesh planes, reflection of the ion packages throughout the electric fields and further ion package logging. As such, along the path from the source to the detector, ion packages pass twice through each screen required to generate electric fields commonly considered as uniform.

Reflectron IB-channels in a sR-TOF MS provide a mean resolution level (resolution reaches up to several thousand), while they are small-sized, simple in operations, and powerand cost saving.

The main sR-TOF MS disadvantage is in the relatively low resolution power due to the fact that the fine-mesh screens located in the area of ion movement give rise to several phenomena adversely affecting the performance characteristics of reflectron IB-channels, in particular, to ions scattering at the screens and uncontrolled extra ionic energy spread, and consequently, to lowering of IB-channel resolution power.

There are known reflectron TOF MSs (cR-TOF MS) comprising IB-channels with ion flux axes spaced from each other (for spaced source and detector) and with a curved main axis (e.g.: U.S. Pat. No. 6,621,073, B1, Publ. 16 Sep. 2003; US, 2008/0272287 A1, Publ. 6 Nov. 2008).

Methods described in the above mentioned patents consist of operation of an IB-channel with one to three reflecting electric fields and direction of ion packages emitted by a source into these reflecting electric fields at acute angles relatively to vectors of the fields; of ion packages reflecting in the electric fields; and further of ion packages logging.

In U.S. Pat. No. 6,621,073, B1 and US patent 2008/0272287 A1 the IB-channels comprise uniform electrostatic or reflector fields enclosed by one or several close-mesh screens extended at slit diaphragms. In US patent 2008/0272287 A1, the diaphragms and detector slits are sized considering that the width of a reflected ion package is greater than its width when incoming due to different ionic energy in the package.

There is known a single-reflecting and triply-reflecting embodiment of an IB-channel used in cR-TOF MSs (U.S. Pat. No. 6,717,132 B2, Publ. Apr. 6, 2004), specifying gridless reflector fields generated by slit diaphragms for single-triple reflections. Herein it is assumed that the field of slit diaphragms within an area of ion flux passage is a Cartesian-two-dimensional field, in which no forces act on the ions in a horizontal direction.

The main disadvantage of the IB-channel with a Cartesian-two-dimensional field consists in the default of focusing ions in a direction parallel to the middle plane and in a slit that gives rise to ion scattering, and consequently, to lowering of resolution power of the cR-TOF MS including with such an IB-channel.

The known cR-TOF MSs operate in a resolution ranging from several thousands to several tens of thousands depending on their design, though the average sensitivity level is equal to $10^{-4}$.

There are known IB-channels having a curved main axis in a cross-space dispersing mode with two-dimensional electric and/or magnetic fields, e.g. V-shaped or conic, (papers of Spivak, Lavrov I. F. and others) in expressly selected coordinates. There are known the IB-channels having a curved main axis in a cross-space dispersing mode with Cartesian-two-dimensional electric and magnetic (prismatic) fields (papers of Kelman V. M., Yakushev E. M. and others.). The main disadvantage of such IB-channels is in a low value of resolution power/costs ratio.

There is known a multi-reflecting MS with an IB-channel comprising a channel IO subsystem of multi-reflector type (oMR-TOF MS) configured for single rectilinear reflecting mode and including a stepped R-multi-reflector of narrow form (certificate of authorship SU 1725289 A1 dated 7 Apr. 1992, Bulletin No. 13). A stepped R-multi-reflector of narrow form is designed to provide potential ion movement through the paths whose projections on the R-multi-reflector base plane are approximately linear segments. A stepped R-multi-reflector of narrow form comprises two single-zone extended reflector R-modules of a Cartesian-two-dimensional type arranged opposite one another when their axial vectors are anti-parallel and are located in the same plane (in a M-plane of R-multi-reflector), where their axial lines are parallel to each other and perpendicular to the R-multi-reflector base plane. Ions are subjected to multiple reflections between single-zone extended Cartesian-two-dimensional R-reflectors. As such, the ions slowly drift towards the detector in a drift direction moving towards the linear axes of the extended reflector R-modules located in a longitudinal R-multi-reflector plane. The number of cycles and resolution level are corrected through modifications of the ion injection angle.

The description of the mentioned certificate of authorship discloses theoretical principles of MR-TOF MS performance analysis and computation.

Disadvantages of the mentioned cR-TOF MS designs and operations are in the default of focusing along the parallel longitudinal-incremental plane of R-multi-reflector. When an ion flux traverses certain tracks along the parallel longitudinal-incremental plane of R-multi-reflector the dispersion of ion flux reaches values rendering the attempts to detect mass spectrum meaningless.

U.S. Pat. No. 7,385,187 B2; Jun. 10, 2008 developing concepts of authorship certificate SU 1725289 A1, of 7 Apr. 1992, Bull. No. 13, proposes to provide an electrostatic lens in the IB-channel between two periodic single-zone extended R-reflection units of a Cartesian-two-dimensional type. An electrostatic lens allows directing ion packages along the linear axes (in a longitudinal-incremental plane) of the extended reflector R-modules. Such an analyzer allows retaining permanent ion fluxes within long-distance span lengths and enhancing TOF ions dispersion by mass while providing low space and time aberrations, thus achieving a high resolution power.

U.S. Pat. No. 7,385,187 B2 also describes the principle of parallel tandem time-of-flight analysis in an "embedded times" mode, substantially enhancing the efficiency of complex biopolymer mixture analysis.

Experimental oMR-TOF MS studies (Verenchikova A. Abstract of PhD thesis, St. Petersburg, 2006) demonstrate high resolution power exceeding 200000 of the analyzer as described in U.S. Pat. No. 7,385,187 B2.

US patent 2010/008386 A1, Publ. Jan. 11, 2010, developing concepts of U.S. Pat. No. 7,385,187 B2; Jun. 10, 2008, proposes for a single rectilinear reflector IB-channel of multi-reflecting mode extended R-reflection units to provide periodic modulations of electrostatic fields along the longitudinal-incremental propagation of an ion flux, for the purpose of periodical space focusing of ion packages. In addition to this periodic modulation of electrostatic fields there is provided at least one isochronic curve of an interface surface between a pulsed ion source and a receiver in the MS.

One of the most serious disadvantages of known oMR-TOF MSs is in direct multicycle operation mode required to achieve high resolution power in the IB-channel with an IO channel subsystem configured as a single multireflector. In such IB-channels the paths of extended ions fluxes have multiple intersections that lead to Coulomb ions scattering, desensitization and decreased oMR-TOF MS resolution power; lighter ions may go ahead of heavier ions by one and more cycles, resulting in obtained mass spectrum multiplicity; extended R-reflectors with isochronic curved surfaces are used in addition to periodic modulations of electrostatic fields, even though each of them may be used individually.

SUMMARY OF THE DISCLOSED TECHNOLOGY

A major objective of this invention is to propose a method of mass-spectrometry, and a device for its implementation, based on efficient ion flux control in the MS to improve the values of resolution capacity/cost ratios which are resolution/cost indices of different MSs. Herein alternative embodiments of spectrometry methods and devices cover all MS modularity and resolution levels.

Moreover this invention provides a gain in the sensitivity, precision and measurement rates of substance compositions and structures concurrently with enhancement of analyzer functional capabilities and with downsizing and mass reduction. One more problem solved in claimed invention is the extension of mass-spectrometry potentials.

The proposed method and device of mass-spectrometry meet the standards of invention since on the filing date no similar engineering solution was known. The method and device of mass-spectrometry have a number of characteristic features distinguishing them from known methods and devices of mass-spectrometry. The proposed method and device of mass-spectrometry may be implemented using available equipment and commercially available materials, component parts and technologies.

Proposed method of mass-spectrometry is implemented as follows:

(a) ionizing a substance sample in an ionic source block, formation an ion flux in MS, managing motion of said ion flux including mass dispersion of the ion flux by mass/charge ratio, by means of at least one of a magnetic field and an electric field; said magnetic field and said electric field generated by groups of ion-conducting blocks comprising ion-conducting IB-channels with IO channel systems, where IB-channels are part of a MS-channel with its own MS-channel IO system; wherein said MS channel comprises at least one said ion-conducting IB-channel and at least one ionic source IB-channel of said ionic source block connected in series, wherein said IO channel system of each said ion-conducting IB-channel comprises at least one of: a subsystem with a curved main axis in a cross-space dispersing mode, a subsystem with a curved main axis, in a multi-reflecting mode, and any other subsystem, hereinafter named as a management subsystem, (b) registering ions in said ion flux using at least one detector group of a detector system;

(c) controlling and managing of all blocks of a mass-spectrometer as well as supporting data processing in said mass spectrometer using a controller-computer system.

Main distinction of proposed method from the known technique consists in that the forming of ion flux and control of its motion are performed at least by one of operations decided-on among the following:

(a) parallel mass-spectrometry in a said MS-channel using one mode selected from: channel-multipath ion flux including a mode with multi-cell section surfaces, off-axis channel-single-path ion flux, including a mode with double-cell section surfaces;

(b) control of said ion flux using an electric IO channel system comprising at least one of an IO element enabling selection of a specified spatial orientation of said IO element relative to at least one other IO element and relative to a direction of an averaged vector of said ion flux entering said IO element, a flat unary P-multireflector, a three-dimensional P-multireflector, a cascade-multilayered multireflector, an extended P-element of refraction, a three-dimensional P-element of reflection, a P-element of non-uniform height, and a P-element of reflection with a two-dimensional reflection zone.

Other distinctions of proposed method from the known technique consist in the following:

enabling single-channel and multichannel mass-spectrometry, wherein said ion flux comprises at least one single-path ion flux which passes through said MS-channel, wherein each said path ion flux is detected by an individual detector of said detector system;

the said path ion fluxes comprises at least two path ion fluxes, each received from a different source, and injected into at least one of said groups of ion conducting blocks through a different output gate of an ionic source system;

the said at least two path ion fluxes exiting from at least one said output gate of said ionic source system are supplied in at least one of: independently of one another, and in a time correlation function relative to one another;

the values of said mass dispersion and of energy dispersion of said ion flux are regulated by energy spectrometry performed concurrently with mass-spectrometry, and mass-spectrometry at specified range intervals of an energy spectrum of said ion flux;

the one cyclicity mode used in passage of said ion flux is selected from the group consisting of single-cycle ion passage, and multi-cycle ion passage through at least some said IB-channels;

the said mass-spectrometry is performed using a mode selected from the group consisting of: single-staged mode, MS/MS mode, and MS⟨n⟩-mode;

the cross-spatial space focusing of said ion flux is performed on a detector surface, at least along one of two cross-spatial space directions;

the cross-spatial space focusing of said ion flux is performed along a path of motion of said ion flux by means of pulsating voltage;

the said mass spectrometry comprises time-of-flight mass-spectrometry, selected from the group consisting of MS⟨n⟩-type and MS/MS-type, and is performed by an nested time mode.

To implement the proposed method of mass-spectrometry it is proposed the nonmagnetic management subsystem for management of charged particle flux, decided-on among the series of its functional versions:

(a) a subsystem of refraction comprising at least one IO element of refraction;

(b) a subsystem of reflection comprising n local IO elements of reflection, where: n is an integral number and n≤3 and including no more than two local P-elements of reflection and extended IO elements of reflection;

(c) a mixed subsystem of reflection and refraction, comprising said subsystems (a) and (b); and (d) a multifunctional subsystem, comprising one of said subsystems (a), (b) and (c), wherein at least one IO element is multifunctional and enables selection of at least two operation modes selected from the group consisting of: refracting, reflecting and field-free.

Main distinction of proposed management subsystem from known management subsystems consists in that it comprises at least, one IO element selected from the group consisting of: IO element enabling selection of a specified spatial orientation of said IO element relative to at least one other IO element and relative to a direction of an averaged vector of said ion flux entering said IO element, a flat unary P-multireflector, a three-dimensional P-multireflector, a cascade-multilayered multireflector, an extended P-element of refraction, a three-dimensional P-element of reflection, a P-element of non-uniform height, and a P-element of reflection with a two-dimensional reflection zone.

Other distinctions of proposed management subsystem from known management subsystems consist in the following:

comprising a local IO element having at least one of functional and design characteristics, wherein said local IO element is selected from the group of functional characteristic IO elements consisting of: a local IO elements of refraction, a local IO lens, a local telescopic IO element, a local IO prism, a local cylindrical condenser, a local plane condenser, a local IO mirror, a single-zone local IO element of reflection, a vertical double-zone local IO element of reflection, a horizontal double-zone local IO element of reflection, a joint group of local IO elements of reflection wherein each pair of reflecting elements shares a common electrode, and a local multifunctional IO element, wherein said local IO element is selected from the group of design characteristic IO elements consisting of: a local two-dimensional IO element, a Cartesian two-dimensional IO element on a plane, a condenser of non-uniform height on a plane, a plane condenser, a Cartesian two-dimensional IO element on a surface, a condenser of non-uniform height on a surface, a cylindrical condenser, a local three-dimensional IO element, a local doubly symmetric IO element, a sectorial transbending IO element, a sectorial transaxial IO element, a V-shaped IO element, a conic IO element, a crossed IO element, a boxlike IO element, a transbending-mixed IO element, a crossed-mixed IO element, a boxlike-mixed IO element, and a heterogenic-mixed IO element;

comprising at least one extended IO element selected from the group consisting of single-staged and array-staged extended IO elements, having at least one of functional and design features, where said extended IO element is selected from the group of functional feature IO elements consisting of: an extended IO element of refraction, an extended IO lens, an extended telescopic IO element, an extended IO prisms, an extended IO element of reflection, a single-zone extended IO element of reflection, a vertical double-zone extended IO element of reflection, a horizontal double-zone extended IO element of reflection, a joint group of extended IO elements of reflection wherein each pair of reflection elements shares a common electrode, and an extended multifunctional IO element, wherein said extended IO element is selected from the group of design characteristic IO elements consisting of: an extended two-dimensional IO element, a Cartesian two-dimensional IO element on a plane, a condenser of non-uniform height on a plane, a plane condenser, a Cartesian two-dimensional IO element on a surface, a condenser of non-uniform height on a surface, a cylindrical condenser, an extended three-dimensional IO element, an extended doubly symmetric IO element, an alternating sectorial transbending IO element, an alternating sectorial transaxial IO element, an alternating V-shaped IO element, an alternating conic IO element, an alternating crossed IO element, an alternating boxlike IO element, an alternating transaxial bending-mixed IO element, an alternating crossed-mixed IO element, an alternating boxlike-mixed IO element, and an alternating heterogenic-mixed IO element;

wherein said at least one IO element comprises a doubly symmetric IO element, and electrode operating surfaces of said IO element are arranged as at least one of planar operating surfaces, concave operating surfaces, and a pair of parallel identical planar operating surfaces such that adjacent facing frontal lines of at least one electrode pair are described by sections of second-order curves;

wherein said at least one IO element comprises an axisymmetric IO element, and electrode operating surfaces of said IO element are selected from the group consisting of: cylinder surfaces diaphragm-electrode surfaces; surfaces as sectors of cones; and revolving surfaces, generated by rotation of components thereof about a straight axis and described by segments of second-order curves, wherein at least one electrode of said IO element comprises at least one hole for ion flux passage;

wherein said electrode operating surfaces comprise diaphragm-electrode operating surfaces having one of planar and concave forms;

wherein said IO element comprises an IO element of reflection having an cover electrode, such that it is located perpendicular to an axis of the IO element and it's located boundary and limits the motion of said ion flux by way of reflection;

comprising a P-element configured to allow ions in said charged particle flux to move on portions of an M-surface proximate said P-element;

wherein said P-element comprises a first P-element comprising one of a P-element of reflection and a multifunctional P-element, and additionally comprises at least one IO element of refraction configured as a second P-element, such that output and input mean planes of said first and second P-elements are substantially parallel, comprising a P-element configured to allow ions in said charged particle flux to move proximate a longitudinal-vertical plane of said P-element, wherein said P-element comprises at least one P-element being one of a P-element of reflection and a multifunctional P-element, and additionally comprises at least one IO element of refraction configured as a P-element, wherein longitudinal-vertical planes of said at least one P-element and said IO element of refraction are substantially parallel, the said at least one IO element comprises a first IO element and a second IO element, defining:

an angle $\beta_{(12)1}$ between vectors read counterclockwise from a unitary vector $\vec{n}_{(12)}$, directed from said first IO element towards said second IO element and arranged on a line interconnecting effective points of reflection/refraction on a path ion flux of said first and second IO elements, towards a unitary axial vector $\vec{n}_1$ of said first IO element, wherein said angle $\beta_{(12)1}$ is within the range 0

$$p\beta_{(12)1} p \frac{\pi}{2};$$

and an angle $\beta_{(12)2}$ between vectors read counterclockwise from said unitary vector $\vec{n}_{(12)}$ towards a unitary axial vector $\vec{n}_2$ of said second IO element, wherein said angle $\beta_{(12)2}$ is within the range $$\pi p \beta_{(12)2} p \frac{3\pi}{2},$$

the said angle $\beta_{(12)1}$ is within the range $$0 p \beta_{(12)1} p \frac{\pi}{2},$$

and said angle $\beta_{(12)2}$ is within the range $$\frac{\pi}{2} p \beta_{(12)1} p \pi;$$

comprising first, second, and third identical IO elements, configured such that:

said angle $\beta_{(12)1}$ is within the range $$\frac{3\pi}{2} p \beta_{(12)1} p 2\pi;$$

said angle $\beta_{(12)2}$ is within the range $$\pi p \beta_{(12)2} p \frac{3\pi}{2};$$

an angle $\beta_{(23)2}$, defined between vectors read counterclockwise from a unitary vector $\vec{n}_{(23)}$, directed from said second IO element towards said third IO element and arranged on a line interconnecting effective points of reflection/refraction on a path ion flux of said second and said third IO elements, towards said unitary axial vector $\vec{n}_2$, is within the range $$\frac{3\pi}{2} p \beta_{(23)2} p 2\pi;$$

and an angle $\beta_{(23)3}$, defined between vectors, read counterclockwise from said unitary vector $\vec{n}_{(23)}$ towards a unitary axial vector $\vec{n}_3$ of said third IO element, is within the range $$\pi p \beta_{(23)3} \frac{3\pi}{2};$$

the said first, second, and third identical IO elements are configured such that said angle $\beta_{(12)1}$ is within the range $$0 p \beta_{(12)1} p \frac{\pi}{2},$$

said angle $\beta_{(12)2}$ is within the range $$\pi p \beta_{(12)2} p \frac{3\pi}{2},$$

said angle $\beta_{(23)2}$ is within the range $$\frac{3\pi}{2} p \beta_{(23)2} p 2\pi,$$

and said angle $\beta_{(23)3}$ is within the range $$\frac{\pi}{2} p \beta_{(23)3} p \pi;$$

wherein said first, second, and third identical IO elements are configured such that said angle $\beta_{(12)1}$ is within the range $$\frac{3\pi}{2} p \beta_{(12)1} p 2\pi,$$

said angle $\beta_{(12)2}$ is within the range $$\pi p \beta_{(12)2} p \frac{3\pi}{2},$$

said angle $\beta_{(23)2}$ is within the range $$\frac{3\pi}{2} p \beta_{(23)2} p 2\pi,$$

and said angle $\beta_{(23)3}$ is within the range $$\frac{\pi}{2} p \beta_{(23)3} p \pi;$$

comprising a multi-element P-element arranged in a horizontal-straight-line and configured to allow arrangement of said averaged vector of said charged particle flux on an M-surface proximate said P-element;
the output and input mean planes of P-elements forming part of said management subsystem are parallel to each other;
comprising two P-elements having output and input mean planes intersecting at an angle $\overline{\omega}_P$, and configured to allow substantial coinciding of a line of intersection of said mean planes with said averaged vector of said path ion flux at a midway point between said P-elements, wherein said angle $\overline{\omega}_P$ is within the range $$0 p \overline{\omega}_P p \frac{\pi}{2};$$

it is performed as a reflection subsystem wherein the projections $\vartheta'_{P_1 y}$ and $\vartheta'_{P_2 y}$, correspond to angles $\vartheta'_{P_1}$ and $\theta_{P2}'$ on its base plane (superposed by coordinate plane yz) and projections $\vartheta'_{P_1 x}$ and $\vartheta'_{P_2 x}$, corresponding to angles $\vartheta'_{P_1}$ and $\vartheta'_{P_2}$, on their longitudinal-incremental plane (superposed by coordinate plane xz), on the assumption that $\theta_{P1}' = \theta_{P2}'$ are determined respectively by formulas:

$$\vartheta'_{P1y} = \vartheta'_{P2y}$$
$$= \arctg\left[(tg\vartheta_p)\sin\frac{\varpi_P}{2}\right];$$

$$\vartheta'_{P1x} = \vartheta'_{P2x}$$
$$= \arctg\left[(tg\vartheta_p)\cos\frac{\varpi_P}{2}\right],$$

wherein: $\vartheta'_{P_1}$—angle of input-reflection of one P-element e, $\theta_{P2}'$—angle of input-reflection of the other P-element,
additionally comprising at least one IO element of refraction configured as a series of single IO lens elements,
the said at least one IO element of refraction is a P-element of refraction, having at least one of input and output mean planes which are substantially parallel to at least one of input and output mean planes of symmetry of at least one of two adjacent P-elements of reflection,
comprising a multi-element P-element arranged in a vertical straight-line and configured to allow arrangement of said averaged vector of said charged particle flux on a longitudinal-vertical plane proximate said P-element;
comprising two P-elements having longitudinal-vertical planes which are substantially parallel to each other;
comprising two P-elements having longitudinal-vertical planes intersecting at an angle $\overline{\omega}_\perp$ and configured to allow coinciding of a line of intersection of said longitudinal-vertical-planes with said averaged vector of said path ion flux at a midway point between said P-elements, wherein said angle $\overline{\omega}_\perp$ is within the range $$0 p \overline{\omega}_\perp p \frac{\pi}{2};$$

it is performed as a subsystem of reflection, where projections $\vartheta'_{\perp 1 y}$ and $\vartheta'_{\perp 2 y}$, correspond to angles $\vartheta'_{\perp 1}$ and $\vartheta'_{\perp 2}$ on its base plane (superposed by coordinate plane yz) and projections $\vartheta'_{\perp 1 x}$ and $\vartheta'_{\perp 2 x}$ correspond to angles $\vartheta'_{\perp 1}$ and $\vartheta'_{\perp 2}$ on their longitudinal-incremental plane (superposed by coordinate plane xz), on the assumption that $\vartheta'_{\perp 1} = \vartheta'_{\perp 2}$, are determined respectively by formulas:

$$\vartheta'_{\perp 1x} = \vartheta'_{\perp 2x} = \arctg\left[(tg\vartheta'_\perp)\cos\frac{\varpi_\perp}{2}\right];$$
$$\vartheta'_{P1x} = \vartheta'_{P2x} = \arctg\left[(tg\vartheta'_\perp)\sin\frac{\varpi_\perp}{2}\right],$$

$\vartheta'_{P2x} = 2\pi - \vartheta'_{P1x}$, where: $\theta_R'$—angle of entry-reflection of one P-element e, $\vartheta'_{P2}$—angle of entry-reflection of other P-element;
additionally comprising at least one IO element of refraction;
the said at least one IO element of refraction is a P-element of refraction having at least one of input and output mean planes which are substantially parallel to at least one of input and output mean planes of symmetry of at least one of two adjacent P-elements of reflection;

comprising a multi-element P-element configured to allow arrangement of said averaged vector of said charged particle flux in different planes before entering a field of said management subsystem and after leaving said field of said management subsystem, wherein input and output are of a hetero-planar type;

comprising a projecting-parallel symmetrically heteroplanar input-output, said management subsystem being selected from the group consisting of horizontal-straight-line and vertical straight-line management subsystems;

comprising a multi-element P-element configured to allow arrangement of said averaged vector of said charged particle flux in one plane, equivalent to arrangement before entering a field of said management subsystem and after leaving said field of said management subsystem;

comprising antiparallel input-output and selected from the group consisting of horizontal-straight-line and vertical straight-line management subsystems;

the said input-output converges at an scalene angle;

comprising at least one diaphragm-electrode including at least one hole, wherein a configuration of said at least one hole is selected from the group consisting of: round, oval, quadrupole, and quadrupole with rounded edges;

the said at least one hole of said diaphragm-electrode is configured to cross over at least one of mean plane and a symmetry axis of said management subsystem, and wherein at least one said diaphragm-electrode is configured to control a size and a configuration of said at least one hole, thereby causing changes in functional features of said management subsystem.

To implement the proposed method of mass-spectrometry the P-multireflector for controlling an ion flux configured to allow at least four ion flux reflections in an electric field, comprising two modes of operation selected from the group consisting of an incremental mode of narrow shape and a unary mode shape, wherein, when said P-multireflector comprises a P-multireflector of narrow shape, said P-multireflector is selected from the group consisting of: straight-line-reflecting, one-loop-reflecting, arc-wise-reflecting, and two-loop-reflecting, and Wherein, when said P-multireflector comprises a unary P-multireflector of wide shape, said P-multireflector is selected from the group consisting of second-order curvilinear and n-faced.

Other distinctions of proposed P-multireflector from the known P-multireflectors consist in the following:

comprising a local IO element having at least one of functional and design features, wherein said local IO element is selected from the group of functional characteristic IO elements consisting of: a local IO element of refraction, a local IO lens, a local telescopic IO element, a local IO prism, a local cylindrical condenser, a local plane condenser, a local IO mirror, a single-zoned IO element of reflection, a vertically dual-zoned IO element of reflection, a horizontally dual-zoned local IO element of reflection, a joint group of a local IO element of reflection wherein each pair of reflecting elements shares a common electrode, and a local multifunctional IO element, and wherein said local IO element is selected from the group of design characteristic IO elements consisting of: a local two-dimensional IO element, a Cartesian two-dimensional IO element on a plane, a condenser of non-uniform heights on a plane, a plane condenser, a Cartesian two-dimensional IO element on a surface, a condenser of non-uniform heights on a surface, a cylindrical condenser, a local three-dimensional IO element, a locally doubly symmetric IO element, a sectoral transbending IO element, a sectoral transaxial IO element, a V-shaped IO element, a conic IO element, a crossed IO element, a boxlike IO element, a transbending-mixed IO element; a crossed-mixed IO element; a boxlike-mixed IO element, and a heterogenic-mixed IO element;

comprising at least one extended IO element selected from the group consisting of single-extended and array-extended IO elements, having at least one of functional and design features, wherein said extended IO element is selected from the group of functional feature IO elements consisting of: an extended IO element of refraction, an extended IO lens, an extended telescopic IO element, an extended IO prism, an extended IO element of reflection, a single-zoned extended IO element of reflection, a vertically dual-zoned extended IO element of reflection, a horizontally dual-zoned extended IO element of reflection, a joint group of extended IO elements of reflection wherein each pair of reflection element shares at least one common electrodes, and wherein said extended IO element is selected from the group of design characteristic IO elements consisting of: an extended two-dimensional IO element, a Cartesian two-dimensional IO element on a plane, a condenser of non-uniform height on a plane, a planar condenser, a Cartesian two-dimensional IO element on a surface, a condenser of non-uniform height on a surface, a cylindrical condensers, an extended three-dimensional IO element, an extended doubly symmetric IO element, an alternating sectoral transbending IO element, an alternating sectoral transaxial IO element, an alternating V-shaped IO element, an alternating conic IO element, an alternating crossed IO element, an alternating boxlike IO element, an alternating transaxial-bending-mixed IO element, an alternating crossed-mixed IO element, an alternating boxlike-mixed IO element, and an alternating heterogenic-mixed IO element;

configured as a single type second-order curvilinear P-multireflector comprising one group of electrodes, wherein adjacent facing frontal lines of electrodes in said group are defined by segments of second-order curves and at least one electrode comprises at least one hole for passing of said ion flux;

configured as a single sectoral type second-order curvilinear P-multireflector comprising one group of electrodes wherein adjacent facing frontal lines of electrodes in said group of electrodes are described by segments of second-order curves;

configured as a second order curvilinear P-multireflector, wherein a type of second-order curvilinear structure is selected from the group consisting of: single-zoned, vertically dual-zoned, and three-dimensional;

configured as a second order curvilinear P-multireflector, wherein a distance between a geometric center of said P-multireflector and a nearest electrode gap is substantially greater than a mean distance between electrodes;

configured as a single type n-faced P-multireflector comprising one group of electrodes, wherein adjacent facing frontal lines of electrodes in said group of electrodes are defined by continuous lines, each of which generates an n-isofaced polygon, wherein each electrode in said group of electrodes comprises-segments, and wherein said group of electrodes comprises at least one hole for input-output of said ion flux;

configured as a j/n-single sectoral type a n-faced P-multireflector, comprising j faced sectoral segments and n−1 faces;

configured as a disjunctive n-faced P-multireflector, comprising a group of n local P-elements of reflection arranged in alternating modes on each face of an n-polyhedral polygon;

configured as a j/n-sectoral/disjunctively-faced a n-faced P-multireflector, comprising j-faced sectoral segments of a disjunctively-faced n-faced P-multireflector including n−1 faces;

wherein types of n-faced categories have the number of faces decided-on referring to the equation $$n \approx \frac{2\pi R}{3d}$$

wherein: n-number of faces (n—odd integer and n≥5), d—mean distance between electrode armatures (gap width), R—distance from the geometric center of the P-multireflector to the first electrode gap;

comprising a unary type element configured to allow representation of reflected paths of ion motion outside a field of said P-multireflector in projections on a base plane of said P-multireflector as reflected from a single effective surface of reflection having a section described by a second-order curve;

comprising a unary type element which is selected from the group consisting of single-zoned and vertically dual-zoned types;

comprising at least two P-multireflectors of at least one of local types and extended types, wherein each of said local types and said extended types of P-multireflector is configured to allow ions to move along a generic line in accordance with requirements to input and output fluxes, when it is performed with option feature to reflect from each P-element of reflection the width (longitudinal size) $L_Q$-thickness (transverse size) $L_{MRh}$ ratio of the P-multireflector plotted on the projections to its base plane is confined within the range $$1.5 \leq \frac{L_Q}{L_{MRh}} \leq 100,$$

wherein a drift space (field-free space) is generated between the P-element of reflection within the midway of its length;

configured as a rectilinearly reflecting P-multireflector comprising two single-zoned P-elements of reflection facing each other, wherein antiparallel axial vectors of said P-elements are located in one plane, and wherein said P-multireflector is configured to allow said ions to move along a path whose projection onto a base plane of said P-multireflector comprises a substantially linear segment;

configured as a loop-shaped reflecting P-multireflector configured to allow said ions to move along a path whose projection to a base plane of said P-multireflector is configured as a loop-shaped line, wherein said P-multireflector comprises at least one dual-zoned P-element of reflection.

configured as an arc-wise reflecting P-multireflector configured to allow said ions to move along a path whose projection on a base plane of said P-multireflector is configured as a V-shaped line, and wherein said P-multireflector comprises two end P-elements of reflection arranged at ends of said V-shaped line and a middle P-element of reflection arranged atop said V-shaped line, wherein said middle P-element of reflection comprises a dual-zoned P-element of reflection and said end P-elements of reflection comprise single-zoned P-elements of reflection;

wherein a distance from one of said end P-elements of reflection to said middle P-element of reflection is many times as large as a distance between said two end P-elements of reflection, and wherein a drift space is generated between said end P-elements of reflection and said middle P-element of reflection;

configured as a two-loop-reflecting P-multireflector configured to allow said ions to move along a trajectory whose projection onto a base plane of said P-multireflector is defined by a curved line comprising two loops with one common vertex comprising a nodal point of triangular segments, such that one of four P-elements of reflection are arranged at each outer vertex of each said loop;

wherein its two-loop-wise reflecting types have the width (longitudinal size) $L_Q$-thickness (transverse size) $L_{MRh}$ ratio of the P-multireflector plotted on the projections to its base plane confined within the range $$1.5 \leq \frac{L_Q}{L_{MRh}} \leq 100;$$

and a drift space (field-free space) is generated between the P-elements of reflection within the midway of its length;

wherein said two-loop-reflecting P-multireflector is arranged symmetrically relative to an interloop plane of said generic line and to a geometric mean plane separating heterolooped P-elements of reflection into different sides of said interloop plane;

arranged in incremental mode and comprising at least two extended P-elements of reflection;

wherein linear axes of said at least two extended P-elements of reflection are parallel to each other;

wherein said at least two extended P-elements of reflection comprise two mutually conjugate P-elements, one of which is a Cartesian two-dimensional P-element and the other of which is a three-dimensional P-element;

wherein said at least two extended P-elements of reflection comprise two mutually conjugate P-elements, both of which are three-dimensional P-elements;

further comprising at least one IO element of refraction selected from the group consisting of local IO elements of refraction and extended IO elements of refraction;

wherein said at least one IO element of refraction comprises a local IO element of refraction;

comprising at least two local IO elements of refraction which alternate relative to increments of reflection;

comprising at least two identical local IO elements of refraction configured as sectoral-transbending IO elements;

further comprising an extended IO element of refraction affecting said ion flux along a path of each increment of reflection of said P-multireflector, said extended IO element of refraction being located in a drift space and comprising an extended IO lens element;

arranged in a recurring one-path $R_{iV}^{(m)}$-mode, where i=1 at the first type and i=2 at the second type of the mode and additionally comprises a management subsystem decided-on among the series comprised of its types specified in this invention, wherein the ions flux input and output are performed only on one end side, upper end surface, at (m)=(U), or on the lower end side facing to the upper end side at (m)=(L);

configured to allow ion flux input and output from two different end sides in two-paths using $R_W$-mode;

wherein a unary mode of narrow configuration comprises at least two local P-mirrors;

arranged in a nonclosed two-loop-reflecting mode with an entry-exit of projection-parallel symmetrically non-coplanar type;

wherein all of said at least two local P-mirrors are arranged proximate a base plane of said P-multireflector;

wherein a second of said at least two P-mirrors is arranged in one diagonal segment of a looping line with an entry P-mirror located outside of a base plane of said P-multireflector, and where exit and entry mean planes of said second of said at least two P-mirrors are arranged at acute plane angles within the range larger than zero and less than $$\frac{\pi}{4}$$

relative to said base plane, such that said acute plane angles are equal to each other;

comprising at least four P-mirrors, wherein: exit and entry mean planes of a second and a third of said at least four P-mirrors coincide;

exit and entry mean planes of a first and said second of said at least four P-mirrors intersect at the angle $\bar{\omega}_{12}$, such that an intersection line of said exit and entry mean planes coincides with an averaged vector of a path ion flux at a midway point between said first and said second P-mirrors;

mean planes of a field symmetry of said third and a fourth of said at least four P-mirrors intersect at the angle $\bar{\omega}_{34}$, such that an intersection line of said mean planes coincides with said averaged vector of said path ion flux at a midway point between said third and said fourth P-mirrors such that $\bar{\omega}_{12}=\bar{\omega}_{34}$;

wherein all of said at least two P-mirrors are arranged on a base plane of said P-multireflector, wherein input and output mean planes of said at least two P-mirrors are parallel to each other, and wherein in order to input said ion flux into said P-multireflector and to output said ion flux therefrom, said P-multireflector is configured to allow supply of electric potential in two modes into at least one of said P-mirrors and to provide an additional multifunctional IO element;

wherein at least two of said P-mirrors are mutually conjugate, are arranged in one diagonal segment of said generic line, are configured as dually-zoned P-mirrors, and are configured to allow arrangement of incoming and reflected ion motion paths on different parallel planes;

arranged horizontally continuously and configured to allow arrangement of said averaged vector of said ion flux path along an M-surface of said P-elements;

arranged vertically continuously and configured to allow arrangement of said averaged vector of said ion flux path along a longitudinal-vertical plane of said P-elements;

configured to minimize intercrossing of different branches of said ion flux path;

further comprising an IO element of refraction located in a drift space and selected from a group consisting of P-elements of refraction having rotational symmetry.

To implement the proposed method of mass-spectrometry an IB-channel of a conducting type, comprising one of an IB-channel of an ion conducting block and an ion conducting IB-channel for forming and controlling motion of a channel ion flux comprising at least two boundary surfaces selected from the group consisting of:

(i) at least two boundary surfaces selected from the group consisting of a surface set, a conditionally specified surface, and a surface coinciding with a boundary electrode of an IO channel system, and provided with at least one gate port for passing said channel ion flux consisting of said selected boundary surfaces;

(ii) an IO channel system, wherein said ion conducting IB-channel comprises at least one management subsystem arranged with a curved main axis in at least one of cross-space dispersing mode and multi-reflecting mode.

Main distinction of proposed IB-channel from the known IB-channels consists in that it is configured to be used in at least one of a channel-multipath ion flux including a mode with multi-cell section surfaces, off-axis channel-single-path ion flux, including a mode with double-cell section surfaces; channel-multipath ion flux including a mode with multi-cell section surfaces, off-axis channel-single-path ion flux, including a mode with double-cell section surfaces;

and wherein said IB-channel includes at least one member selected from the group consisting of: an IO elements making it possible to select a specified spatial orientation of said IO element relative to at least one other IO element and relative to a direction of an averaged vector of said ion flux entering said IO element, a flat unary P-multireflector, a three-dimensional P-multireflector, a cascade-multilayered multireflector, an extended P-element of refraction, a three-dimensional P-element of reflection, a P-element of non-uniform height, and a P-element of reflection with a two-dimensional reflection zone.

Other distinctions of the proposed IB-channel from the known IB-channels are:

wherein at least one of said at least two boundary surfaces has a rotational symmetry relative to a straight axis of said IB-channel;

configured to be used in a control mode including one of a single-path mode and a channel-multipath ion flux mode, wherein sections of path components on said at least one of said at least two boundary surfaces are selected from: spheroidal (elliptic) surfaces and ring surfaces, whose centers are arranged at a center of boundary surface rotational symmetry; surfaces of at least one segment of said rings; at least one of said rings; surfaces of rings arranged concentrically and in series relative to said center of boundary surface rotational symmetry; and surfaces comprising no less than two segments of different rings from the said groups of rings;

configured to allow an axis of rotational symmetry of said at least one of said at least two boundary surfaces to cross-over a boundary section of said single-path channel ion flux in $O_O$-crossing mode;

configured to allow arrangement of a boundary section of said single-path channel ion flux to be off-axis of an axis of rotational symmetry of said at least one of said at least two boundary surfaces in $O_E$-crossing mode;

configured to allow arrangement of boundary sections of path components of said multipath channel ion flux to be off-axis of an axis of rotational symmetry of said at least one of said at least two boundary surfaces in $O_{EE}$-crossing mode;

configured to allow an axis of rotational symmetry of said at least one of said at least two boundary surfaces to cross-over a boundary section of one path component of said multipath channel ion flux in $O_{OE}$-crossing mode;

comprising a conducting boundary surface with a mean plane, and configured to be used to control at least one of a single-path and said channel multipath ion flux, wherein sections of path components on said boundary surface are selected from the group consisting of: integral surfaces; surfaces of quadrupole tube sections whose centers are located at a geometric center of said boundary surface; surfaces of at least one segment of said surfaces of quadrupole tube sections; surfaces of quadrupole strips, arranged parallel to a mean plane of said boundary surface; surfaces of sections of quadrupole tube groups whose centers are located at said geometric center of said boundary surface; surfaces including at least two segments of surface sections of different quadrupole tubes in said quadrupole tube groups;

configured to allow said mean plane of said boundary surface to cross-over a boundary section of said single-path channel ion flux in $P_P$-crossing mode;

configured to allow arrangement of a boundary section of said single-path channel ion flux outside said mean plane of said boundary surface in $P_E$-crossing mode;

configured to allow said mean plane of said boundary surface to cross-over said boundary sections of path components of said multipath ion flux in $P_{PP}$-crossing mode;

configured to allow arrangement of said boundary sections of path components of said multipath channel ion flux outside said mean plane of said boundary surface in $P_{EE}$-crossing mode;

configured to allow said mean plane of said boundary surface to cross-over said boundary sections of path components of said multipath channel ion flux in $P_{PE}$-crossing mode;

comprising a doubly symmetrical boundary surface and including two mutually perpendicular planes of symmetry wherein an intersection line of said mutually perpendicular planes comprises a main axis of said boundary surface;

configured to be used to control at least one of a single-path channel ion flux and a multipath channel ion flux, wherein sections of path components on said boundary surface are selected from the group consisting of: integral surfaces and surfaces of quadrupole tube sections whose centers are located at a geometric center of said boundary surface; surfaces including at least one segment of the said surfaces of said quadrupole tube sections; surfaces of quadrupole strips arranged parallel to said mean plane of said boundary surface; surfaces of sections of a quadrupole tube group whose centers are located at said geometric center of said boundary surface; and surfaces including at least two segments of surface sections of different quadrupole tubes in said quadrupole tube group;

configured to allow said main axis of said boundary surface to cross over a boundary section of in $S_O$-crossing mode;

configured to allow at least one of: arrangement of a boundary section of said single-path channel ion flux outside said mean plane of said boundary surface in $S_E$-crossing mode; and said mean plane of said boundary surface to cross over said boundary section of said single-path channel ion flux in $S_P$-crossing mode;

configured to allow said channel ion flux to cross-over said boundary surface in at least one of $S_{PP}$-mode, $S_{EE}$-mode, and $S_{PE}$-mode;

configured to allowing said channel ion flux to cross-over said boundary surface in at least one of $S_{OP}$-mode, $S_{OE}$-mode, and $S_{OPE}$-mode;

wherein a plane of any of said at least two boundary surfaces is approximately perpendicular to said axis of symmetry of a field of respectively adjacent electrodes;

wherein any of said at least two boundary surfaces comprises symmetry which corresponds to field symmetry of an adjacent IO element;

wherein at least one of an input surface and an output surface is located outside of a field of electrodes;

wherein output surfaces are superposed onto a surface of an output electrode;

wherein input surfaces are superposed onto a surface of an input electrode;

wherein said at least two boundary surfaces comprise at least two input surfaces for said channel ion flux to enter into said IB-channel as well as at least one output surface, wherein said output surface confines a limit of channel ion flux transfer, said output surface being selected from the group consisting of surfaces of output to detector elements of a detector system and surfaces for transferring said channel ion flux into other IB-channels;

comprising an IO channel system of a linear type with a straight axis and comprising: a diaphragm-electrode located along a straight axis of a symmetry surface of a first group of input electrodes, a second group of electrodes, and a said output surface, wherein a front side of said output surface of output faces at least one of said input surfaces;

comprising an IO channel system of a reflecting type with a straight axis and comprising: a diaphragm-electrode located along a straight axis of symmetry of an input surface of a first group of electrodes, an output surface comprising a hole on said axis for said channel ions flux to path through in a forward direction, and a second group of electrodes, wherein said second group of electrodes together with said output surface, which faces said second group of electrodes, form a local reflecting IO element;

comprising an IO channel system of a dual-mode type with a straight axis and comprising: a diaphragm-electrode located along a straight axis of symmetry of an input surface, a first group of electrodes, a first surface of output comprising a hole provided on said axis for said channel ions flux to pass through in a forward direction, a second group of electrodes, and a second surface of output, wherein a front side of said first surface of output faces an opposite direction than said input surface, while a front side of said second surface of output faces said surface of input;

having a straight axis of symmetry and comprising a d-type surface of output which confines the limit of channel ion flux transfer to a relevant detector elements as said channel ion flux leaves said IB-channel;

comprising a diaphragm-electrode having a hole therein, wherein configuration of said hole is selected from a group consisting of round, oval, quadrupole, and a configuration in which a geometric center is located on said straight axis of symmetry, and wherein said diaphragm-electrode is configured to allow control of at least one of a size and a configuration of said hole;

configured to vary electric potential in at least one electrode and to control at least one of a cross-space dispersion value by energy and a dispersion value by mass;

comprising an IO channel system with a curved main axis in cross-space dispersing mode, including a management subsystem, at least one cross-space dispersing IO element selected from the group consisting of refracting conic fields, magnetic and/or nonmagnetic conic fields, prismatic conic fields, and V-shaped conic fields;

comprising an IO channel system configured as a management subsystem and configured to transfer said ion flux from a surface of input to a surface of output of said IB-channel;

comprising an IO channel system of single type functional in a multireflecting mode and comprising a P-multireflector;

a conventional end surface said IB-channel and of said P-multireflector is an end surface of said P-multireflector onto which said ion flux enters from an ionic source block, while an opposite end surface is a conventional lower end side of said P-multireflector and of said IB-channel;

wherein its LS-group is performed with additional option feature allowing to use it for transfer the channel ion flux from the P-multireflector, at least, into one of $W_{dm}$ surfaces-d of output (arranged, at least, from one (lower) of side ends at $W_{dm}=W_{dL}$, or from the upper side end at $W_{dm}=W_{dU}$, as leaving the IB-channel), herewith the $W_{dm}$-surfaces-d of output (outputs) confine the limit of channel ion flux transfer to detector group arranged as appropriate;

comprising an IO channel system of cascade-multilayered type functional in a multireflecting mode and comprising at least two P-multireflectors, wherein each P-multireflector constitutes one junction of a $\{P_{\mu(s)}\}$ group and base planes of said P-multireflectors are arranged approximately parallel to each other, and wherein IO subsystems of said cascade-multilayered type IO channel system function in said multireflecting mode are of two categories:

cascade-single-array-multilayered type subsystems functional in a multireflecting mode comprising said P-multireflectors arranged in a single junction; and cascade-multi-train-multijunction type subsystems functional in a multireflecting mode comprising at least two said P-multireflectors of said cascade-single-array-multilayered type and functional in said multireflecting mode;

wherein said at least two P-multireflectors are configured such that ones of said P-multireflectors functional in an increment mode are arranged in a single array while P-multireflectors of a planar type are arranged one above the other, wherein an input end side of said IB-channel and said $\{P_{\mu(s)}\}$-group of cascade-single-array-multilayer type functional in said multireflecting mode comprises a conventional end side onto which said ion flux enters from a side of an ionic source block, while an opposite end side is a conventional lower end side of said IB-channel and of said $\{P_{\mu(s)}\}$-group of cascade-single-array-multilayer type;

comprising a two-loop-wise path type having a four-mirror mode, comprising at least one unclosed layer, and configured to allow receipt of said ion flux from one adjacent layer and to transfer said ion flux backwards into at least one of said adjacent layer and another layer;

wherein said unclosed layer comprises an input-output of a projection-parallel symmetrically hetero-planar mode;

wherein said layers comprise unclosed layers with an input-output of a projection-parallel symmetrically hetero-planar mode and configured to transfer said ion flux from one layer into another;

wherein facing adjacent sides of layers of said $\{P_{\mu(s)}\}$-group are approximately parallel to one another and adjoin one another on at least one side, while upper output end sides of said layers facing away from each other and lower end sides facing away from each other are arranged on a single level;

wherein parts of at least two adjacent electrodes of two adjacent ones of said P-multireflectors associated with two adjacent layers of said $\{P_{\mu(s)}\}$-group are arranged on two sides of one substrate and are arranged symmetrically relative to said substrate;

wherein said $\{A_{m(j)}\}$-subgroup of its LS-group is performed with an additional feature of allowing said sequential passage (transferring) of ions flux through layers of $\{P_{\mu(s)}\}$-group, wherein subscripts s and j, possessing the value within the range 1≤s≤c, 1≤j≤b and b=c−1, confine respectively serial numbers of $P_{\mu(s)}$-layers in the $\{P_{\mu(s)}\}$-group and $A_{m(j)}$-SSTA in the $\{A_{m(j)}\}$-subgroup given (increasing) in direction towards from the input to the output of the IB-channel, wherein: c—overall quantity of layers in the $\{P_{\mu(s)}\}$-group (equal to the number of its last layer); b—overall quantity of SSTA in $\{A_{m(j)}\}$-subgroup (equal to the number of its last SSTA); subscript m assumes two values (m=U, L) and determines the SSTA arrangement from the upper end side (upper SSTA—at m=U), or from the lower end side (lower SSTA—at m=L) of $\{P_{\mu(k)}\}$-group and IB-channel;

wherein said $\{P_{\mu(s)}\}$-group comprises a unilateral layer of recurring $P_{\mu(s)} \equiv P_{iVs}^{(m)}$-mode and additionally comprises a management subsystem, wherein input and output of said ion flux are achieved only from one end side wherein said $\{P_{\mu(s)}\}$-group comprises a layer of $P_{\mu(s)} \equiv P_{Ws}$ two layer through mode, in which at least one of ion flux input and may be achieved from two end sides;

wherein LS-said group is configured to be used for transferring channel ion flux from said $\{P_{\mu(s)}\}$-group to at least one boundary surface of output (arranged on at least one of the lower side at $W_{dm}=W_{dL}$, the upper side at $W_{dm}=W_{dU}$, and the side end as leaving said IB-channel, wherewith said boundary surfaces of output confines a limit of said channel ion flux transferring to detector elements of appropriate arrangement;

wherein said $\{P_{\mu(s)}\}$-group and $\{A_{m(j)}\}$-subgroup are configured to be used in one of a $(P_{\mu(n)}^{(m)} P_{\mu(n+1)}^{(m)})$-mode of transferring said channel ion flux in a forward direction to said $\{P_{\mu(s)}\}$-group and a mode of transferring said channel ion flux from one layer $P_{\mu(n)}^{(m)}$ to a following adjacent layer $P_{\mu(n+1)}^{(m)}$;

characterized in that it comprises the $\{P_{\mu(s)}\} \equiv \{P_{iVs}^{(U)}\}$-group, constituted of layers of $P_{iVs}=P_{iVs}^{(U)}$-type as well as of $\{A_{m(j)}\} \equiv \{A_{Uj}\}$-subgroup constituted of the SSTA of $A_{Uj}$-type, single-side type of upper arrangement;

configured to turn-on a mode of transferring the $\{P_{\mu(a)}^{(m)} P_{\mu(b)}^{(m)}\}$ said channel ion flux from one layer to another layer preceding said one layer (a f b) and a mode of remote transferring (a f b+1) of said channel ions flux from a last layer of said $\{P_{\mu(s)}\}$-group into a first layer of said $\{P_{\mu(s)}\}$-group for repeated traversal through layers of said $\{P_{\mu(s)}\}$-group;

wherein at least one of its said SSTO and SSTA is performed with option feature to use it in retransferring mode;

further comprising additionally the upper SSTO, performed with option feature to use it in retransferring mode;

wherein, at least, one of said mentioned SSTO, SSTA and additional upper SSTO is performed with option feature allowing to retransferring, between the upper end sides of the layers of the $\{P_{\mu(s)}\}$-group;

configured to be used in a running multicyclic mode and comprising a $\{P_{Ws}\}$-group with even-numbered layers and the $\{A_{mbj}\}$-subgroup;

comprising, at at least one side of an operating zone of one of said P-multireflectors one of a surface of input and a surface of output;

wherein a portion thereof is configured to allow transferring of said channel ions flux towards said surface of output of said IB-channel from outside a surface of an ion flux section within said operating zone of said one of said P-multireflectors;

wherein said portion is configured to allow transferring of said channel ion flux between any of said surface-sections within operating zones of two of said P-multireflectors;

wherein said portion is configured to allow transferring of said channel ion flux between two of said P-multireflectors along projective-parallel symmetrically heteroplane directions of said channel ions flux, wherein a transferring subsystem which transfers said channel ion flux is configured as a management subsystem provided with an input-output in projective-parallel symmetrically heteroplane mode;

wherein said portion is configured to allow transferring of said channel ion flux by frontal components of typical lines of two P-multireflectors of two-loop-reflecting type;

wherein said portion is configured to allow transferring of said channel ion flux along projective-parallel diagonal segments of generic lines of two-loop-wise reflecting P-multireflectors;

wherein said portion is configured to allow transferring of said channel ion flux between two layers of said $\{P_{\mu(s)}\}$-group, along antiparallel, single-plane directions of said channel ions flux, wherein a transferring subsystem for transferring said channel ions flux is configured as a management subsystem of single plane mode with antiparallel input-output;

wherein said portion is configured to transfer said channel ion flux along frontal segments of generic lines of two-loop-wise reflecting P-multireflectors;

wherein said portion is configured to transfer said channel ion flux along diagonal segments of generic lines of two-loop-wise reflecting P-multireflectors;

wherein said portion is configured to transfer said channel ion flux within operating zones of two layers of said $\{P_{\mu(s)}\}$-group along directions of single-planes intersecting at an angle of said channel ion flux;

wherein a transferring subsystem for transferring said channel ion flux is configured as a management subsystem of single plane and single reflecting mode;

wherein a transferring subsystem for transferring said channel ion flux is configured as a management subsystem of single plane and doubly reflecting mode;

wherein a portion thereof is configured to equalize an ion flight time on upper and lower trajectories of said path ion flux arranged in ion packages;

wherein at least one electrode of at least one extended P-element of reflection is configured to supply pulsating voltage to said at least one P-element of reflection to implement at least one of ion input into said P-multireflector and ion output from said P-multireflector;

configured to control space focusing of ion flux along a direction of ion motion in said path ion flux;

wherein at least one electrode of at least one extended reflection P-element is configured to supply pulsating voltage to said at least one extended reflection P-element to control space focusing of ion flux along a direction of said path ion flux.

To implement the proposed method of mass-spectrometry a spectrometer (MS) is used comprising:

(i) MS-blocks including: an ionic source block, a group of ion conducting blocks, comprising a block-structured docking group, and an analyzing-dispersing block, wherein all said blocks comprise IB-channels with boundary surfaces and IO channel systems, wherein each said IB-channel associated with one of said blocks is a part of an MS-channel with an MS-channel IO system comprising ion conducting IB-channels of ion conducting blocks in complex with an ion source IB-channel of an ion source block, and wherein said IO channel system of said ion-conducting IB-channel function as one of: a management subsystem, a subsystem with a curved main axis in a cross-space dispersing mode, a subsystem with a curved main axis, in a multi-reflecting mode, (ii) a detector system, (iii) a control-computer system;

Main distinction of proposed MS from the known MS devices consists in that it is performed with option feature allowing to use it in channel-multipath ion flux mode with multi-cell section surfaces, and an off-axis single-path channel ion flux mode with double-cell section connected surfaces;

comprising at least one of an IO element enabling selection of a specified spatial orientation of said IO element relative to at least one other IO element and relative to a direction of an averaged vector of said ion flux entering said IO element, a flat unary P-multireflector, a three-dimensional P-multireflector, a cascade-multilayered multireflector, an extended P-element of refraction, a three-dimensional P-element of reflection, a P-element of non-uniform height, and a P-element of reflection with a two-dimensional reflection zone.

Other distinctions of proposed MS from the known MS devices consist in the following:

wherein said block-structured docking group comprising at least a preshaping block and a distributing-accelerating block group;

wherein said MS-block comprises at least one IB channel configured in a mode selected from a group consisting of: channel-single-path mode, and channel multipath mode and wherein at least one MS-channel is configured to allow said path ion flux to pass from said ions source to at least one d-surface defining a limit of channel ion flux transfer with respect to a detector element of said detector system;

wherein at least one of its ion-conducting IB-channels is decided-on among the series comprising its said types;

wherein each said path ion flux corresponds to one individual detector in a detecting element of said detector system;

wherein when configured in channel multipath mode, said ion paths are configured to be used in at least one mode of independently of one another and alternatively in a specified time frame;

configured in channel multipath modes, wherein each pair of said IB-channels in each said block is configured as at least one of a bound pair and a separate pair;

wherein, when configured in multichannel mode, said ion channels are configured to be used in at least one mode of independently of one another and in a specified time frame;

wherein each said output gate of said surface-electrode of a preceding said IB-channel is an output gate of a subsequent said IB-channel;

wherein a reverse side of an output electrode surface of said preceding IB-channel is an input electrode surface of a next nearest IB-channel;

configured in module-block-structured mode and configured to allow a simplified arrangement of modular equipment and reconfiguration of block patterns of said MS thereby providing a wide variety of modularity limits and resolution powers;

wherein said ionic source IB-channel comprises at least one ion source each said ion source being adjacent to one output aperture of said ionic source, selected from the group consisting of: holes; screening tubes with skimmers; screening tubes without skimmers; and devices for preliminary forming of at least one path ion flux, wherein quantity number, configuration, and arrangement of holes of said devices conform to boundary surfaces of an adjacent said ion-conducting IB-channel;

wherein said ionic source IB-channel additionally comprises a transient controlling source unit comprising at least one electrode with output surfaces for transferring said path ion flux;

wherein the ions source of ionic source IB-channel is decided-on among the series comprising any ionic source providing forming of ion flux, e.g., electronic ionization (EI), chemical ionization (CI), electron capture (EC), electric field ionization (FI), ionization with heat spray, ionization under atmospheric pressure, electrospray, ionization under atmospheric pressure (APESI), chemical ionization under atmospheric pressure (APCI), photoionization under atmospheric pressure (APPI), inward laser desorption: mass-spectrometry, matrix-activated laser desorption/ionization (MALDI), gas-filled MALDI, atmospheric MALDI, bombardment by fast atoms (FAB), field desorption— desorption in electric field (FD, plasma desorption (PD), ionization in inductively coupled plasma (ICP), thermal ionization, glow discharge ionization and spark ionization, plasma and glow discharge ionization, corona discharge and ionization in process of laser ablation;

wherein said ionic source IB-channel is configured to allow forming of ion flow exiting said ionic source IB-channel in at least one of a pulsed flow of ions packages and a continuous ion flow;

wherein said block-structured docking group comprises a block-structured docking group adjacent said ionic source block comprising at least one parallel pre-shaping IB-channel, which pre-shaping IB-channel comprises at least one structural elements configured to allow intermediate configuration, acceleration, and control of ion flux forming;

wherein said pre-shaping IB-channel comprises at least one section selected from a group consisting of: ion pre-traps; flux drift tubes of asymmetrical cells of ion mobility, DC/field comprising input and output gates with ion gate valves; refracting P-elements; and diaphragms-apertures;

wherein said ion pre-trap is configured to:
select certain quantities of ions generated by said ionic source IB-channel;
to store said quantities of ions; and
to output said store ions from said ion pre-trap and input said stored ions into at least one subsequent said MS block;
wherein said ion pre-trap is selected from a group consisting of a controlling electrode group with an electric field, a short unit of guiding quadrupole, and a diaphragm-aperture;

wherein said block-structured docking group additionally comprises a distributing-accelerating block arranged behind a performing block which comprises at least one distributing-accelerating IB-channel, wherein one of said distributing-accelerating block and said distributing-accelerating IB-channel comprises at least one pre-analyzing-guiding accelerator configured to allow guiding of said ion flux towards an analyzing-dispersing IB-channel which comprises at least two accelerating electrodes with at least, one output gate;

wherein said at least one output gate of said pre-analyzing-guiding accelerator is covered with a fine mesh;

configured to confine an angle $\beta_{(12)1}$ defined between output directions of said ion flux from the said ionic source IB-channel and from said pre-analyzing-guiding accelerator within the range of $$0 \le \beta_{(12)1} \le \frac{\pi}{2},$$

and wherein said pre-analyzing-guiding accelerator is arranged radially with radial ion output when $\beta_{(12)1} \approx 0$ and is arranged orthogonally when $$\beta_{(12)1} \approx \frac{\pi}{2};$$

wherein said distributing-accelerating IB-channel is configured to form a pulse ion flux as said ion flux passes through said pre-analyzing-guiding accelerator;

wherein said distributing-accelerating IB-channel comprises two segments, wherein one of said two segments is configured to use an alternating voltage while another of said two segments is configured to use a static voltage;

wherein said distributing-accelerating IB-channel is configured to form thin ions packages appropriate for time-of-flight mass-analysis of said ion flux as said ion flux passes through said pre-analyzing-guiding accelerator;

wherein its distributing-accelerating IB-channel is performed with option feature allowing an orthogonal ions output $$\left(\text{at } \beta_{(12)1} \approx \frac{\pi}{2}\right)$$

its accumulation area is performed as a monofield generating a quadratic electrostatic field, while the edge of earthed electrode of the said monofield is coupled to the earthed fluxgate electrode (mesh) within the area of ions acceleration (palser) with uniform field;

wherein said distributing-accelerating IB-channels are configured as static and are configured to allow forming of a continuous ion flux as said ion flux is output from said pre-analyzing-guiding accelerator;

wherein said distributing-accelerating IB-channel additionally comprises a pre-analyzing ions accumulator, arranged ahead of said pre-analyzing guiding accelerator and serially connected to said pre-analyzing guiding accelerator, where said pre-analyzing ion accumulator is configured to allow receipt, accumulation, and intermittent emission of said ions in at least one of radial, axial, and orthogonal directions through said apertures;

wherein said pre-analyzing ion accumulator is selected from a group consisting of a linear RF-only IC and a curved quadrupole;

wherein its detector group comprises one or more ions detector with entrance gate arranged on the surface of d-entry, where each path ion flux corresponds, to an individual ion detector of detector element decided-on among the terms series comprising: Faraday cylinder; secondary electron multiplier with at least one dynode; scintillator and photomultiplier; microchannel; microsphere board; at least two slots of detection; at least two anodes;

wherein, at least, one ions detector of detecting group is provided with ions separator of certain transmission band and comprises, at least, one of series terms comprising control grids, logical Bradbury-Nielsen terms, plane-parallel deflector (condenser);

wherein each ions detector is connected to the system of data acquisition and data-storage provided with analog-to-digital converter (adaptive data compression protocol);

wherein at least one ion detector is configured within said MS;

wherein said ion detector is configured to allow extension of a dynamic range of said MS through alternative scanning associated with varied intensity of voltage of at least one of a pulsating ionic source and said distributing-accelerating IB-channel;

wherein said ion detector is configured to extend a dynamic range of said MS through alternative scanning in varying durations of ion injections into an output gate of said ion source;

wherein said ion detector is configured to allow automatic gain control;

wherein its analyzing-dispersing block comprises at least, one analyzing-dispersing IB-channel, decided-on among the series comprising the following: toroidal and cylindrical sectoral electrical analyzers; sectoral magnetic analyzers; orbitrap analyzer; Fourier analyzer ICR; static analyzer, e.g., the IO channel system of IB-channel is performed with curved main axis in cross-space dispersing mode; the time-of-flight (TOF IB-channel) analyzer and its IO channel system are performed in one of said modes;

further comprising a detecting group arranged on at least side adjacent said analyzing-dispersing IB-channel, wherein said detecting group comprising multiple ion detectors of different types;

wherein its block-structured docking group additionally includes an block of fragmentation cell comprising at least, one IB-channel of fragmentation cell-set filled with gas and provided with differential pumping cascades wherein each fragmentation cell is provided at least, with two apertures to access the path ion flux into the fragmentation cell and to exit from it;

wherein each its path ions flux corresponds to one individual fragmentation cell (section of fragmentation cells);

wherein at least one fragmentation cell is performed with option feature to using it in two modes: passage of ions through fragmentation cell without substantial atomization or with ions atomization (fragmentation) within fragmentation cell (inside of fragmentation cell);

wherein said block-structured docking group additionally includes one ion selecting block comprising at least one IB-channel of ion selection, configured to allow sequential reduction of the range of ion mass selection through at least one ion selecting step;

wherein said IB-channel of ion selection is selected from a group consisting of: a quadrupole IB-channel; an ion trap; a static IB-channel; and a TOF IB-channel analyzer;

comprising a detecting group arranged at least on one side of said IB-channel of ion selection;

wherein at least one of said analyzing-dispersing IB-channels and said IB-channel of ion selection comprises means of adjusting a path length and a voltage of ion acceleration;

wherein said analyzing-dispersing IB-channel is configured to allow at least one of said ion path length and said voltage to be less than a value for said IB-channel of ion selection;

wherein said MS-channel is configured to allow ion time-of-flight through said IB-channel of ion selection to be at least three times as large as ion time-of-flight through said analyzing-dispersing IB-channel;

wherein at least one of said IB-channel of ion selection and said analyzing-dispersing IB-channel is nonmagnetic;

wherein said IB-channel of ion selection is configured as a time-of-flight IB-channel and said IO channel system is configured in multireflecting mode and selected from the group consisting of: single, single-train-multilayer and multi-row-multilayer modes;

wherein said analyzing-dispersing IB-channel is configured as a time-of-flight IB-channel with straight axes;

wherein said block-structured docking group additionally comprises blocks of ion super accumulation, comprising at least one IB-channel of ions super accumulation, configured to allow selection of the ion subsets or at least some of their derivatives;

wherein said ions super-accumulation IB-channel is selected from the group consisting of linear RF-only IC and curved quadrupole;

wherein at least one said MS-channel is configured to allow implementation of a series of steps for ion flux advancement:

(ab) inject said path ion flux via an IB-channel of said ionic source into a pre-shaping IB-channel;

(bc) eject said path ion flux from said pre-shaping IB-channel and inject said path ion flux into a distributing-accelerating IB-channel;

(cd) eject said path ion flux from said distributing-accelerating IB-channel, inject said path ion flux into said ion selecting IB-channel, and register said path ion flux in at least one detector group at said ion selecting IB-channel;

(de) eject said path ion flux from said ion selecting IB-channel and inject it into a fragmentation cell;

select from the series comprising {(ec) and (ef)}: eject the path ion flux from the cell of fragmentation and inject it depending on the path ion flux composition after the effect of the cell of fragmentation on the ion flux at appropriate option into one of channels: distributing-accelerating IB-channel; IB-channel of ions super accumulation and storage of taken-off ions masses;

(Q11) at least, one cycle comprising series steps such as (cd), (de) and {(ec) or (ef)} to accumulate ions of specified masses in the IB-channel of ions super accumulation;

select from the series comprising (fc) and {(fe) and further (ec)}: (fc)—eject the path ion flux from the IB-channel of ions super accumulation and inject it into the distributing-accelerating IB-channel; {(fe)}: eject the path ion flux from the IB-channel ions super accumulation and inject it into cell of fragmentation; and further {(ec)}: eject the path ion flux from the cell of fragmentation and inject it into distributing-accelerating IB-channel;

(Q12) at least, one cycle comprising (Q11) with subsequent selection from (fc) and {(fe) and further (ec)};

(cg) eject the path ion flux from the distributing-accelerating IB-channel and inject it into the analyzing-dispersing IB-channel, as well register the path ion flux at least in one detector group of analyzing-dispersing IB-channel;

at the option, depending on results of step (cg) realization, implement the steps of channel ions flux transfer by means of two of groups of steps: (Q13), at least, one cycle comprising single-stepping implementation of all steps of path ion flux advance as it is specified in (ab)-(cg) mentioned in this claim; select from the series comprising (ge), {(gc) and further (ce)}: eject the path ion flux from the analyzing-dispersing IB-channel and inject it, conforming to appropriate option, into one of channels: into the fragmentation cells; {(eject the path ion flux from the analyzing-dispersing IB-channel inject it into the distributing-accelerating IB-channel) and further (eject the path ion flux from the distributing-accelerating IB-channel and inject it into fragmentation cells)};

(Q14) at least, one cycle comprising implementation of all steps: beginning by the step selected from the group consisting of {(ec), (ef)} and finishing by (cg) step as it is specified in this claim;

wherein at least one MS-channel is performed with option feature allowing sequential steps to transferring channel ions flux (second version of extended-multiblock mode):

(ab); (bc); (cd); (de);

decided-on among the group of {(ec), (ef)};

(Q11);

decided-on among the group of (fc) and {(fe) and further (ec)};

(cg);

at the option, depending on results of step (cg) realization implement the steps of channel ions flux transfer by means of one of two groups of steps: (Q23) at least, one cycle comprising sequential implementation of all steps (ab)-(cg) as said in this claim; selection from the series comprising (ge) and {(gc) and further (ce)};

(Q24) at least, one cycles comprising sequential implementation of all steps: beginning from decided-on among the group of {(ec) or (ef)} to (cg) as said in this claim;

wherein at least one MS-channel is performed with option feature allowing sequential steps in transferring channel ions flux by-passing the IB-channel of ions super-accumulation, failing the latter, inclusive (multiblock mode of operation):

(ab); (bc); (cd); (de); (ec);

(Q31) at least, one cycle comprising increments as steps follows: (cd), (de) and (ec);

(cg);

at the option, depending on results of step (cg) realization implement the steps of channel ions flux transfer by means of one of two groups of steps: (Q33) at least, one cycle comprising sequential implementation of all steps (ab)-(cg) as said in this claim; select from the series comprising (ge) and {(gc) and further (ce)};

(Q34) at least, one cycle comprising sequential implementation of all steps beginning from (ec) to (cg) as it is specified in this claim;

wherein at least, one MS-channel is performed with option features allowing to implement series steps of path ion flux advance by-passing the IB-channel of ions super accumulation and IB-channel of ions selecting, failing all last mentioned IB-channel inclusive (mean modularity level of operation without ions selecting):

(ab); (bc); (cg); (ge) or {(gc) and further (ce)}; (ec); (cg);

at the option, perform the series steps of path ion flux advance depending on results of (cg) step implementation:

at the option, depending on results of step (cg) completion implement the steps of channel ions flux transfer by means of one of two (Q43), (Q44) groups of steps:

(Q43) at least, one cycle comprising implementation of all steps beginning from (ab) to the last (cg) step mentioned in this claim;

(Q44) at least, one cycle comprising implementation of all steps (ec); (cg) decided-on among the group of (ge) and {(gc) and further (ce)} mentioned in this claim;

wherein at least one MS-channel is performed with option feature allowing a sequential implementation of all steps to transferring the channel ions flux by-passing the IB-channels of ions super-accumulation and the IB-channel of fragmentation cell, failing all last mentioned IB-channels inclusive (mean modularity level of operation without ions fragmentation):

(ab); (bc); (cd);

(dc) output the channel ions flux from the ions selecting IB-channel and input it into distributing-accelerating IB-channel;

(Q51) at least, one cycle comprising implementation of all steps (cd) and (dc);

(cg);

wherein at least one MS-channel is performed with option feature allowing sequential implementation of all steps to transferring the channel ions flux by-passing the IB-channel of ions super-accumulation, IB-channel of ions selecting and IB-channel of fragmentation cell, failing all last mentioned IB-channels inclusive (small modularity regime of operation): (ab); (bc); (cg);

wherein when it is performed as a time-of-flight analyzing-dispersing IB-channel it comprises a data transmitting and data processing system providing parallel reception of child fragments spectra without intermixing the ions spectra representing the primary materials

BRIEF DESCRIPTION OF THE DRAWINGS

This invention may be implemented in many versions, so only certain preferred implementations are described by means of examples given in the supporting drawings. As an example, explaining versions of the proposed engineering solutions are schematically illustrated by the figures, in which:

FIGS. 5-19 represent the surfaces of ion-source IB channel output;

FIGS. 20-129 represent versions of the proposed IO elements;

FIGS. 130-134 represent diagrams of IO arrangement versions including straight axis TOF IB-channels useful in an analyzing-dispersing block;

FIGS. 233-257 represent diagrams of IO multilayer multi-reflecting arrangements useful with TOF IB-channels;

DETAILED DESCRIPTION OF EMBODIMENTS OF THE DISCLOSED TECHNOLOGY

Figure 1:
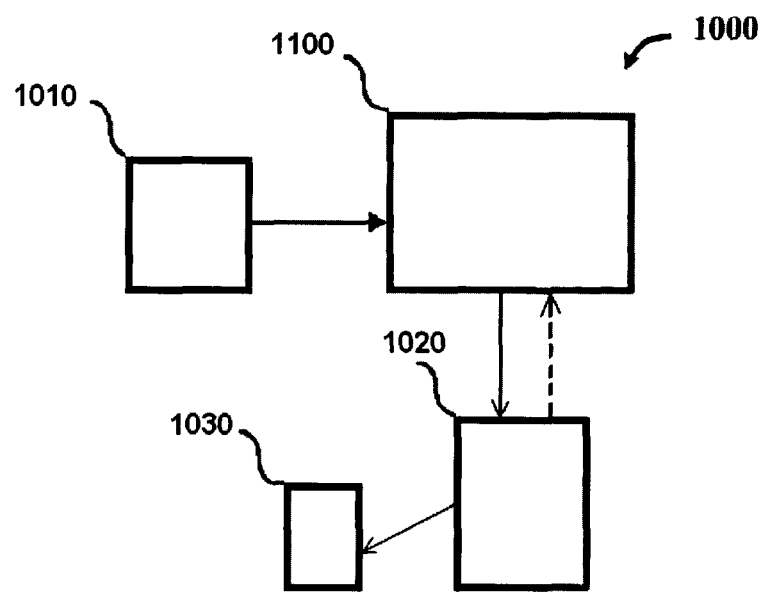
FIGS. 1-4 represent schematic diagrams of MS arrangement versions.
Figure 2:
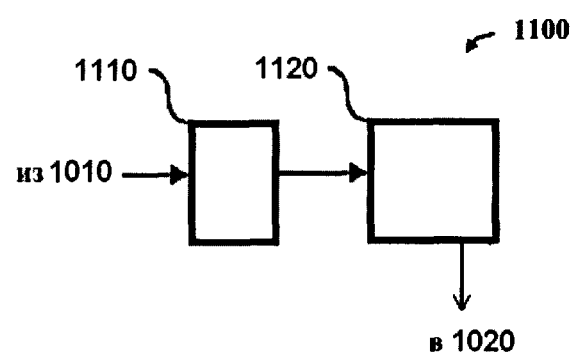
Figure 3:
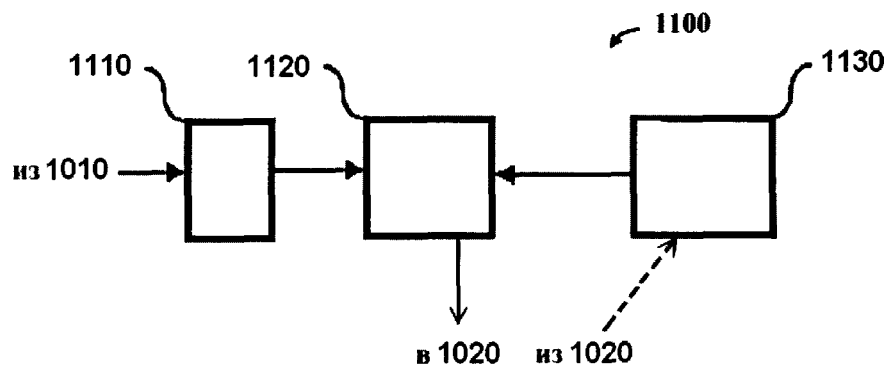
Figure 4:
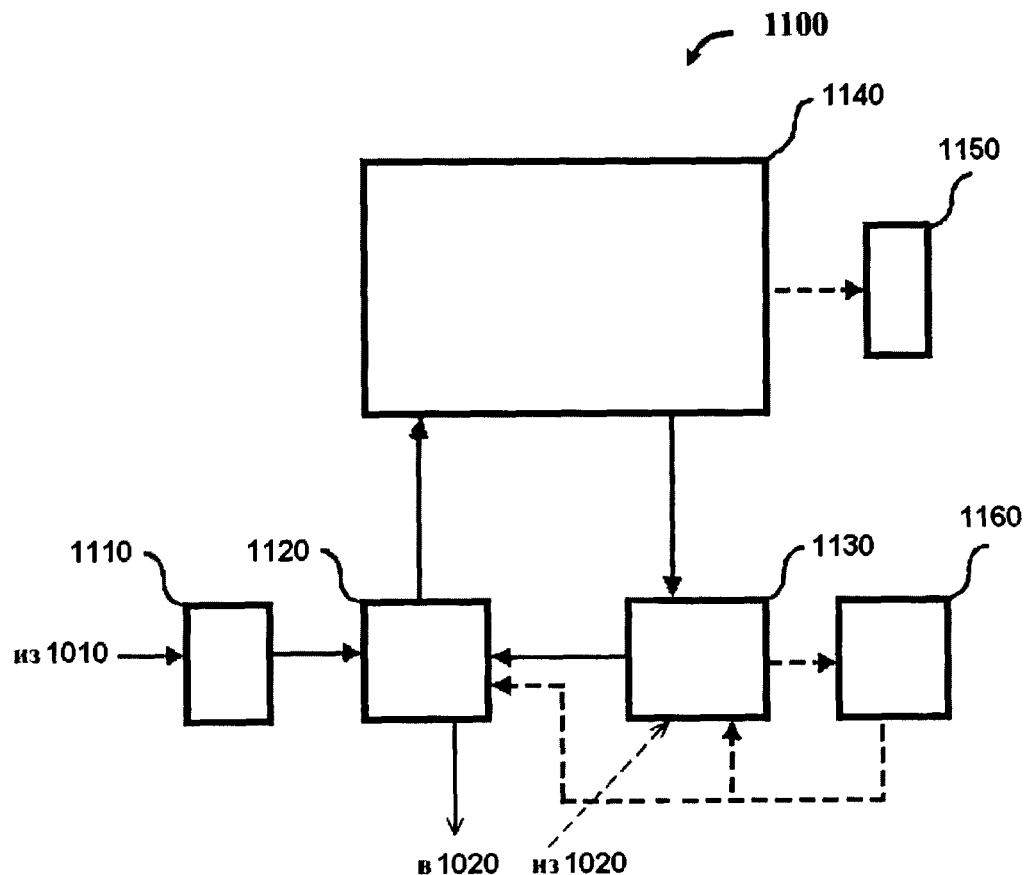

FIGS. 1-4 show a mass-spectrometer as a complex comprising several blocks, where characteristic ions paths between the IO blocks are shown by leaders or dashed arrowhead lines. The MS additionally comprises a controller-computer block (not shown in the figures) to control and manage operation of all spectrometer blocks, as well as to assure information acquisition and processing. FIG. 1 shows a general block diagram of the MS 1000, wherein ion flux from an ion source block 1010 enters into a block-structured docking group 1100. Ion source block 1010 comprises one or more chambers of ionization and systems of samples ionization. Ion flux delivered from block-structured docking group 1100 enters into an analyzing-dispersing block 1020. FIGS. 1 to 4 show the analyzing-dispersing block 1020 as being of open type and ion flux may flow backward from the analyzing-dispersing block 1020 into the block-structured docking group 1100 and/or into a detector section 1030 provided in the analyzing-dispersing block (in an analyzing-dispersing IB-channel). In cases where the analyzing-dispersing block 1020 uses a single-input mode (e.g., analyzing-dispersing block 1020 uses Fourier-analyzing mode), the detector sections 1030 are not provided in the analyzing-dispersing block. FIG. 2 shows a block diagram of block-structured docking group 1100 comprising a minimal number (two) of blocks (small-modular version) which comprises a pre-shaping block 1110 and distributing-accelerating block 1120. The MS performed with block-structured docking group 1100 makes it possible to carry out only single-stage mass-spectrometry. FIG. 3 shows a block diagram of an embodiment of block-structured docking group 1100 comprising three blocks, as in the mean-modality version of MS, including pre-shaping block 1110, distributing-accelerating block 1120, and block of milling cell 1130. The MS comprising block-structured docking group 1100 makes it possible to carry out a structure analysis. FIG. 4 shows a block diagram of an embodiment of block-structured docking group 1100 comprising five blocks, as in the extended multi-module version of MS, including pre-shaping block 1110, distributing-accelerating block 1120, milling cell block 1130, a block of ion take-off 1140, detector sections 1150 in the block (in IB-channels) of ion take-off, and a block of ion super-accumulation 1160. In FIG. 4, ion super-accumulation block 1160 may be omitted, and the block diagram of block-structured docking group 1100 would include four blocks, as in the multi-module version of MS. The MS configured in the extended multi-module version or multi-module version of block-structured docking group 1100 makes it possible to carry out the structure analysis in MS<n> mode. Diagrams of boundary sections of path components of channel ion flux are shown in FIGS. 5 to 19 by shaded areas as projections on the planes of boundary surfaces 10A, 10B, 10C, 10D, 10E, 10F, 20A, 20B, 20C, 20D, 20E, 20F 20G, 20H and 20Q perpendicular to the direction of ion flux motion. These examples explain the proposed engineering solution of a boundary surface of an IB-channel: FIGS. 5 to 10 show different versions of boundary sections of path channel ion fluxes on boundary surfaces of an IB-channel with rotational symmetry; FIGS. 11 to 19 show different versions of boundary sections of path channel ion fluxes on doubly symmetric boundary surfaces of an IB-channel.

In FIGS. 5 to 19, the axial point and the geometric center point of each boundary surface of the IB-channel (of each figure) correspond to the points of intersection with coordinate axes x and y.

Figure 5:
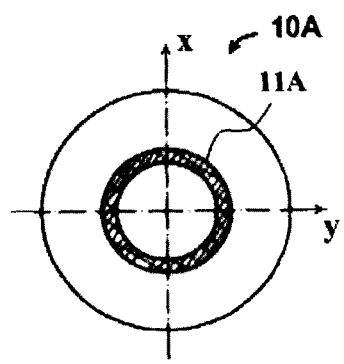

In FIGS. 5 and 11 the boundary sections of channel ion fluxes have off-axis single-path (single-flow) modes (also considered to be off-axis single-path-channel ion flux channels with doubly connected surfaces of section). In other figures the boundary sections of path channel ion fluxes have multipath (parallel-multithread) modes wherein each boundary surface comprises two or more boundary sections of path channel ion flux closely located to the axis or plane of symmetry.

Figure 6:
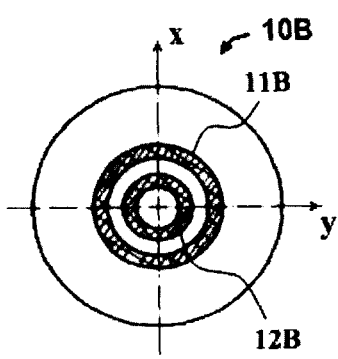
Figure 7:
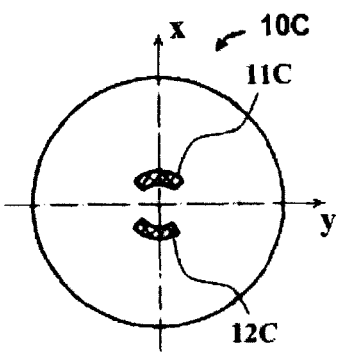

In FIGS. 5 to 10, configurations of boundary sections of path channel ion fluxes are selected from a group comprising: a round (oval) surface and a surface of a ring whose centers are located at the center of rotational symmetry of the boundary surface; surfaces of one or more such rings; surfaces of a ring group, located concentric and in series relatively to the center of rotational symmetry of the boundary surface; and surfaces of parts of different rings in the group. FIG. 5 shows a boundary surface 10A configured in off-axis single-flow mode ($O_E$-type of intercrossing), comprising a boundary section of a single-path channel ion flux in the form of a ring 11A, whose center is located at the center of rotational symmetry of the boundary surface. FIG. 6 shows a boundary surface 10B configured in off-axis single-flow mode ($O_{EE}$-type of intercrossing) comprising boundary sections of a multipath channel ion flux in the form of circular rings 11B and 12B, located concentrically relative to the center of rotational symmetry of the boundary surface. This multipath (two-path) channel ion flux has multiply connected (triply connected) surfaces of sections. FIG. 7 shows a boundary surface 10C, comprising boundary sections of a multipath channel ion flux in the form of two parts 11C and 12C of a circular ring whose center is located at the center of rotational symmetry of the boundary surface. FIG. 8 shows a boundary surface 10D, comprising boundary sections of a multipath channel ion flux in the form of four parts 11D, 12D, 13D, and 14D of two circular rings located concentrically relative to the center of rotational symmetry of the boundary surface. FIG. 9 shows a boundary surface 10E, comprising boundary sections of a multipath channel ion flux in the form of four parts 11D, 12D, 13D, and 14D of one circular ring, whose center is located at the center of rotational symmetry of the boundary surface. FIG. 10 shows a boundary surface 10F, comprising boundary sections of a multipath channel ion flux in the form of eight parts 11F, 12F, 13F, 14F, 15F, 16F, 17F and 18F of two circular rings located concentrically relative to the center of rotational symmetry of the boundary surface.

Figures 20, 21, 22, 23, 24, 25:
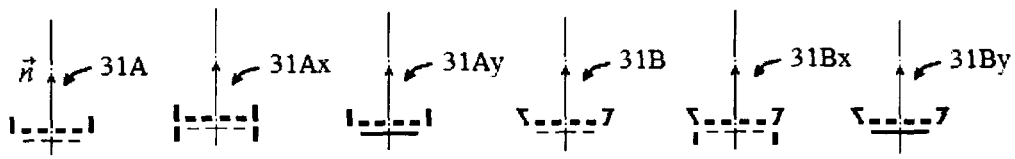
Figures 26, 27, 28, 29, 30, 31:
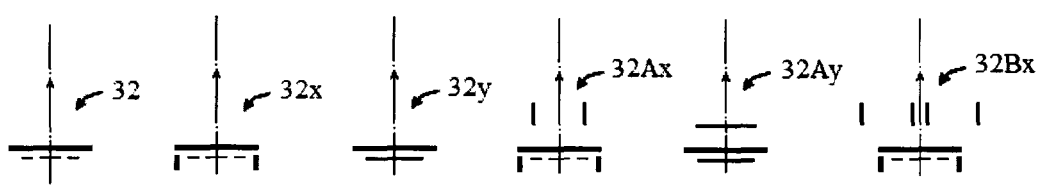
Figures 32, 33, 34, 35, 36:
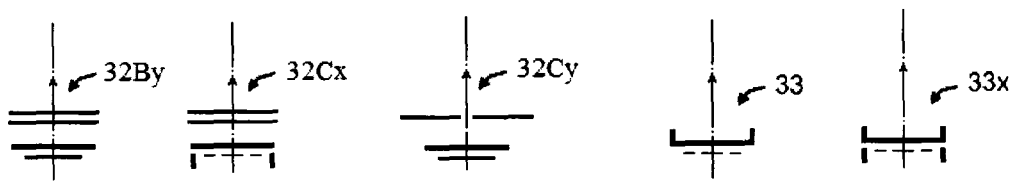
Figures 37, 38, 39, 40, 41, 42:
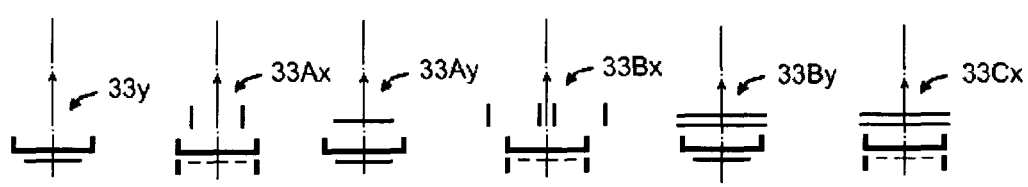
Figures 43, 44, 45, 46, 47:
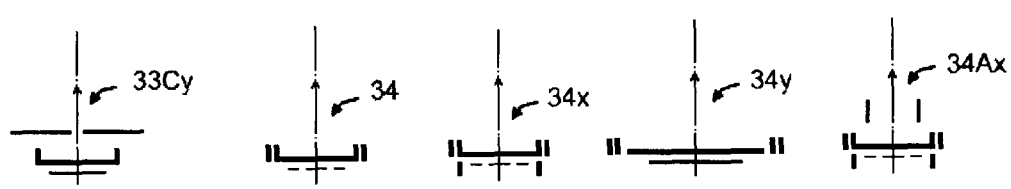

In FIGS. 11 to 19 configurations of boundary sections of path channel ion fluxes are selected from a group including: integrated surfaces and surfaces of quadrangular tube sections (especially with rounded corners) whose centers are located on the geometric center of the boundary surface; surfaces of one or more parts of the surfaces of quadrangular tube sections; surfaces of quadrangular strips (including strips with rounded corners), located mainly parallel to the mean plane of the boundary surface; surfaces of sections of a group of quadrangular tubes (especially with rounded corners), whose centers are located on the geometric center of the boundary surface; and surfaces of section parts of different quadrangular tubes of the group of quadrangular tubes. FIG. 11 shows a boundary surface 20A configured in off-axis single-flow mode ($S_O$-type of intercrossing), comprising a boundary section of a single-path channel ion flux in the form of surfaces of a section of a quadrangular tube 11A, whose center is located at the center of rotational symmetry of boundary surface. FIGS. 12 to 16 show, respectively, boundary surfaces 20B, 20C, 20D, 20E and 20F, whose boundary sections are located off-axis of the boundary surfaces axis of symmetry such that boundary sections intercross with the mean plane of the input surface ($S_{PP}$-type of intercrossing, boundary surface 20B is given as illustrative example), or they are located outward of the mean plane of the boundary surface ($S_{EE}$-type of intercrossing, boundary surfaces 20C, 20D and 20E are given as illustrative examples), or several of them are located outward of the mean plane of the input surface ($S_{PE}$-type of intercrossing, boundary surface 20F is given as illustrative example). FIG. 12 shows a boundary surface 20B, comprising boundary sections of a multipath channel ions flux in the form of section surfaces of two quadrangular tubes 21B and 22B, whose centers are located on the geometric center of the boundary surface. FIG. 13 shows a boundary surface 20C, comprising boundary sections of a multipath channel ions flux in the form of two quadrangular strips 21C and 22C, parallel to the mean plane of the boundary surface. FIG. 14 shows a boundary surface 20D, comprising boundary sections of a multipath channel ions flux in the form of four quadrangular strips 21D, 22D, 23D and 24D, parallel to the mean plane of boundary surface. FIG. 15 shows a boundary surface 20E, comprising boundary sections of a multipath channel ions flux in the form of four circles 21E, 22E, 23E, and 24E, symmetrically positioned relatively to two orthogonal planes xz and yz. FIG. 16 shows a boundary surface 20F, comprising boundary sections of a multipath channel ions flux in the form of eight quadrangular strips 21F, 22F, 23F, 24F, 25F, 26F, 27F and 28F, configured as eight parts of a quadrangular tube section surface whose center is located at the geometric center of the boundary surface. FIGS. 17, 18, and 19 show, respectively, boundary surfaces 20G, 20H and 20Q, in which one boundary section intercrosses with the geometric center of the boundary surface while all other boundary sections intercross with the mean plane of the boundary surface ($S_{OP}$-type of intercrossing, boundary surface 20G is given as illustrative example), or they are located outward of the mean plane of input surfaces ($S_{OE}$-type of intercrossing, boundary surfaces 20H and 20Q are given as illustrative examples). FIG. 17 shows a boundary surface 20G, comprising boundary sections of a multipath channel ions flux in two modes 21G and 22G, wherein mode 21G is configured as a quadrangular tube section surface, while mode 22G is configured as a quadrangular strip, whose centers are located on the geometric center of the boundary surface. FIG. 18 shows a boundary surface 20H, comprising boundary sections of a multipath channel ions flux in modes 21H, 22H, and 23H, configured as three quadrangular strips parallel to the mean plane of the output surfaces. FIG. 19 shows a boundary surface 20Q, comprising five output gates 21Q, 22Q, 23Q, 24Q and 25Q, configured in the form of five quadrangular strips. FIGS. 20 to 129 show IO elements in the form of conventional symbols (31A, 31Ax, . . . 47By), among them P-elements (IO elements with M-surface) proposed to be included in the MS, such that in each IO element a unitary axial front vector (unitary vector) is shown by leader (as example, the axial front vector $\vec{n}$ in the IO element is designated by symbol 31A) of the IO element. Additionally, each symbol is shown in projections on xz and yz planes of a Cartesian coordinate system integrated respectively by the vertical plane and the horizontal (mean) plane of the IO element. We emphasize that the axial front vector $\vec{n}$ is a part of the symbol of the IO element, so, unless necessary, here and in Figures where the symbol of the IO element is shown as a constituent of an IO system, any individual reference to the axial front vector $\vec{n}$ will not be provided in writing.

Symbol 31A denotes an arbitrary (any) local IO element in a general view. Symbols 31Ax and 31Ay denote, respectively, xz and yz projections of an arbitrary IO element.

Symbol 31B denotes any multifunctional local IO element in a general view. Symbols 31Bx and 31By denote, respectively, xz and yz projections of a multifunctional IO element.

Symbol 32 denotes any (local or extended) IO elements of reflection in a general view. Symbols 32x and 32y denote, respectively, xz and yz projections of any IO element of reflection. Symbols 32Ax and 32Ay denote, respectively, xz and yz projections of any single-zone IO element of reflection. Symbols 32Bx and 32By denote, respectively, xz and yz projections of any vertical two-zone IO element of reflection. Symbols 32Cx and 32Cy denote, respectively, xz and yz projections of any horizontal two-zone IO element of reflection.

Symbol 33 denotes a local IO element of reflection in a general view. Symbols 33x and 33y denote, respectively, xz and yz projections of a local IO element of reflection. Symbols 33Ax and 33Ay denote, respectively, xz and yz projections of a local single-zone IO element of reflection. Symbols 33Bx and 33By denote, respectively, xz and yz projections of a local vertical two-zone IO element of reflection. Symbols 33Cx and 33Cy denote, respectively, xz and yz projections of a local horizontal two-zone IO element of reflection.

Symbol 34 denotes an extended IO element of reflection in a general view. Symbols 34x and 34y denote, respectively, xz and yz projections of an extended IO element of reflection. Symbols 34Ax and 34Ay denote, respectively, xz and yz projections of an extended single-zone IO element of reflection. Symbols 34Bx and 34By denote, respectively, xz and yz projections of an extended vertical two-zone IO element of reflection.

Symbol 35 denotes a local IO element of refraction in a general view. Symbols 35x and 35y denote, respectively, xz and yz projections of a local IO element of refraction. Symbol 35A denotes an extended IO element of refraction in a general view. Symbols 35Ax and 35Ay denote, respectively, xz and yz projections of an extended IO element of refraction.

Symbol 36 denotes a local IO lens module in a general view. Symbols 36x and 36y denote, respectively, xz and yz projections of a local IO lens module. Symbol 36A denotes an extended tall IO lens module in a general view. Symbols 36Ax and 36Ay denote, respectively, xz and yz projections of an extended IO lens module.

Symbol 37 denotes a local IO telescopic module in a general view. Symbols 37x and 37y denote, respectively, xz and yz projections of a local telescopic IO element. Symbol 37A denotes an extended telescopic IO element in a general view. Symbols 37Ax and 37Ay denote, respectively, xz and yz projections of an extended telescopic IO element.

Symbol 38 denotes a plane IO condenser in a general view. Symbols 38x and 38y denote, respectively, xz and yz projections of any plane IO condenser. Symbol 38A denotes an extended plane IO condenser in a general view. Symbols 38Ax and 38Ay denote, respectively, xz and yz projections of an extended plane IO condenser.

Symbol 39 denotes an array-incremental (extended array of arbitrary local IO elements) extended IO element in a general view. Symbols 39x and 39y denote, respectively, xz and yz projections of an extended array-incremental IO element. Symbols 39Ax and 39Ay denote, respectively, xz and yz projections of an array-incremental vertically extended (vertical extended array of local IO elements) IO element. Symbols 39Bx and 39By denote, respectively, xz and yz projections of a horizontal extended (horizontal extended array of local IO elements) IO element.

Symbol 41 denotes an extended array of arbitrary, preferably single-type, local multifunctional IO elements in a general view. Symbols 41x and 41y denote, respectively, xz and yz projections of an extended array of local multifunctional IO elements. Symbols 41Ax and 41Ay denote, respectively, xz and yz projections of a vertical extended array of local multifunctional IO elements. Symbols 41Bx and 41By denote, respectively, xz and yz projections of a horizontal extended array of local multifunctional IO elements.

Symbol 42 denotes an extended array of arbitrary (any), preferably single-type, local IO elements of reflection in a general view. Symbols 42x and 42y denote, respectively, xz and yz projections of an extended array of local IO elements of reflection. Symbols 42Ax and 42Ay denote, respectively, xz and yz projections of a vertical extended array of local IO elements of reflection. Symbols 42Bx and 42By denote, respectively, xz and yz projections of a horizontal extended array of local IO elements of reflection.

Symbols 43Ax and 43Ay denote, respectively, xz and yz projections of an extended array of local single-zone IO elements of reflection in general views. Symbols 43Bx and 43By denote, respectively, xz and yz projections of an array of local vertical two-zone IO elements of reflection. Symbols 43Cx and 43Cy denote, respectively, xz and yz projections of an array of local horizontal two-zone IO elements of reflection.

Symbol 44 denotes an extended array of arbitrary, preferably single-type, local IO elements refraction in a general view. Symbols 44x and 44y denote, respectively, xz and yz projections of an extended array of local IO elements refraction. Symbols 44Ax and 44Ay denote, respectively, xz and yz projections of a vertical extended array of local IO elements refraction. Symbols 44Bx and 44By denote, respectively, xz and yz projections of a horizontal extended array of local IO elements refraction.

Symbol 45 denotes an extended array of arbitrary (any) local IO lens modules in a general view. Symbols 45x and 45y denote, respectively, xz and yz projections of an extended array of local IO lens modules. Symbols 45Ax and 45Ay denote, respectively, xz and yz projections of a vertical extended array of local IO lens modules. Symbols 45Bx and 45By denote, respectively, xz and yz projections of a horizontal extended array of local IO lens modules.

Symbol 46 denotes an extended array of arbitrary, preferably single-type, local telescopic IO elements in a general view. Symbols 46x and 46y denote, respectively, xz and yz projections of an extended array of local telescopic IO elements. Symbols 46Ax and 46Ay denote, respectively, xz and yz projections of a vertical extended array of local telescopic IO elements. Symbols 46Bx and 46By denote, respectively, xz and yz projections of a horizontal extended array of local telescopic IO elements.

Symbol 47 denotes an extended array of arbitrary, preferably single-type, local IO condensers, particularly plane-parallel refracting condensers in a general view. Symbols 47x and 47y denote, respectively, xz and yz projections of an extended array of local IO condensers. Symbols 47Ax and 47Ay denote, respectively, xz and yz projections of a vertical extended array of local IO condensers. Symbols 47Bx and 47By denote, respectively, xz and yz projections of a horizontal extended array of local IO condensers.

Figure 131:
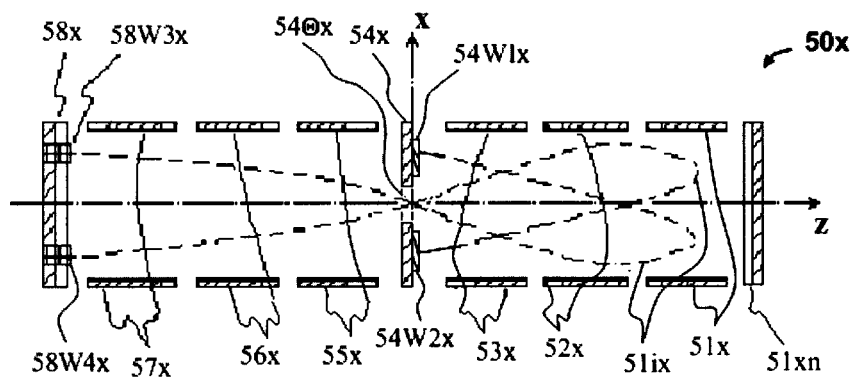
Figure 132:
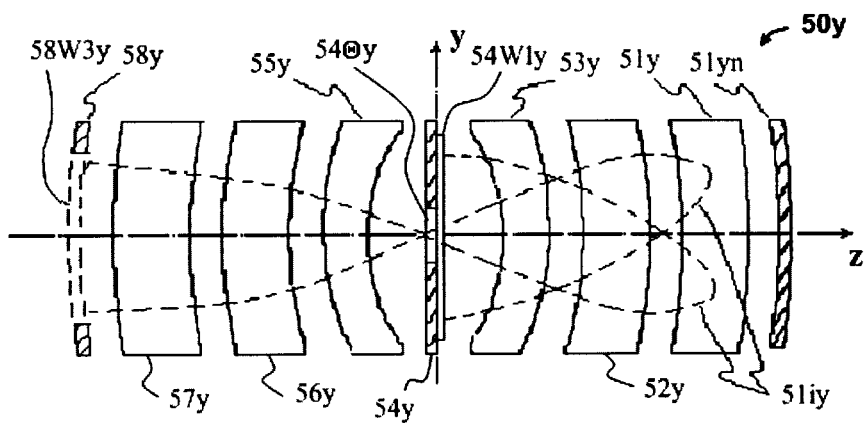

FIGS. 130, 131, and 132, are schematic representations of options for decisions regarding configurations of electrodes for doubly symmetric IB-channel with straight main axis.

FIG. 130 represents a space pattern of a doubly symmetric IB-channel 50, which comprises a reflecting electrode-limiter 51n, as well as electrodes 51, 52, and 53, in combination with a facing surface of electrode diaphragm 54 constituting a local IO element of reflection; electrodes 55, 56 and 57, as well as an input surface of electrode 58 and facing a surface of electrode diaphragm 54, constituting a local IO element of refraction. Diaphragm electrode 54 comprises a diaphragm 54Θ at its center, with a first gate port 54W1 and a second gate port 54W2. Input surface-electrode 58 comprises a first gate port 58W3 and a second gate port 58W4.

FIGS. 131 and 132 represent, respectively, xz and yz projections of sections 50x and 50y of IB-channel 50 in two orthogonal planes of symmetry, and projections of two characteristic ion trajectories in them (in each projection), namely, 51ix in xz projection and 51iy in yz projection.

Figure 133:
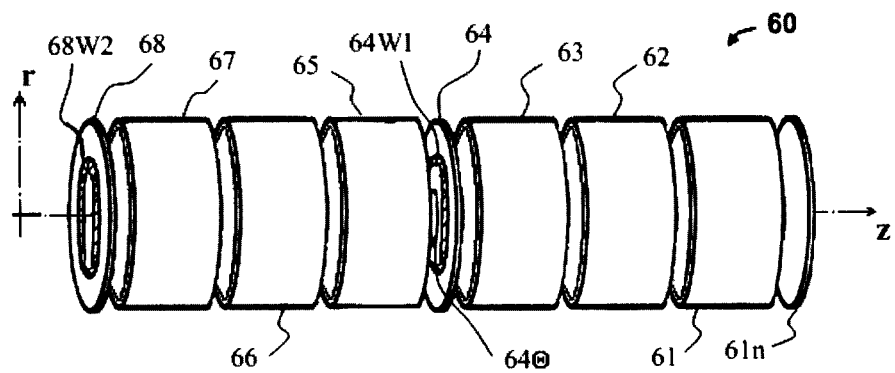
Figure 134:
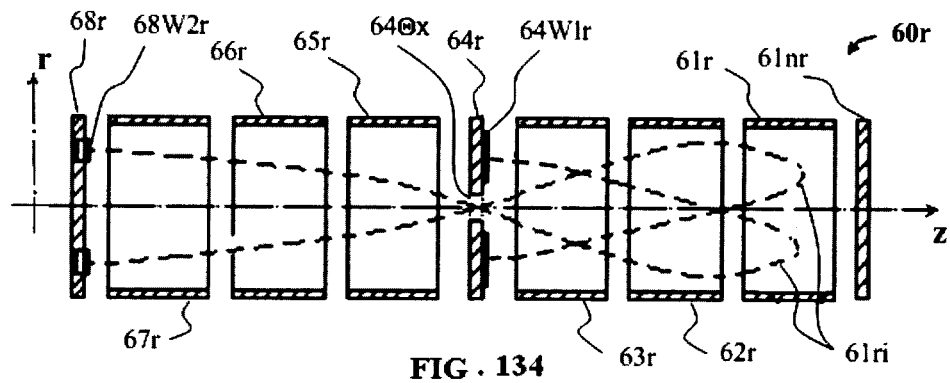

FIG. 133 represents a space pattern of an IB-channel 60 with rotational symmetry relative to a straight axis, which comprises a reflecting electrode-limiter 61n, as well as electrodes 61, 62, and 63 and facing a surface of an electrode diaphragm 64 constituting a local IO element of reflection; electrodes 65, 66 and 67 as well as an input electrode 68 and facing a surface of electrode diaphragm 64, constituting a local IO element of refraction. Diaphragm electrode 64 comprises a diaphragm 64Θ at its center, has a gate port 64W1, and is ring-shaped with a center located on the axis of rotational symmetry of the IB-channel. Input surface-electrode 68 comprises a gate port 68W2. FIG. 134 represents the yz projection of radial section 60r of IB-channel 60, and projections of two characteristic ions trajectories 61ri within the projection.

FIGS. 135 to 151 represent, respectively, the diagrams of control subsystems 70A, 70B, 70C, 70D, 70E, 70F, 80Ay, 80Ax, 80By, 80Bx, 80Cy, 80Cx, 80Dy, 80Ey, 80Fy, 80Gy and 80Hy, each of which comprises one or more IO elements, selected from a group comprising their types, denoted by the symbols used in FIGS. 20 to 129. Each of the IO elements is located at a specified spatial orientation with respect to each other, and relative to a direction of an averaged vector of ion flux entering the IO element. As stated above, front vector $\overset{\shortmid}{n}$ is a part of symbol of an IO element, so, unless necessary, any individual reference to it will not be provided in writing.

Figure 135:
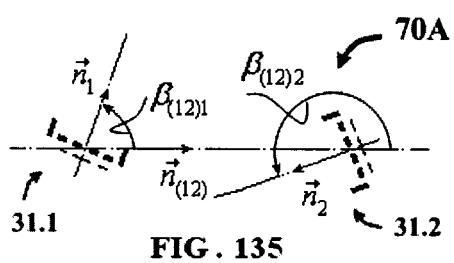
FIGS. 135-151 represent diagrams of IO control subsystem arrangements.
Figure 136:
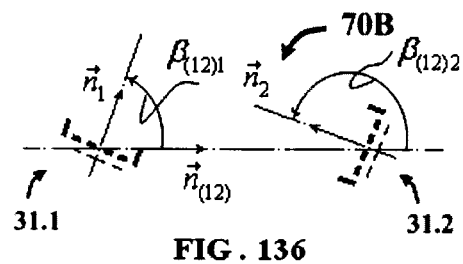

Each of control subsystems 70A and 70B in FIGS. 135 and 136 comprises two IO elements of the type shown in general view 31A: a first IO element 31.1 and a second IO element 31.2.

In control subsystem 70A, the IO elements are arranged so that the angle $\beta_{(12)1}$, defined between the vectors read counterclockwise from the vector of "monitoring-1" $\vec{n}_{(12)}$ (unitary vector oriented from the first IO element 31.1 to the second IO element 31.2 and located on the line connecting likely effective points of reflection/refraction of the first IO element 31.1 and second IO element 31.2 of reflection) to the unitary axial vector $\vec{n}_1$ of first IO element 31.1, is within the range of $$0 p \beta_{(12)1} p \frac{\pi}{2}.$$

Angle $\beta_{(12)2}$ between vectors read counterclockwise from the vector $\vec{n}_{(12)}$ to the unitary axial vector $\vec{n}_2$ of second IO element 31.2, is within the range of $$\pi p \beta_{(12)2} p \frac{3\pi}{2}.$$

In control subsystem 70B, the IO elements are arranged so that the angle $\beta_{(12)1}$ is within the range of $$0 p \beta_{(12)1} p \frac{\pi}{2},$$

while angle $\beta_{(12)2}$ is within the range of $$\frac{\pi}{2} p \beta_{(12)1} p \pi.$$

Figure 137:
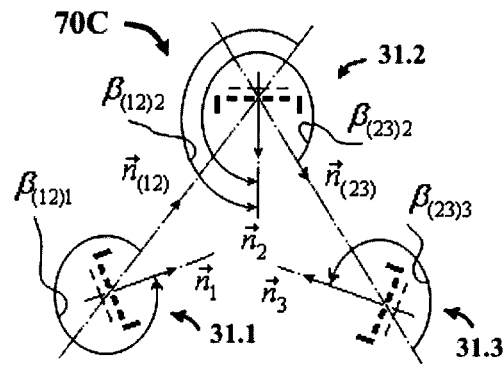
Figure 138:
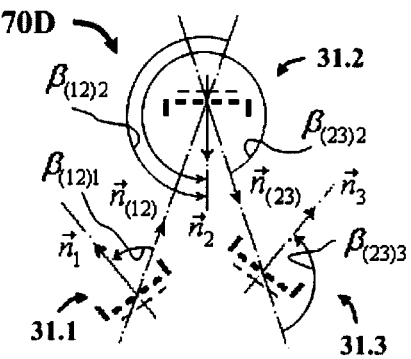
Figure 139:
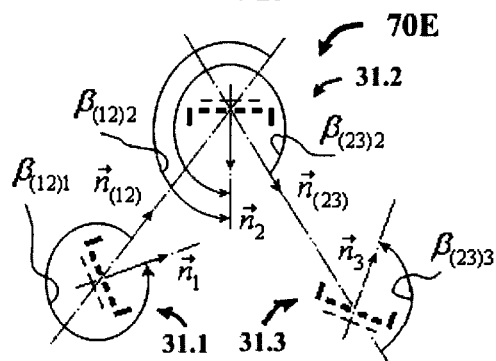

Each of control subsystems 70C, 70D and 70E, shown respectively in FIGS. 137, 138, and 139, comprises three IO elements of the type shown in general view 31A: a first IO element 31.1, a second IO element 31.2, and a third IO element 31.3, in which angle $\beta_{(12)2}$ is within the range of $$\pi p \beta_{(12)2} p \frac{3\pi}{2},$$

and angle $\beta_{(23)2}$, defined between vectors read counterclockwise from the vector of "monitoring-2" $\vec{n}_{(23)}$ (unitary vector oriented from second IO element 31.2 to third IO element 31.3 and located on the line connecting likely effective points of reflection/refraction of the second IO element and the third IO element) to the unitary axial vector $\vec{n}_2$, is within the range of $$\frac{3\pi}{2} p \beta_{(23)2} p 2\pi.$$

In control subsystem 70C, IO angle $\beta_{(12)1}$ is within the range of $$\frac{3\pi}{2} p \beta_{(12)1} p 2\pi,$$

and angle $\beta_{(23)3}$, defined between vectors read counterclockwise from vector $\vec{n}_{(23)}$ to the unitary axial vector $\vec{n}_3$ of third IO element 31.3, is within the range of $$\pi p \beta_{(23)3} p \frac{3\pi}{2}.$$

In control subsystem 70D, IO angle $\beta_{(12)1}$ is within the range of $$0 p \beta_{(12)1} p \frac{\pi}{2},$$

and angle $\beta_{(23)3}$ is within the range of $$\frac{\pi}{2} p \beta_{(23)3} p \pi.$$

In control subsystem 70E, IO angle $\beta_{(12)1}$ is within the range of $$\frac{3\pi}{2} p \beta_{(12)1} p 2\pi,$$

and angle $\beta_{(23)3}$ is within the range of $$\frac{\pi}{2} p \beta_{(23)3} p \pi.$$

Figure 140:
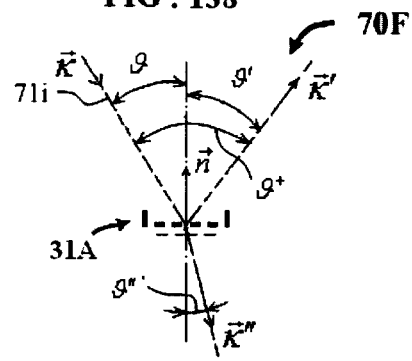

The control subsystem shown in FIG. 140 comprises one IO element of the type shown in general view 31A. In FIG. 140 two mode of IO element operation are shown, such that the IO element operates as a multifunctional IO element: one operation mode as a module of reflection is shown by two unitary vectors $\vec{k}$ and $\vec{k}'$, and another operation mode as a module of refraction is shown by two unitary vectors $\vec{k}$ and $\vec{k}''$. Dip vector $\vec{k}$ corresponds to the averaged ion flux motion direction before entering the field of IO element 31A and the direction of its motion is characterized by the angle of dip $\vartheta$ of ion flux trajectory 71i, angle $\vartheta$ defined between dip vector $\vec{k}$ and axial vector $\vec{n}$, is within the range of $$0 p \vartheta p \frac{\pi}{2}.$$

Vector of reflection $\vec{k}'$ corresponds to the averaged ion flux motion direction after leaving the field of the IO elements of reflection and the direction of its motion is characterized by the angle of ion flux reflection $\vartheta'$ which is within the range of $$0 p \vartheta' p \frac{\pi}{2}.$$

Vector of refraction $\vec{k}''$ corresponds to the averaged ion flux motion direction after leaving the field of IO element of refraction and the direction of its motion is characterized by the angle of ion flux refraction $\vartheta''$, which is within the range of $$_0 p \vartheta p \frac{\pi}{2}.$$

Figure 141:
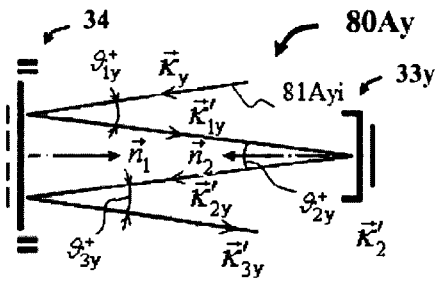
Figure 142:
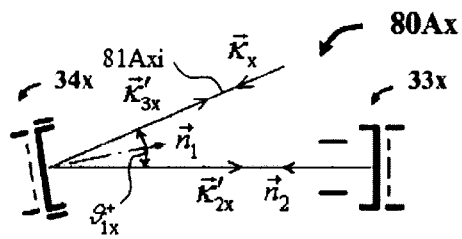

An angle of input/output $\vartheta^+$ under reflection is equal to $\vartheta^+ = \vartheta' + \vartheta$. FIGS. 141 and 142 show projections 80Ay and 80Ax, respectively projected on yz and xz planes of a rectangular Cartesian system of coordinates, and having a control subsystem comprising an extended P-element of reflection 34 and a symmetric local P-element of reflection 33y. Ion flux 81Ai (in FIGS. 141 and 142 its projections are shown on the planes yz 81Ayi and xz 81Axi, respectively), is reflected in series from extended P-element of reflection 34 and second P-element of reflection 33.2.

In FIG. 141, projections on the coordinate plane yz of a rectangular Cartesian system of coordinates are shown, including: control subsystem 80Ay; dip vector of input $\vec{k}_y$, vector of first reflection $\vec{k}'_{1y}$ from extended P-element of reflection 34, vector of reflection $\vec{k}'_{2y}$ from local P-element of reflection 33y, vector of second reflection from extended P-element of reflection 34, and output $\vec{k}'_{3y}$, all of which are averaged vectors of ion flux direction 81Ayi; angle of ion flux input-reflection $\vartheta^+_{1y}$ under a first reflection from extended P-element of reflection 34; angle of ion flux input-reflection $\vartheta^+_{2y}$, under reflection from local IO P-element of reflection 33y; and angle of ion flux input-reflection $\vartheta^+_{3x}$ under a second reflection from extended P-element of reflection 34.

Figure 143:
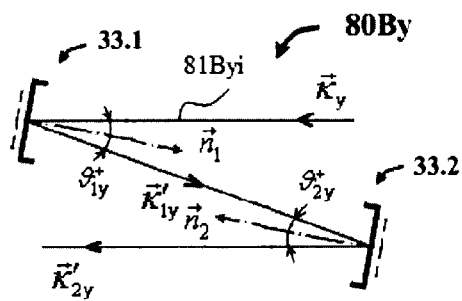
Figure 144:
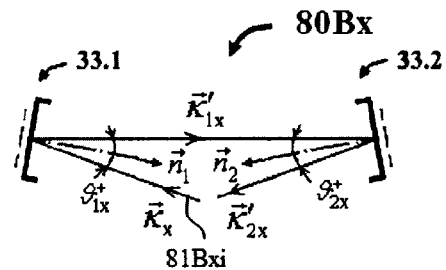

In FIG. 142 projections on the coordinate plane xz of a rectangular Cartesian system of coordinates are shown, including: control subsystem 80Ax; vector $\vec{k}'_{3x}$ of second reflection from extended P-element of reflection 34 and output, vector of reflection $\vec{k}'_{2x}$ from local P-element of reflection 33x, all of which are averaged vectors of ion flux direction 81Bxi; angle of ion flux input-reflection $\vartheta^+_{3x}$ under a second reflection from extended P-element of reflection 34. It is appreciated that certain vectors and angles are not visible in FIG. 142, including: ion flux dip vector $\vec{k}_x$ which is in line with $\vec{k}'_{3x}$; and vector of first reflection $\vec{k}'_{1x}$ from extended P-element of reflection 34 which is in line with $\vec{k}'_{3x}$. FIGS. 143 and 144 show projections 80By and 80Bx, respectively projected on the planes yz and xz of a rectangular Cartesian system. One particular case of control subsystem 70A is shown comprising two symmetric IO elements of reflection: a first IO element of reflection 33.1 and a second IO element of reflection 33.2. Ion flux 81Bi (shown in FIGS. 143 and 144 in its projections on the planes yz 81Byi and xz 81Bxi, respectively) is reflected in series from first and second P-elements of reflection 33.1 and 33.2.

In FIG. 143 projections on the coordinate plane yz of a rectangular Cartesian system of coordinates are shown, including: control subsystem 80By; input dip vector $\vec{k}_y$, vector of reflection $\vec{k}'_{1y}$ from first IO element of reflection 33.1, vector of reflection from second P-element of reflection 33.2, and output $\vec{k}'_{2y}$, all of which are averaged vectors of ion flux direction 81Byi; angle of ion flux input-reflection $\vartheta^+_{1y}$ under reflection from the first P-element of reflection 33.1; and angle of ion flux input-reflection $\vartheta^+_{2y}$ under reflection from second P-element of reflection 33.2.

In FIG. 144 projections on the coordinate plane xz of a rectangular Cartesian system of coordinates are shown, including: control subsystem 80Bx; input dip vector $\vec{k}_y$; vector of reflection $\vec{k}'_{1x}$ from first P-element of reflection 33.1, vector of reflection from second P-element of reflection 33.2 and output $\vec{k}'_{2x}$, all of which are averaged vectors of ion flux direction 81Bxi; angle of input-reflection $\vartheta^+_{1x}$ from first P-element of reflection 33.1; and angle of ion flux input-reflection $\vartheta^+_{2x}$ from second P-element of reflection 33.2.

The control subsystem shown in FIGS. 143 and 144 includes an optional feature for arranging an averaged vector of path ion flux direction in different planes before entering and after leaving the field of the control subsystem (configured with hetero-planar input-output). The output and input mean planes of the P-elements intercross at an angle $\overline{\omega}$ (not shown in the Figures), and include an optional feature to approximately coincide the lines of their intercrossing with an averaged vector of path ion flux direction at a midway point between P-elements, wherein angle $\overline{\omega}$ is within the range of $$_0 p \varpi p \frac{\pi}{2}.$$

Figure 145:
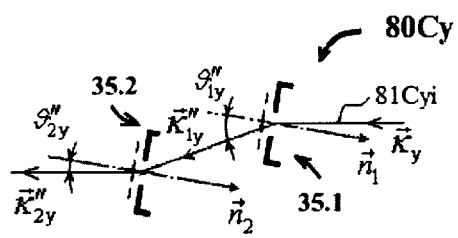
Figure 146:
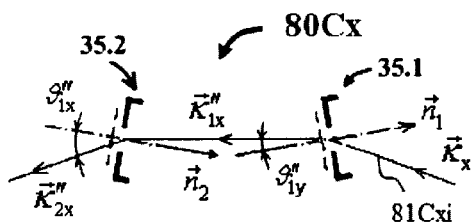

The control subsystem shown in FIGS. 143 and 144 is a symmetric control subsystem with hetero-planar input-output, provided that $\vartheta^+_{1x} = \vartheta^+_{2x}$ and $\vartheta^+_{1y} = \vartheta^+_{2y}$. This control subsystem can also be called a subsystem of transfer with hetero-planar parallel projection input-output, provided that the vectors $\vec{k}_y$ and $\vec{k}'_{2y}$ are parallel to each other. FIGS. 145 and 146 show projections 80Cy and 80Cx on the planes yz and xz of a rectangular Cartesian system, respectively. One particular case of control subsystem 70A is shown, comprising two IO elements of refraction: first IO element of refraction 35.1 and second IO element of refraction 35.2. Ion flux 81Ci (shown in FIGS. 145 and 146 in its projections on the planes yz 81Cyi and xz 81Cxi, respectively), is refracted in series in the first P-element of refraction 35.1 and second P-element of refraction 35.2.

In FIG. 145, projections on the coordinate plane yz of a rectangular Cartesian system of coordinates are shown, including: control subsystem 80Cy; input dip vector $\vec{k}_y$, vector of refraction $\vec{k}''_{1y}$ from the first IO element of refraction 35.1, and vector of refraction $\vec{k}''_{2y}$ from the second IO element of refraction 35.2, all of which are averaged vectors of ion flux 81Cyi direction; angle of refraction $\vartheta''_{1y}$ from the first IO P-element of refraction 35.1; and angle of ion flux refraction $\vartheta''_{2y}$ from the second IO P-element of refraction 35.2.

In FIG. 146, projections on the coordinate plane xz of a rectangular Cartesian system of coordinates are shown, including: control subsystem 80Cx; input dip vector $\vec{k}_x$, vector of refraction $\vec{k}'_{1x}$ in the first IO element of refraction 35.1, a vector of refraction in the second IO element of refraction 35.2, and output $\vec{k}'_{2x}$, all of which are averaged vectors of ion flux direction 81Cxi; angle of refraction $\vartheta''_{1x}$ in the first IO P-element of refraction 35.1; and angle of ion flux refraction $\vartheta''_{2x}$ in the second IO P-element of refraction 35.2.

The control subsystem shown in FIGS. 145 and 146 includes an optional feature for arranging averaged vectors of path ion flux directions in different planes before entering and after leaving the field the of control subsystem (configured with a hetero-planar input-output). Additionally, the output and input mean planes of the P-elements intercross at an angle $\overline{\omega}$ (not shown in the Figure), and include an optional feature to approximately coincide the lines of their intercrossing with an averaged vector of path ion flux direction at a midway point between the P-elements, wherein angle $\overline{\omega}$ is within the range of $$0 p \varpi p \frac{\pi}{2}.$$

Figure 147:
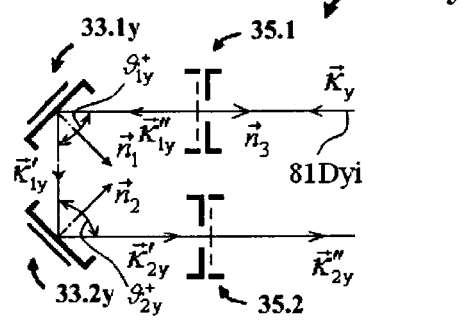
Figure 148:
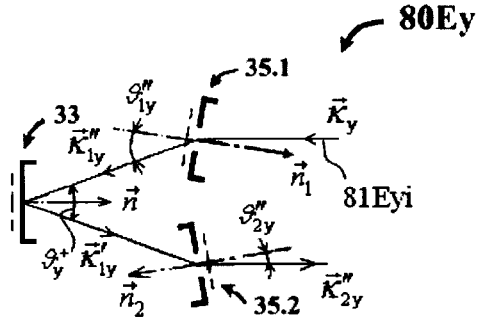
Figure 149:
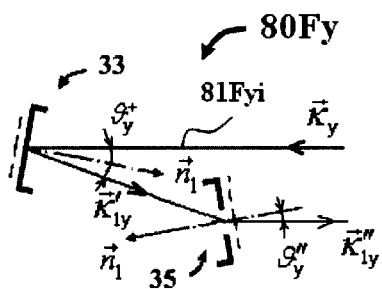

In FIGS. 147, 148 and 149, projections on the plane of motions coinciding with plane yz of a rectangular Cartesian coordinate system are shown, including, respectively, single-plane control subsystems 80Dy, 80Ey and 80Fy, the input-output of which are shown by antiparallel vectors (antiparallel input-output). FIG. 147 shows: control subsystem 80Dy; input dip vector $\vec{k}_y$, vector of refraction $\vec{k}''_{1y}$ in the first IO element of refraction 35.1, vector of reflection $\vec{k}'_{1y}$ from the first IO element of reflection 33.1, vector of reflection $\vec{k}'_{2y}$ from the second IO element of reflection 33.2, a vector of refraction in the second IO element of refraction 35.2, and output $\vec{k}''_{2y}$, all of which are averaged vectors of ion flux direction 81Dyi; angle of ion flux input-reflection $\vartheta^+_{1y}$ under reflection from the first IO P-element of refraction 33.1; and angle of ion flux input-reflection $\vartheta^+_{2y}$ under reflection from the second IO P-element of reflection 33.2. Control subsystem 80Dy may be implemented without IO elements refraction 35.1 and 35.2. FIG. 148 shows: control subsystem 80Ey; input dip vector $\vec{k}_y$, vector of refraction $\vec{k}''_{1y}$ in first IO element of refraction 35.1, vector of reflection $\vec{k}'_{1y}$ from IO element of reflection 33, a vector of refraction in second IO element of refraction 35.2, and output $\vec{k}''_{2y}$, all of which are averaged vectors of ion flux direction 81Eyi; angle of ion flux input-reflection $\vartheta^+_y$ under reflection from the IO P-element of reflection 33; angle of refraction $\vartheta''_{1y}$ from first IO P-element of refraction 35.1; and angle of refraction $\vartheta''_{2y}$ from second IO P-element of refraction 35.2. FIG. 149 shows: control subsystem 80Fy; input dip vector $\vec{k}_y$, vector of reflection $\vec{k}'_{1y}$ from the IO element of reflection 33, a vector of refraction in the IO element of refraction 35, and output $\vec{k}''_{1y}$, all of which are averaged vectors of ion flux direction 81Fyi; angle of ion flux input-reflection $\vartheta^+_y$ under reflection from the IO P-element of reflection 33; and angle of refraction $\vartheta''_{1y}$ from the IO element of refraction 35.

Figure 150:
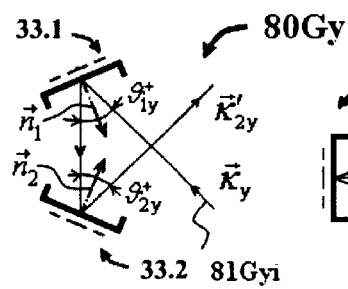
Figure 151:
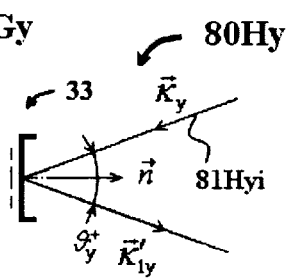

In FIGS. 150 and 151, projections on the plane of motion coinciding with plane yz of a rectangular Cartesian coordinate system are shown, including, respectively, single-plane control subsystems 80G and 80Hy, the input-output of which are shown as single-plane IO with vectors convergent at an angle (input-output coinciding at an angle or skew-angle input-output). FIG. 150 shows: doubly-reflecting control subsystem 80Gy; input dip vector $\vec{k}_y$, vector of reflection $\vec{k}'_{1y}$ from first IO element of reflection 33.1, a vector of reflection from second IO element of reflection 33.2, and output $\vec{k}'_{2y}$, all of which are averaged vectors of ion flux direction 81Gyi; angle of ion flux input-reflection $\vartheta^+_{1y}$ under reflection from first IO element of reflection 33.1; and angle of ion flux input-reflection $\vartheta^+_{2y}$ under reflection from second IO P-element of reflection 33.2. FIG. 151 shows: single-reflecting control subsystem 80Hy; input dip vector $\vec{k}_y$, a vector of reflection from the IO element of reflection 33, and output $\vec{k}'_{1y}$, all of which are averaged vectors of ion flux direction 81Hyi; and angle of ion flux input-reflection $\vartheta^+_y$ under reflection from the IO element of reflection 33.

Figure 152:
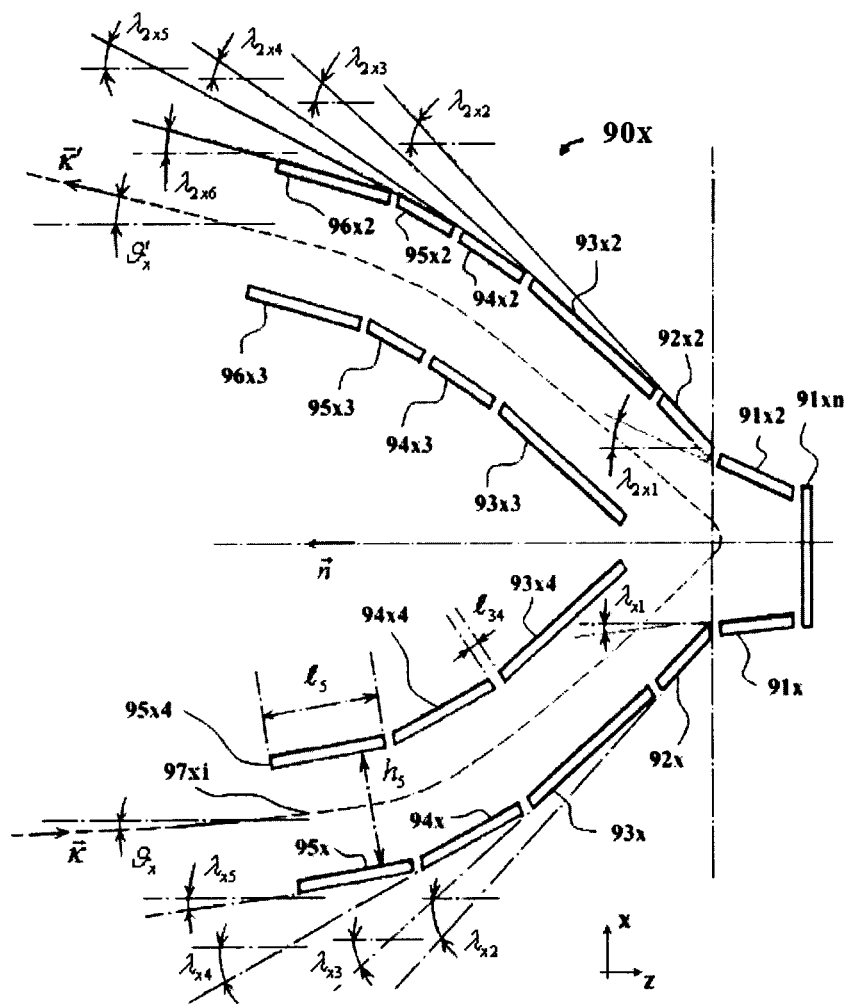
FIGS. 152-210 represent diagrams of IO element arrangements and characteristic ion paths.

In FIG. 152, a vertical two-zone module of reflection 90x with an axial vector $\vec{n}$, is shown in an elevation profile along its vertical plane which coincides with coordinate plane xz. Module 90x includes:

vertical limiting electrodes 91xn;

a first electrode of reflection including two constituents 91x and 91x2, arranged respectively at the angles $\lambda_{1x}$ and $\lambda_{1x2}$ relative to the axial vector $\vec{n}$;

a second electrode of reflection including two constituents 92x and 92x2, arranged respectively at the angles $\lambda_{2x}$ and $\lambda_{2x2}$ relative to the axial vector $\vec{n}$;

a third electrode of a lower zone including two constituents 93x and 93x4, arranged at an angle $\lambda_{3x}$ relative to the axial vector $\vec{n}$ and parallel to each other; a fourth electrode of the lower zone including two constituents 94x and 94x4, arranged at an angle $\lambda_{4x}$ relative to the axial vector $\vec{n}$ and parallel to each other, and preferably $\lambda_{4x}=0$;

a fifth electrode of the lower zone including two constituents 95x and 95x4, arranged at an angle $\lambda_{5x}$ relative to the axial vector $\vec{n}$ and parallel to each other;

a third electrode of an upper zone including two constituents 93x2 and 93x3, arranged at an angle $\lambda_{3x2}$ relative to the axial vector $\vec{n}$ and parallel to each other;

a fourth electrode of the upper zone including two constituents 94x2 and 94x3, arranged at an angle $\lambda_{4x2}$ relative to the axial vector $\vec{n}$ and parallel to each other;

a fifth electrode of the upper zone including two constituents 95x2 and 95x3, arranged at an angle $\lambda_{5x2}$ relative to the axial vector $\vec{n}$ and parallel to each other; and a sixth electrode of the upper zone including two constituents 96x2 and 96x3, arranged at an angle $\lambda_{6x2}$ relative to the axial vector $\overset{\shortmid}{n}$ and parallel to each other. When considering the performance characteristics of vertical two-zone module of reflection 90x, as well as any other IO element, the configuration and size of the effective (inner) surfaces of each electrode have significant importance. In FIG. 152, each electrode is characterized by its width and height. For brevity, inner surface $S_5$, and values of width $l_5$ and height $h_5$, are denoted only for the fifth electrode of the lower zone in FIG. 152. Any two adjacent electrodes are separated by a gap spacing, or an electrode gap. The value of gap spacing between the third and the fourth electrodes of the lower zone is denoted by $l_{34}$. Values of electrode gap spacing are very small as compared to the values of electrode heights, e.g., $l_{34} \gg h_5$. The ion flux characterized by the averaged ion flux motion trajectory 91i (shown in FIG. 152 in its projection on the plane xz 91xi), passes the fields generated by the first input zone including three electrodes, each of which comprises two constituents: 95x and 95x4, 94x and 94x4, 93x and 93x4 and by the zones of reflection including three electrodes, each of which comprises two constituents: 95x and 95x4, 94x and 94x4, 93x and 93x4. Additionally, as an example, FIG. 152 shows a characteristic ion flux motion trajectory 97xi in the vertical two-zone module of reflection 90x. Characteristic ion trajectory 97xi comprises two branches: a straight branch shown by a dashed line to the point of reflection $z_*$ and a backward branch shown a dashed line from the point of reflection $z_*$.

Parameters of ion trajectory are determined: for the straight branch, by ion motion direction in the straight section of the ion trajectory before entering the field of vertical two-zone module of reflection 90x, as specified by unitary vector $\overset{\shortmid}{\kappa}$, and by the angle of input into one of zones (in this particular case, into the lower zone) of vertical two-zone module of reflection 90x, as specified by angle $\theta$ between axial vector $\overset{\shortmid}{n}$ and the axis comprising vector $\overset{\shortmid}{\kappa}$; and for the backward branch, by ion motion direction in the straight section of ion trajectory after leaving the field of vertical two-zone module of reflection 90x, as specified by unitary vector $\kappa'$, and by the angle of leaving the zone of output (in this particular case, the upper zone) of vertical two-zone module of reflection 90x, as specified by angle $\theta'$ between axial vector $\overset{\shortmid}{n}$ and the axis comprising vector $\kappa'$.

Figure 161:
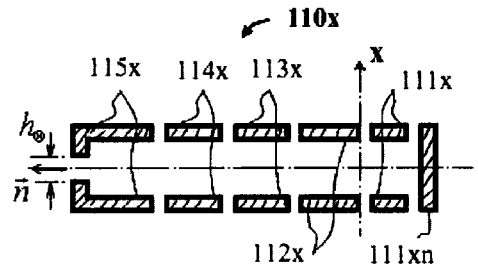
Figure 162:
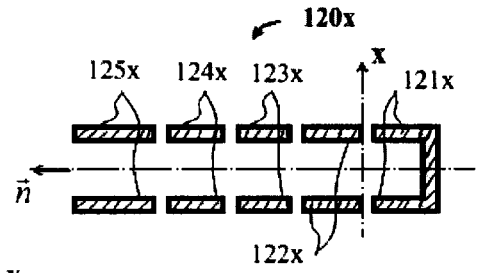

Vertical two-zone module of reflection 90x shown in FIG. 152 characterizes an elevation profile of vertical two-zone modules of reflection. In particular cases, one or more optional versions are selected from the following group:

the number of electrodes in the lower zone and the upper zone may be less or more than specified in FIG. 152;

the vertical limiting electrodes 91xn is omitted;

the first electrode of reflection is arranged so that the angles $\lambda_{1x}=\lambda_{1x2}$ or $\lambda_{1x}=A_{1x2}=0$; the second electrode of reflection is arranged so that $\lambda_{2x}=0$ or $\lambda_{2x2}=0$;

the second electrode of reflection is arranged so that $\lambda_{2x}=\lambda_{2x2}$;

the third electrode of the lower zone is arranged so that $\lambda_{3x}=0$;

the fourth electrode of the lower zone is arranged so that $\lambda_{4x}=0$; the fifth electrode of the lower zone is arranged so that $\lambda_{5x}=0$;

the third electrode of the upper zone is arranged so that $\lambda_{3x2}=0$;

the fourth electrode of the upper zone is arranged so that $\lambda_{4x2}=0$;

the fifth electrode of the upper zone is arranged so that $\lambda_{5x2}=0$;

the sixth electrode of the upper zone is arranged so that $\lambda_{6x2}=0$;

The geometry of the module, determined by a plurality of features including number of electrodes, width/height ratio of each electrode, particularly $$\frac{l_5}{h_5},$$

angle of an electrode's constituent slopes to axial vector $\overset{\shortmid}{n}$, and the configurations of electrodes, among them configurations in projection on a geometrical mean plane of the vertical two-zone IO element of reflection and its potential characteristics, such as distribution of electric potentials at working electrode surfaces, are specified, as would be for any other IO element, with an optional feature for assuring specific requirements of the structure and dynamics of charged particle flow after leaving the field of a given IO element. The specific requirements of charged particles flow structure for the vertical two-zone module of reflection, as well as for any other IO element, are designed to be used in MC devices and are characterized by space-time structure and by dynamics of flux. In FIGS. 153 to 167, the mean plane of P-elements of reflection are shown along their vertical plane, which are superposed with coordinate plane xz. In FIGS. 153 to 160 are shown P-elements of reflection in which the vertical limiting electrode is arranged separately from the first electrode, and the input diaphragm and side electrodes are omitted. FIG. 153 shows a module of reflection 90Ax including a mean plane S comprising an axial vector $\overset{\shortmid}{n}$, a constant height h, and comprising a vertical limiting electrode 9, a first electrode of reflection 91A, a second electrode of reflection 92A, a third electrode 93A, a fourth 94A, and a fifth electrode 95A. The effective (inner) electrode surfaces of single-zone module of reflection 90Ax have non-uniform heights h and are arranged on planes parallel to each other and to mean plane S, integrated with coordinate plane yz. FIG. 154 shows a single pitch P-element of reflection 90Bx with an axial vector $\overset{\shortmid}{n}$, comprising: a vertical limiting electrode 91Bn, a first electrode of reflection including constituents 91B and 91B2, a second electrode of reflection including constituents 92B and 92B2, a third electrode including constituents 93B and 93B2, and a fourth electrode including constituents 94B and 94B2. The effective (inner) electrode surfaces of single-zone module of reflection 90Bx have a single pitch: upper constituents 91B2 and 92B2, respectively, of first and second electrodes of reflection are arranged at an angle relative to effective surfaces of other electrodes. FIG. 155 shows a single pitch height module of reflection 90Cx comprising a vertical limiting electrode 91Cn, a first electrode of reflection including constituents 91C and 91C2, a second electrode of reflection including constituents 92C and 92C2, a third electrode of reflection including constituents 93C and 93C2, and a fourth electrode of reflection including constituents 94C and 94C2. The effective (inner) electrode surfaces of module of reflection 90Cx have a single pitch where the upper constituents of all electrodes are arranged at an angle relative to surfaces of the lower electrode constituents, which are arranged in one plane and perpendicularly to the plane of vertical limiting electrode 91Cn. FIG. 156 shows a two-pitch height module of reflection 90Dx comprising a vertical limiting electrode 91Dn, a first electrode of reflection including constituents 91D and 91D2, a second electrode of reflection including constituents 92D and 92D2, a third electrode including constituents 93D and 93D2, and a fourth electrode including constituents 94D and 94D2 arranged symmetrically to the mean surface. The effective (inner) electrode surfaces of single-zone module of reflection 90Dx have two pitches, where upper and lower electrode constituents, excepting the first electrode, are arranged at angles relative to the mean plane of surface. Module of reflection 90Dx is arranged symmetrically relative to the mean plane, having axis yz perpendicular to its vertical plane. FIG. 157 shows a single-pitch-height vertical two-zone P-element of reflection 90Ex, comprising: a vertical limiting electrode 91En, a first electrode of reflection including constituents 91E and 91E2, a second electrode of reflection including constituents 92E and 92E2, a third electrode of a lower zone including constituents 93E and 93E4, a third electrode of an upper zone including constituents 93E2 and 93E3, and a fourth electrode of the upper zone including constituents 94E2 and 94E4. The effective (inner) electrode surfaces of vertical two-zone module of reflection 90SDx have a single pitch: upper constituents 91E2 and 92E2, respectively of the first and second electrodes, are arranged at an angle relative to other electrode constituents. FIG. 158 show a single-pitch-height vertical two-zone P-element of reflection 90Fx, comprising a vertical limiting electrode 91Fn, a first electrode of reflection including constituents 91F and 91F2, a second electrode of reflection including constituents 92F and 92F2, a third electrode of a lower zone including constituents 93F and 93F4, a third electrode of an upper zone including constituents 93E2 and 93E3, and a fourth electrode of the upper zone including constituents 94F2 and 94F3. The effective (inner) electrode surfaces of vertical two-zone module of reflection 90Ex have a single pitch: the upper electrode constituents are arranged at an angle relative to the lower electrode constituents, which are located in one plane. FIG. 159 shows a symmetrical two-pitch-height vertical two-zone P-element of reflection 90Gx, comprising a vertical limiting electrode 91Gn, a first electrode of reflection including constituents 91G and 91G2, a second electrode of reflection including constituents 92G and 92G2, a third electrode of a lower zone including constituents 93G and 93G4, a fourth electrode of the lower zone including constituents 94G and 94G4, a third electrode of an upper zone including constituents 93G2 and 93G3, and a fourth electrode of the upper zone including constituents 94G2 and 94G3. The effective (inner) electrode surfaces of vertical two-zone module of reflection 90Fx have two pitches: the upper and lower zones of the electrodes are arranged at an angle relative to each other. Vertical two-zone module of reflection 90Fx is arranged symmetrically relative to the mean plane having axis yz perpendicularly to its vertical plane. FIG. 160 shows a non-uniform-height (uneven) P-element of reflection 100x, comprising a vertical limiting electrode 101xn, a first electrode of reflection 101x, a second electrode of reflection 102x, a third electrode 103G, and a fourth electrode 104G. The effective (inner) electrode surfaces of single-zone module of reflection 90Ax have different heights: the second electrode of reflection 102x has a height $h_2$, while all other electrodes have non-uniform heights $h_3$. FIG. 161 shows a module of reflection 110x of constant height with an axial vector $\vec{n}$, comprising a vertical limiting electrode 111xn, a first electrode of reflection 111x, a second electrode of reflection 112x, a third electrode 113x, a fourth electrode 114x, and a fifth electrodes 115x with a slit input diaphragm of height d. FIG. 162 shows a constant-width module of reflection 120x with an axial vector $\vec{n}$, comprising a blind (comprising vertical limiting electrode) edge electrode of reflection 121x, a second electrode of reflection 122x, a third electrode 123x, a fourth electrode 124x, and a fifth electrode 125x of IO element 120x.

P-elements of reflection 110x and 120x, shown respectively in FIGS. 161 and 162, are alternative versions of P-element of reflection 90Ax, shown in FIG. 153. Module 110x, unlike module 90Ax, includes a slit input diaphragm. P-element 120x, unlike module 90Ax, includes a blind edge electrode of reflection. A third alternative version of P-element of reflection 90Ax comprises a slit input diaphragm and a blind edge electrode of reflection. Referring to that defined above, each of P-elements of reflection shown in FIGS. 153-160 may optionally be arranged in three alternative versions: with a slit input diaphragm; with a blind edge electrode of reflection; and with a slit input diaphragm and with a blind edge electrode of reflection.

Each of the versions for any P-elements of reflection, selected from the group including 90Bx, 90Cx, 90Dx, 90Ex, 90Fx, 90Gx and 100x, differs by its design features. Additionally, each is optionally characterized by five additional alternative versions based on the arrangement of electrodes with lateral sides: crosswise type (with lateral constituents); box-type; crosswise-mixed type; box-mixed type; and doubly mixed type.

Figure 163:
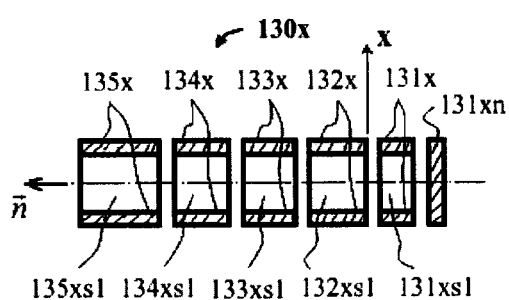
Figure 164:
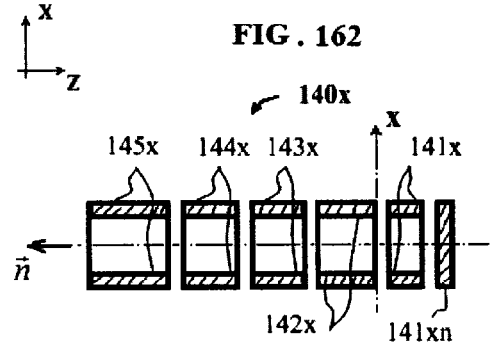
Figure 165:
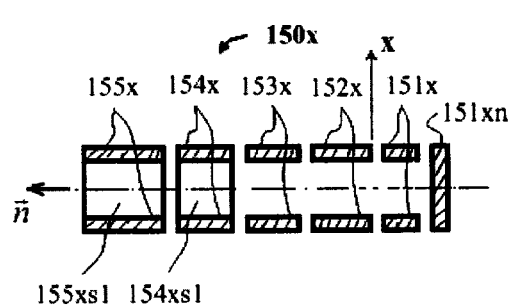
Figure 166:
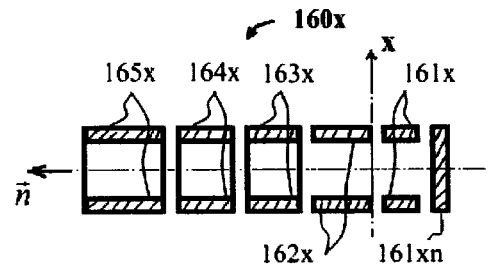

To explain the above mentioned design multiplicity of P-elements of reflection as exemplified by their types and vertical limiting electrodes, and including extended P-elements of reflection, there are provided FIGS. 163 to 167 illustrating the P-elements of reflection through a section in their vertical plane, which coincides with coordinate plane xz. FIG. 163 shows a module of reflection 130x of a crosswise type (with lateral constituents) and of a constant-height, with an axial vector $\vec{n}$, comprising: vertical limiting electrodes 131xn; horizontal constituents 131x and 131xs1 which are lateral constituents of a first electrode of reflection; horizontal constituents 132x and 132xs1 which are lateral constituents of a second electrode of reflection; horizontal constituents 133x and 133xs1 which are lateral constituents of a third electrode; horizontal constituents 134x and 134xs1 which are lateral constituents of a fourth electrode; and horizontal constituents 135x and 135xs1 which are lateral constituents of a fifth electrode. FIG. 164 shows a module of reflection 140x of a box-type and a constant height, with an axial vector $\vec{n}$, comprising: a vertical limiting electrode 141xn; a first electrode of reflection 141x; a second electrode of reflection 132x; a third electrode 133x; a fourth electrode 134x; and a fifth electrode 135x. FIG. 165 shows a module of reflection 150x of a crosswise-mixed type and of a constant height with an axial vector $\vec{n}$, comprising: a vertical limiting electrode 151xn; first and second electrodes of reflection 151x and 152x; third electrodes 153x; horizontal constituents 154x and 154xs1 which are lateral constituents of a fourth electrode; and horizontal constituents 155x and 155xs1 which are lateral constituents of a fifth electrode. FIG. 166 shows a module of reflection 160x of a box-mixed type and of a constant height with an axial vector $\vec{n}$, comprising: a vertical limiting electrode 161xn; a first electrode of reflection 161x; a second electrode of reflection 162x; a third box-type electrode 163x; a fourth box-type electrode 164x; and a fifth box-type electrode 165x of P-module of reflection 160x.

Figure 167:
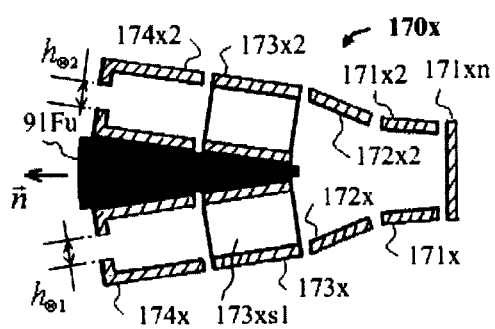

In any vertical two-zone P-element of reflection with a vertical limiting electrode, including extended P-elements of reflection, each zone may be arranged to some extent irrespectively of other zones, considering the above mentioned design multiplicity of P-elements of reflection. FIG. 167 shows, in an elevation profile, a doubly mixed type vertical two-zone symmetrical two-pitch height P-element of reflection 170x with an axial vector $\vec{n}$, comprising: a vertical limiting electrode 171xn; a first electrode of reflection including constituents 171x and 171x2; a second electrode of reflection including constituents 172x and 172x2; a third cross-wise electrode 173x of a lower zone and an electrode 173xs1 which is one of its lateral constituents; a fourth electrode 174x of the lower zone with an input diaphragm; a third box-type electrode 173x3 of an upper zone; a fourth electrode 174x2 of the upper zone with an input diaphragm; and an inter-band substrate of electrodes 171xu.

All the above mentioned design options for P-elements are related to their vertical sections. Additionally, each such P-element also has a wide variety of design alternatives in implementation of horizontal electrode configurations.

Figure 168:
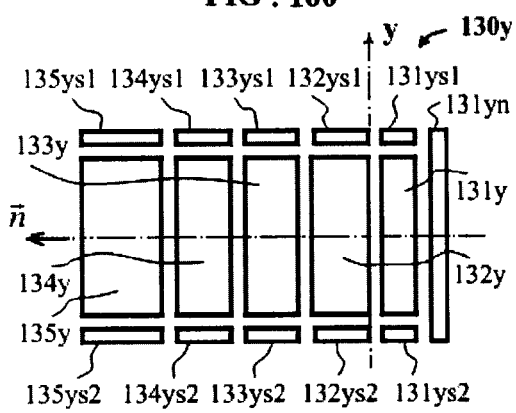
Figure 175:
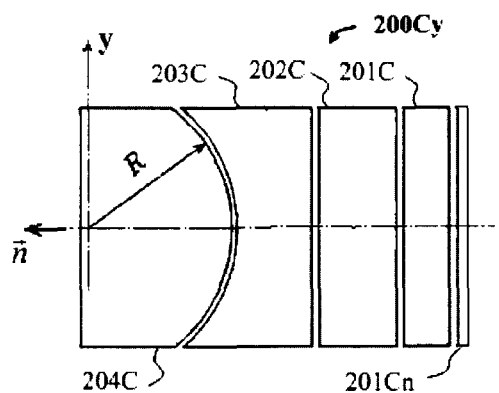
Figure 176:
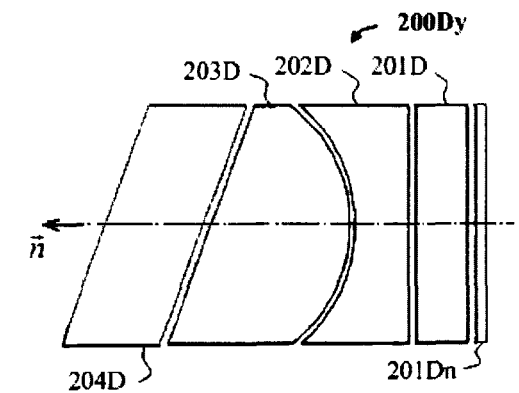
Figure 177:
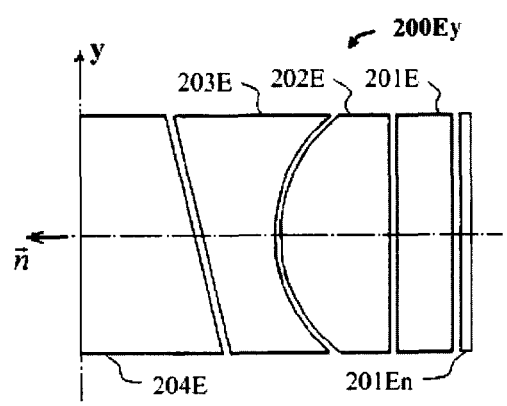
Figure 178:
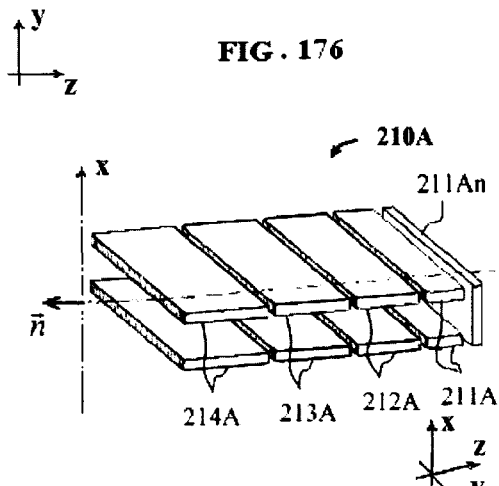
Figure 179:
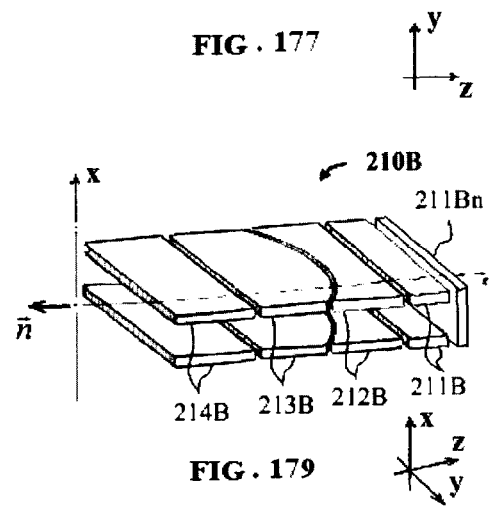
Figure 180:
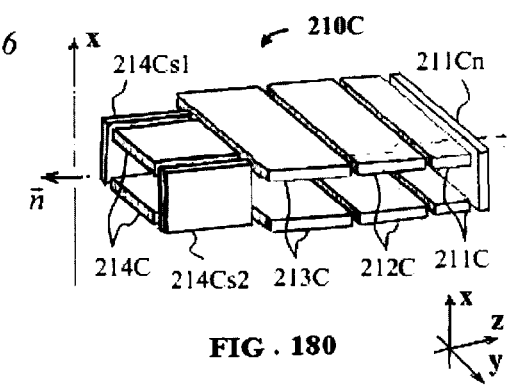
Figure 181:
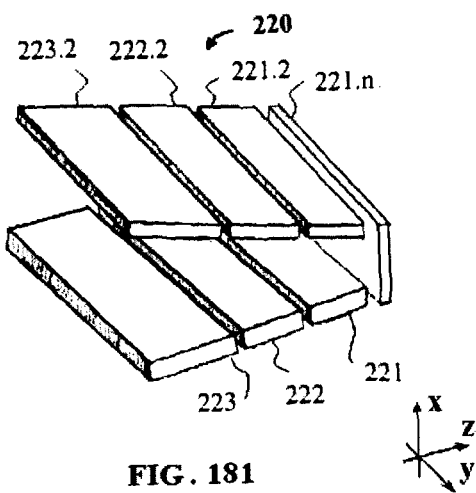
Figure 182:
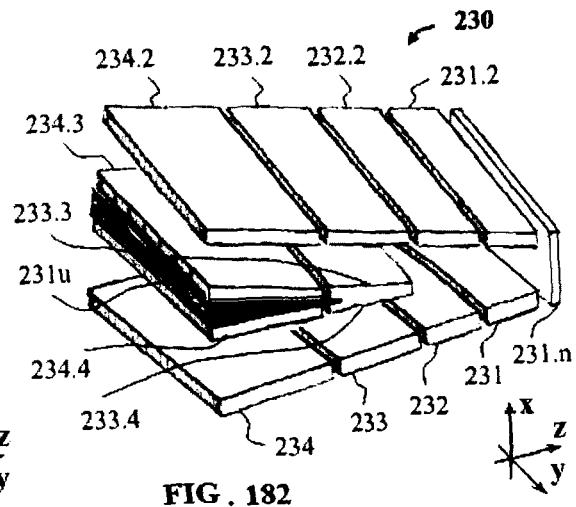
Figure 183:
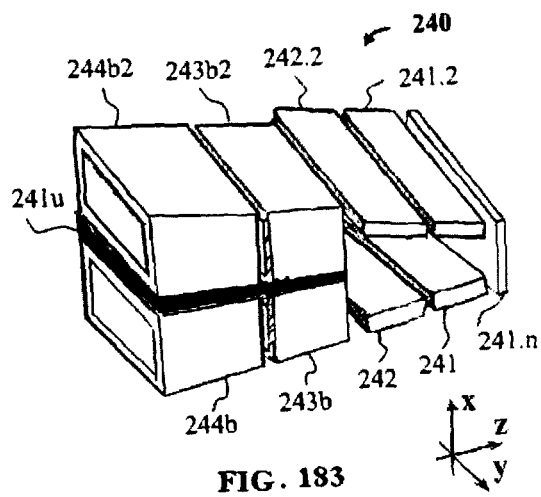

To explain the design multiplicity in implementation of horizontal electrode configurations, the P-elements of reflection 130y, 150y, 160y, 180y, 190y, 200Ay, 200By, 200Cy, 200Dy and 200Ey are shown in FIGS. 168 to 177, respectively, in projections on horizontal planes coinciding with plane yz of a rectangular Cartesian coordinate system. FIGS. 172 to 177 show examples of performance of IO mirror central bands (lateral sides and sectors are truncated), in a schematic view. FIG. 168 shows a crosswise type (with lateral electrode constituents) P-element of reflection 130y, which is one version of IO element of reflection whose xz projection 130x is shown in FIG. 163, with an axial vector $\vec{n}$, comprising: a vertical limiting electrode 131yn; a horizontal constituent 131y (another horizontal constituent is not shown), and lateral constituents 131ys1, and 131ys2 of a first electrode of reflection; a horizontal constituent 132y and lateral constituents 132ys1 and 132ys2 of a second electrode of reflection; a horizontal constituent 133y and lateral constituents 133ys1 and 133ys2 of a third electrode; a horizontal constituent 134y and lateral constituents 134ys1 and 134ys2 of a fourth electrode; and a horizontal constituent 135y and lateral constituents 135ys1 and 135ys2 of a fifth electrode. FIG. 169 is shows a crosswise-mixed type P-element of reflection 150y, which is one version of P-element of reflection whose xz projection 150x is shown in FIG. 165, with an axial vector $\vec{n}$, comprising: a vertical limiting electrode 151yn; a first electrode of reflection 151y of a Cartesian two-dimensional type; a second electrode of reflection 152y of a Cartesian two-dimensional type; a third electrode 153y of a Cartesian two-dimensional type; a horizontal constituent 154y and lateral constituents 154ys1 and 154ys2 of a fourth electrode; and a horizontal constituent 155y and lateral constituents 155ys1 and 155ys2 of a fifth crosswise type electrode. FIG. 170 shows a box-mixed type of P-element of reflection 160y, which is one version of P-element of reflection whose xz projection 160x is shown in FIG. 166, with an axial vector $\vec{n}$, comprising: a vertical limiting electrode 161yn; a first electrode of reflection 161y of a Cartesian two-dimensional type; a second electrode of reflection 162y of a Cartesian two-dimensional type; a third box-type electrode 163y; a fourth box-type electrode 164y; and a fifth box-type electrode 165y. FIG. 171 shows a P-element of reflection 180y of constant height of a Cartesian two-dimensional type with an axial vector $\vec{n}$, comprising: a vertical limiting electrode 181yn; first and second electrodes of reflection 181y and 182y; a third electrode 183y; fourth and fifth electrodes 184y and 185y. FIG. 172 shows a sector of a P-element of reflection 190y with an axial vector $\vec{n}$, comprising: a vertical limiting electrode 191yn; constituents of first and second reflecting electrodes 191y and 192y; and constituents of third and fourth electrodes 193y and 194y. Electrode slots between the constituents of the third and fourth electrodes 193y and 194y are arranged rectilinearly and at an angle relative to other inter-electrode slots, which are arranged rectilinearly and parallel to the vertical plane of the IO element. FIG. 173 shows a sector of a P-element of reflection 200Ay with an axial vector $\vec{n}$, comprising: a vertical limiting electrode 201An; constituents of first and second reflecting electrodes 201A and 202A; and constituents of third and fourth electrodes 203A and 204A. An electrode slot between the constituents of second and third electrodes 202A and 203A is configured as a sector of a second-order curve whose plane of symmetry coincides with the vertical plane of the IO element. Other inter-electrode slots are arranged rectilinearly and vertically to the vertical plane of the P-module. FIG. 174 shows a sector of a reflecting module 200By with an axial vector $\vec{n}$, comprising: a vertical limiting electrode 201Bn; constituents of first and second reflecting electrodes 201B and 202B; and third and fourth electrodes 203B and 204B. Inter-electrode slots between the constituents of second and third electrodes 202B and 203B, and third and fourth electrodes 203B and 204B are configured as sectors of differently directed second-order curves whose planes of symmetry coincide with a vertical plane of the P-element. Other inter-electrode slots are arranged rectilinearly and vertically relative to the vertical plane of the P-module. FIG. 175 shows a sector of a reflecting module 200y with an axial vector $\vec{n}$, comprising: a vertical limiting electrodes 201Cn; constituents of first and second reflecting electrodes 201C and 202C; and constituents of third and fourth electrodes 203C and 204C. Electrode slots between the constituents of third and fourth electrodes 203C and 204C are configured as sectors of differently directed second-order curves whose planes of symmetry coincide with the vertical plane of the IO element. Other inter-electrode slots are arranged rectilinearly and vertically relative to the vertical plane of the IO element. FIG. 176 shows the sector of a reflecting module 200Dy with an axial vector $\vec{n}$, comprising: a sector of a vertical limiting electrode 201Dn; sectors of constituents of first and second reflecting electrodes 201D and 202D; and sectors of third and fourth electrodes 203D and 204D. Electrode slots between the constituents of the second and third electrodes 202D and 203D are configured as sectors of a second-order curve with curvature oriented towards vertical limiting electrode 201Dn, and whose plane of symmetry coincides with the vertical plane of the IO element. Electrode slots between the constituents of third and fourth electrodes 203D and 204D are arranged rectilinearly and at an angle relative to the vertical plane of the IO element. Other inter-electrode slots are arranged rectilinearly and vertically relative to the vertical plane of the IO element. FIG. 177 shows a sector of a reflecting module 200Ey with an axial vector $\vec{n}$, comprising: a vertical limiting electrode 201En; constituents of first and second reflecting electrodes 201E and 202E; and constituents of third and fourth electrodes 203E and 204E. Electrode slots between the constituents of second and third electrodes 202E and 203E are configured as sectors of a second-order curve with curvature oriented towards vertical limiting electrode 201En, whose plane of symmetry coincides with the vertical plane of the IO element. Electrode slots between the constituents of third and fourth electrodes 203E and 204E are arranged rectilinearly and at an angle relative to the vertical plane of the IO element. Other inter-electrode slots are arranged rectilinearly and vertically relative to the vertical plane of the IO element. FIGS. 178 to 183 show volume images with vertical limiting electrodes of P-elements of reflection 210A, 200B, 210C, 220, 230 and 240, respectively, consistent with some versions of reflecting modules whose engineering solutions are shown above in their projections on xz and yz. FIGS. 178, 179, and 180 show volume images of mirrors 210A, 210B, and 210C, respectively. In these figures, the effective (inner) surfaces of electrodes have non-uniform height and are arranged on planes parallel to each other and to the mean plane, which coincides with coordinate plane yz. The mean plane of every IO element is a plane of electrode symmetry, and the axial vector $\vec{n}$ is located on the mean plane. FIGS. 181, 182, and 183 show volume images of single pitch height P-elements of reflection 220, 230 and 240, respectively, in which inter-electrode slots are arranged rectilinearly and vertically relative to a longitudinal-vertical plane of the IO mirrors. FIG. 178 shows a Cartesian two-dimensional type P-element of reflection 210A, comprising: a vertical limiting electrode 211An; first and second reflecting electrodes 211A and 212A; and third and fourth electrodes 213A and 214A. FIG. 179 shows a trans-axial-bending mixed type local P-element of reflection 210B, comprising: a vertical limiting electrode 211Bn, first and second electrodes of reflection 211B and 212B; and third and fourth electrodes 213B and 214B. Electrode slots between constituents of the second and third electrodes 212B and 213B are configured as sectors of a second-order curve whose plane of symmetry coincides with the vertical plane of the IO element. Other inter-electrode slots are arranged rectilinearly and vertically relative to the vertical plane of local P-element of reflection 210B. FIG. 180 shows a crosswise-mixed type P-element of reflection 210C, comprising: a vertical limiting electrode 211Cn; first and second electrodes of reflection 211C and 212C; a third electrode 213C; and a fourth electrode 214C and its lateral constituents 214$ys$1 and 214$ys$2. FIG. 181 shows a Cartesian two-dimensional type single-pitch-width P-element of reflection 220, comprising: a vertical limiting electrode 221.$n$, a first electrode of reflection including constituents 221 and 221.2; a second electrode of reflection including constituents 222 and 222.2; and a third electrode of reflection including constituents 223 and 223.2. The effective (inner) electrode surfaces of module of reflection 220 have a single pitch: the upper constituents of all electrodes are arranged at an angle relative to surfaces of the lower electrode constituents. FIG. 182 shows a vertical two-zone Cartesian two-dimensional type single-pitch-width P-element of reflection 230, comprising: a vertical limiting electrode 231.$n$; a first electrode of reflection including constituents 231 and 231.2; a second electrode of reflection including constituents 232 and 232.2; a third electrode of a lower zone including constituents 233 and 233.4; a third electrode of an upper zone including constituents 233.2 and 233.3; a fourth electrode of the upper zone including constituents 234.2 and 234.3; and an inter-band substrate of electrodes 231$u$. The effective (inner) electrode surfaces of vertical two-zone module of reflection 230 have a single pitch: the upper electrode constituents are arranged at an angle relative to the lower electrode constituents, which are arranged in one plane perpendicularly to the plane of vertical limiting electrode 231.$n$. FIG. 183 shows a vertical two-zone crosswise-mixed type single-pitch-height local P-element of reflection 240, comprising: a vertical limiting electrode 241.$n$; a first electrode of reflection including constituents 241 and 241.2; a second electrode of reflection including constituents 242 and 242.2; a third electrode of a lower zone including constituents 243 and 243.4; a third electrode of an upper zone including constituents 243.2 and 243.3; a fourth electrode of the upper zone including constituents 244.2 and 244.3; and an inter-band substrate of electrodes 241$u$. The first and second electrodes are of a Cartesian two-dimensional type; the third and fourth electrodes are of a box-type.

Figure 184:
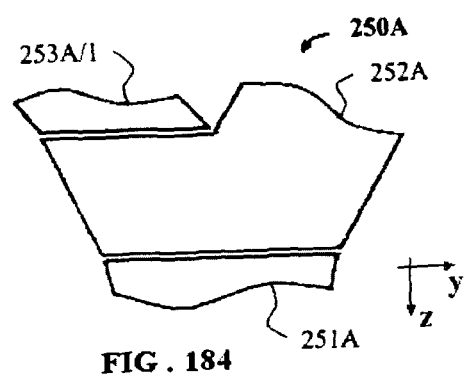
Figure 185:
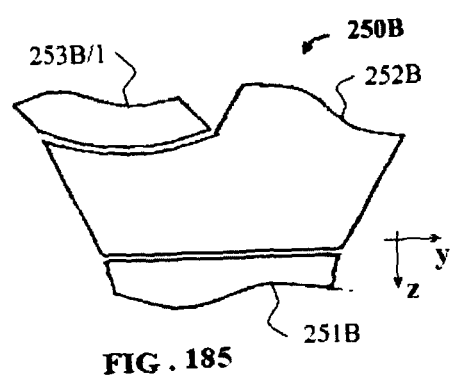

FIGS. 184, 185, 186, and 187 represent a schematic view of examples illustrating performance of horizontal two-zone local P-elements in projections on the plane yz. For brevity, examples are shown only for local P-elements of reflection in which inter-electrode slots are arranged rectilinearly and parallel to each other. FIGS. 184 and 185 represent examples of sectors within an area of branching of IO mirror zones. FIGS. 186 and 187 represent examples of growth, i.e., implementing of horizontal two-zone local P-elements of reflection as a whole based on the P-elements' specified areas of zone branching.

FIG. 184 represents a sector of a reflecting module 250A, comprising: a reflecting module 250By; constituents of first and second reflecting electrodes 251A and 252A; and a sector (constituent) of a third electrode 253A/1 of a left zone. Inter-electrode slots between the constituents of second and third electrodes 252A and 253A/1, as well as between the constituents of first and second electrodes 251A and 252A, are arranged rectilinearly and vertically relative to the longitudinal-vertical plane of module of reflection 250A.

FIG. 185 represents a sector of a reflecting module 250By, comprising: constituents of first and second reflecting electrodes 251B and 252B; and a sector of third electrode 253B/1 of a left zone. Electrode slots between the constituents of second and third electrodes 252B and 253B/1 are configured as a sector of a second-order curve with curvature oriented away from the side of ion reflection. Electrode slots between the constituents of first and second electrodes 251B and 252B are arranged rectilinearly and vertically relative to the vertical plane of reflecting module 250By.

FIG. 186 represents a P-element of reflection 250Cy, comprising: a vertical limiting electrode 251C.n, constituents of first and second reflecting electrodes 251C and 252C; constituents of third and fourth electrodes 253C/1 and 254C/1 of a left zone; constituents of a third electrode 253C/2 of a right zone; a horizontal constituent 254C/2 and lateral constituents 154C/s1 and 154C/s2 of a fourth crosswise type electrode of the right zone. Inter-electrode slots between electrode constituents are arranged rectilinearly and vertically relative to the vertical plane of the IO element.

FIG. 187 represents a P-element of reflection 250Dy, comprising: a vertical limiting electrode 251D.n; constituents of first and second reflecting electrodes 251D and 252D; constituents of third and fourth electrodes 253D/1 and 254D/1 of a left zone; and constituents of third and fourth electrodes 253D/1 and 254D/2 of a right zone. Inter-electrode slots between the constituents of the second electrode 252D and the third electrode of the right zone 253D2, as well as between the second electrode 252D and the third electrode of the left zone 253D/1, are configured as differently directed second-order curve sectors, whose plane of symmetry coincides with the vertical plane of the IO element. Other inter-electrode slots are arranged rectilinearly and vertically relative to the vertical plane of the IO element.

In the examples of growth shown in FIGS. 186 and 187, the illustrated implementation of horizontal two-zone P-elements of reflection based on specified areas of zone branching of the P-elements, are particular examples. The implementation of each zone may be as versatile as was above described for the P-element of reflection, independently of the implementation of other zones.

Figure 189:
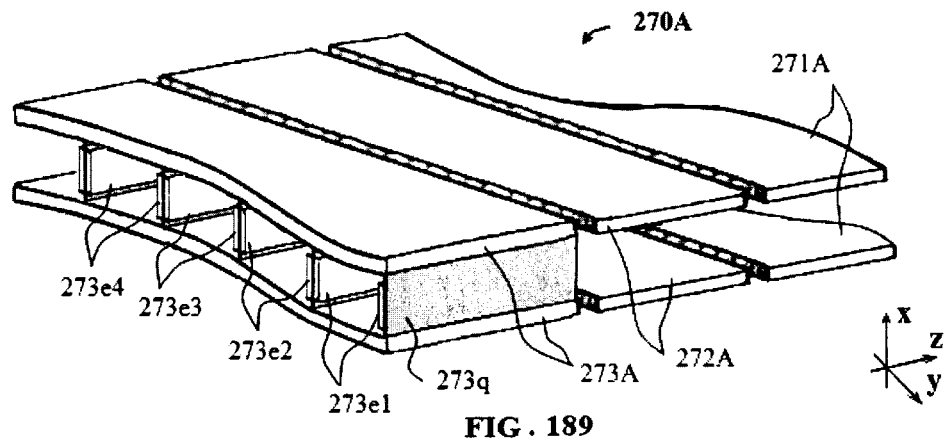
Figure 190:
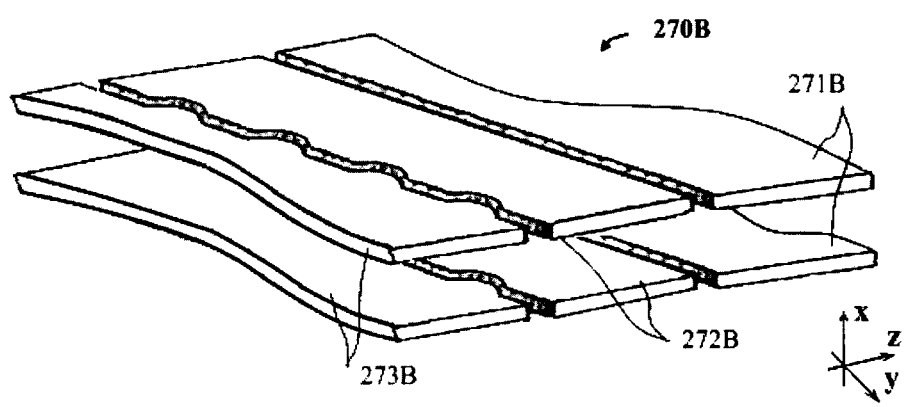
Figure 191:
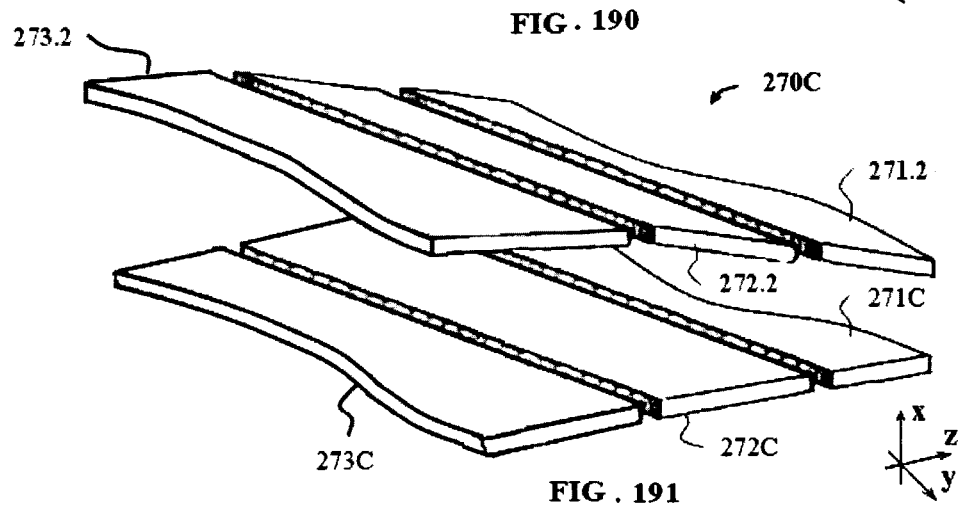
Figure 192:
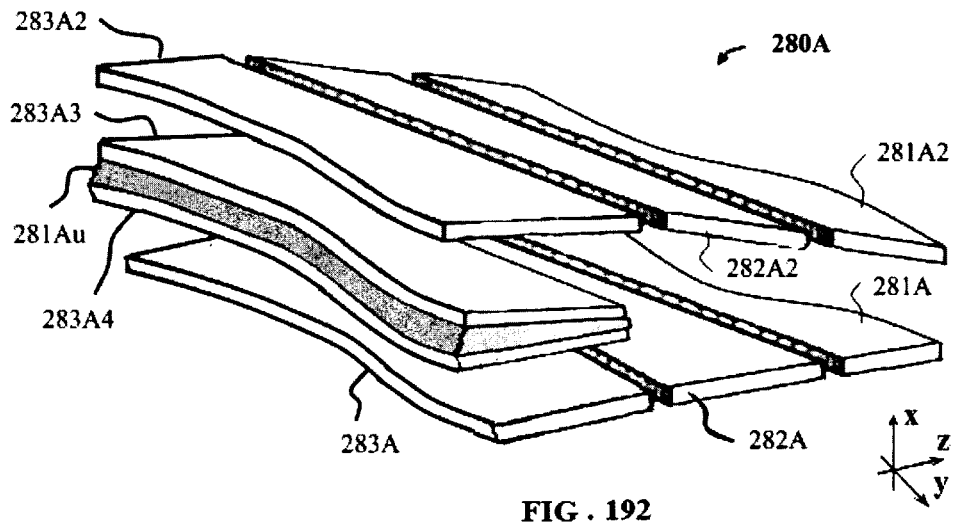
Figure 193:
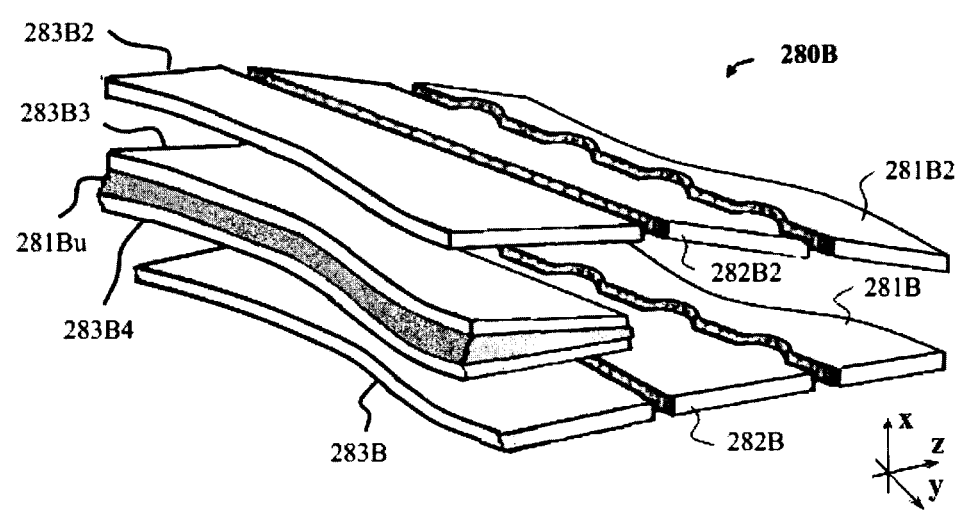

FIGS. 188 to 193 schematically represent examples of electrode implementation for certain types of extended P-elements of reflection: FIG. 188 represents a sector of an extended P-element of reflection 260 in projection on the incremental plane, which coincides with the coordinate plane yz;

FIGS. 189, 190, and 191 represent volume space images of some line sectors of IO element mirrors with constant widths; and FIGS. 192 and 193 represent volume space images of sectors of some vertical two-zone linear mirrors.

FIG. 188 represents a projection on the incremental plane, which coincides with the coordinate plane yz, of a trans-bending rectilinearly alternating extended P-element of reflection 260 with constant width, comprising: a vertical limiting electrode 261yn; first and second electrodes of reflection 261y and 262y; and third, fourth and fifth electrodes 263y, 264y, and 265y, respectively. Electrode slots between the constituents of the second and third electrodes 262y and 263y are configured as a recurrent combination of a rectilinear sector and a sector of a second-order curve. Other inter-electrode slots are arranged in straight lines vertically to the mean and vertical planes of linear P-element of reflection 260y.

FIG. 189 represents a crosswise type of a constant-height sector of an extended P-element of reflection 270A having lateral electrode constituents, comprising sectors of first, second, and third electrodes 271A, 272A, and 273A. Electrode slots are arranged rectilinearly and vertically relative to the longitudinal-vertical plane of the sector of extended P-element of reflection 270A. Electrode 273A includes a group of inner lateral constituents 273e.

FIG. 190 represents a trans-bending rectilinearly alternating sector of an extended P-element of reflection 270B with a constant height, comprising sectors of first, second, and third electrodes 271B, 272B, and 273B. Electrode slots between the constituents of the second and third electrodes 272B and 273B are configured as a recurrent combination of a rectilinear section and a sector of a second-order curve. Other inter-electrode slots are arranged rectilinearly and vertically relative to the longitudinal-vertical plane of a sector of the extended P-element of reflection 270B. FIG. 191 shows a single-pitch height sector of an extended P-element of reflection 270C, comprising sectors of first, second and third box-type periodic electrodes 271C, 272C, and 273C. All electrode slots between the electrodes are arranged rectilinearly and vertically relative to the longitudinal-vertical plane of a sector of the extended P-element of reflection 270C. FIG. 192 shows a Cartesian two-dimensional type single-pitch height vertical two-zone sector of an extended P-element of reflection 280A, comprising: a first electrode including constituents 281A and 281A2; a second electrode including constituents 282A and 282A2; a third electrode of a lower zone including constituents 281A and 281A2; a third electrode of an upper zone including constituents 281A and 281A2; and a substrate of inter-band electrode 281Au. The effective (inner) electrode surfaces are configured with a single-pitch: the upper and lower zones of electrodes are arranged at an angle relative to each other. All electrode slots between the electrodes are arranged rectilinearly and vertically relative to the vertical plane of the two-zone sector of the linear mirror of reflecting module 280A. FIG. 193 shows a trans-bending rectilinearly alternating type single-pitch height vertical two-zone sector of an extended P-element of reflection 280B, comprising: a first electrode including constituents 281B and 281B2; a second electrode including constituents 282B and 282B2; a third electrode of a lower zone including constituents 281B and 281B2; a third electrode of an upper zone including constituents 281B and 281B2; and a substrate of inter-band electrodes 281Bu. The effective (inner) electrode surfaces are configured with a single pitch: the upper and lower electrode zones are arranged at an angle relative to each other. Electrode slot between the constituents of the first and second electrodes 281B and 282B is configured as a recurrent combination of a rectilinear section and a segment of a second-order curve. Other inter-electrode slots are arranged rectilinearly and vertically relative to the vertical plane of linear IO mirror 260.

FIGS. 189 to 193 represent only some examples of sectors of extended P-elements. Extended P-elements may be configured not only in the described modes, but also in combinations with local P-elements as shown in FIGS. 153 to 187.

Figure 194:
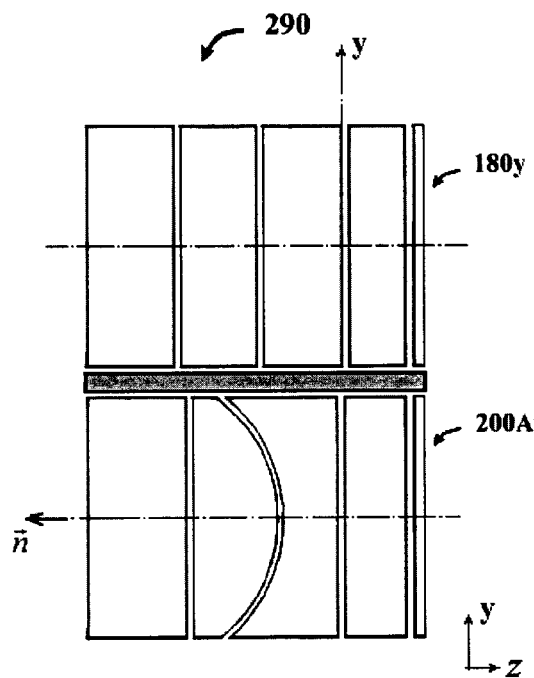

FIG. 194 represents an yz projection of a non-uniform (comprising mirrors of at least two different types) extended horizontal array of IO mirrors, comprising two IO mirrors, and having a Cartesian two-dimensional IO mirror 180y with a vertical limiting electrode, as described in FIG. 171, and a trans-bending mixed IO mirror 200Ay with a vertical limiting electrode, as described in FIG. 173Ay, arranged in series.

Figure 195:
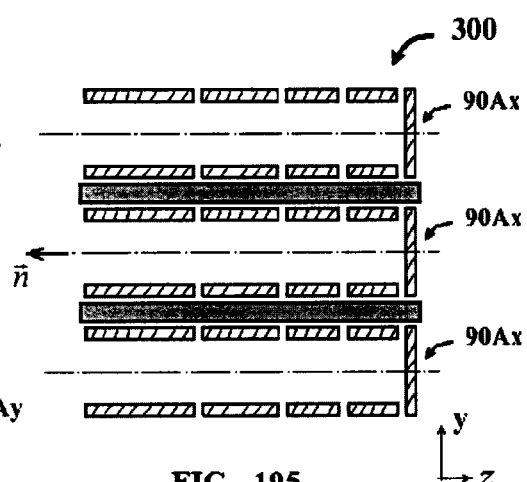

FIG. 195 represents an xz projection of a uniform (comprising mirrors of identical type) extended vertical array of IO mirrors comprising three mirrors wherein three identical mirrors shown in a longitudinal elevation profile are arranged in series.

The examples illustrated in FIGS. 194 and 195 give a general representation of notions concerning extended horizontal and vertical, uniform and non-uniform, extended arrays of IO mirrors. In general, the decision regarding the number of mirrors in the array and use of different mirrors in the array depends on the practical problem to be solved by mass spectroscopy. Mirrors in the array may be selected from the group comprising diversiform designs of IO mirrors as shown above.

Other alternatives of IO element configurations include IO elements built by making changes to the geometry of the IO elements shown above, e.g., leading to changes of their projections on the xz plane, such as configuring the IO elements without a vertical limiting electrode and/or with a different number of electrodes, or configuring the IO elements with different combinations of electrode configurations.

The mode of operation is decided based on the electric potential distribution at the electrodes: any one of versions of IO elements shown above operates as a module of reflection; some versions of IO elements that do not include vertical limiting electrodes may operate in a module of reflection regime or in any other mode, including in a multifunctional mode.

FIGS. 196 to 206 represent, in a schematic view, examples of IO elements arranged without a vertical limiting electrode as particular cases of IO elements shown above with vertical limiting electrodes.

Figure 196:
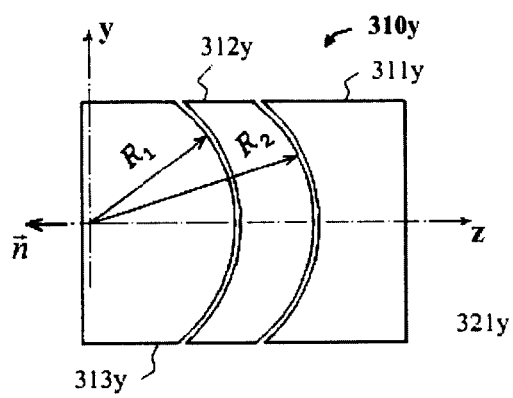

FIG. 196 represents a yz projection of an IO element 310y, comprising constituents of trans-axial type electrodes 311y, 312y and 313y. The gap between the electrodes is configured as segments of two thin concentric rings with inner radii $R_1$ and $R_2$.

Figure 197:
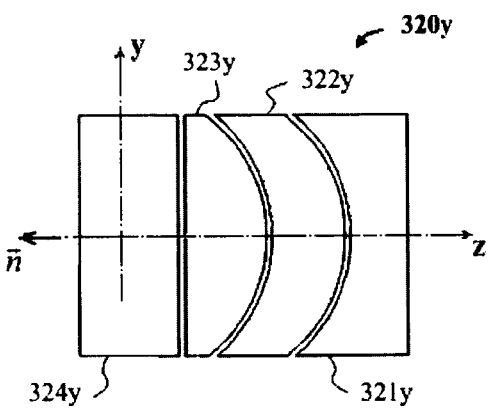
Figure 198:
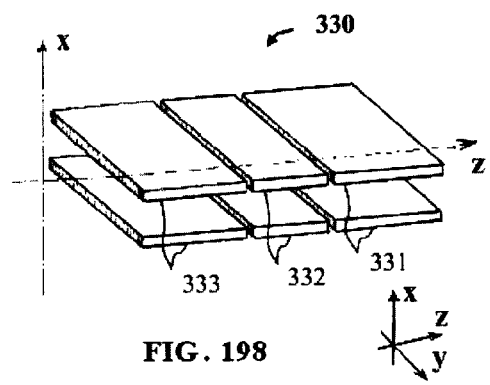

FIG. 197 represents a yz projection of an IO element 320y, comprising constituents electrodes 321y, 322y, 323y and 324y. Gaps between the first and second electrodes 321y and 322y, as well as between the second and third electrodes 322y and 323y, are configured as segments of two thin concentric rings. A gap between the third and fourth electrodes 323y and 324y are configured as a rectilinear fine slot, perpendicular to the axial vector $\dot{n}$. FIG. 198 shows a space pattern of a three-electrode Cartesian two-dimensional P-element 330, built on the basis of changes to P-element of reflection 210 shown in FIG. 178, but arranged without a vertical limiting electrode or a fourth electrode. P-element 330 comprises: first, second and third electrodes 331, 332, and 333.

Figure 199:
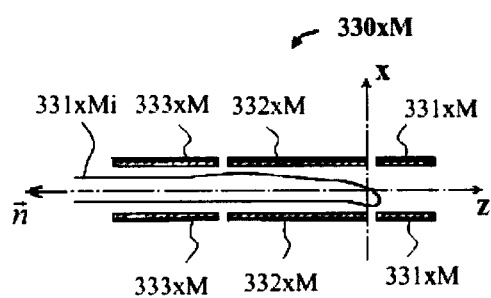

FIG. 199 represents, in an elevation profile on a vertical plane coinciding with coordinate plane xz, a P-module 330xM, which is an xz projection of P-element 330, and two characteristic ion motion trajectories 331xMi, which occur during operation of P-module 330xM in a mode of a P-module of reflection, when first, second and third electrodes 331xM, 332xM, and 33xM, are provided.

Figure 200:
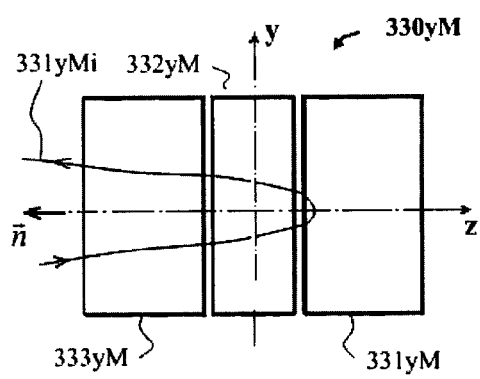
Figure 201:
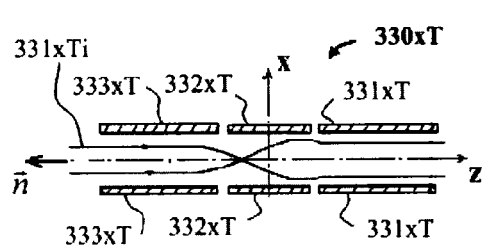

FIG. 200 represents, in a horizontal plane coinciding with coordinate plane yz, a P-module 330yM, which is a yz projection P-element 330, and two characteristic ion motion trajectories 331yMi which occur during operation of P-module 330yM in a mode of reflection, when a first electrode 331yM, a second electrode 332yM, and a third electrode 333yM are provided. FIG. 201, represents an elevation profile on a vertical plane coinciding with coordinate plane xz, of a P-element 330xT which is a xz projection of P-element 330, and two characteristic ion motion trajectories 331xTi which occur during operation of P-element 330xT in telescopic mode, when a first electrode 331xT, a second electrode 332xT, and a third electrode 333xT are provided.

Figure 202:
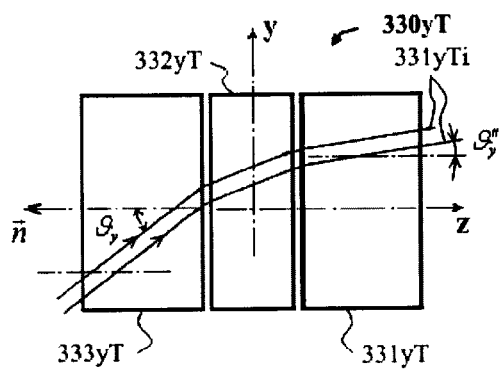

FIG. 202 represents, in a horizontal plane coinciding with coordinate plane yz, a P-element 330yT which is a yz projection of P-element 330, and two characteristic ion motion trajectories 331yTi which occur during its operation in telescopic mode, when a first electrode 331yT, a second electrode 332yT, and a third electrode 333yT are provided.

Figure 203:
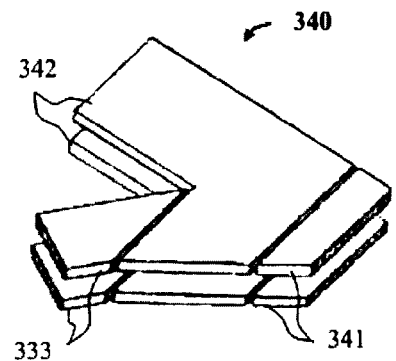

FIG. 203 represents a space pattern of a three-electrode Cartesian two-dimensional horizontal two-zone P-element 340, built on the basis of P-element of reflection 250A shown in FIG. 184, but arranged without a vertical limiting electrode. The P-element 340 comprises: a first electrode 341, a second electrode 342 and a third electrode 343.

Figure 204:
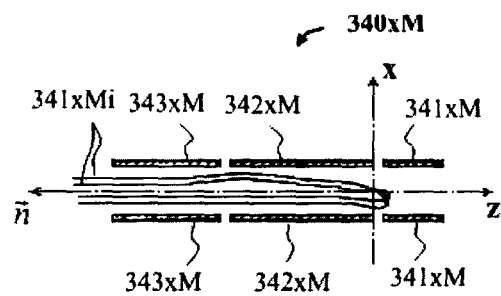

FIG. 204 represents, in an elevation profile on vertical plane coinciding with coordinate plane xz, a horizontal two-zone P-element 340xM which is a xz projection of P-element 340, and two characteristic ion motion trajectories 341xMi which occur during operation of P-element 340xM in a mode of reflection, when a first electrode 341xM, a second electrode 342xM, and a third electrode 343xM are provided.

Figure 205:
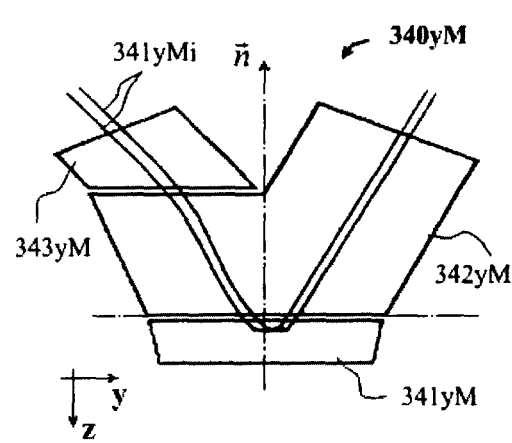

FIG. 205 represents, in a horizontal plane coinciding with coordinate plane yz, a horizontal two-zone P-element 340yM which is a yz projection of P-element 340, and two characteristic ion motion trajectories 341yMi which occur during operation of P-element 340yM in a mode of reflection, when a first electrode 341yM, a second electrode 342yM, and a third electrode 343yM are provided.

Figure 206:
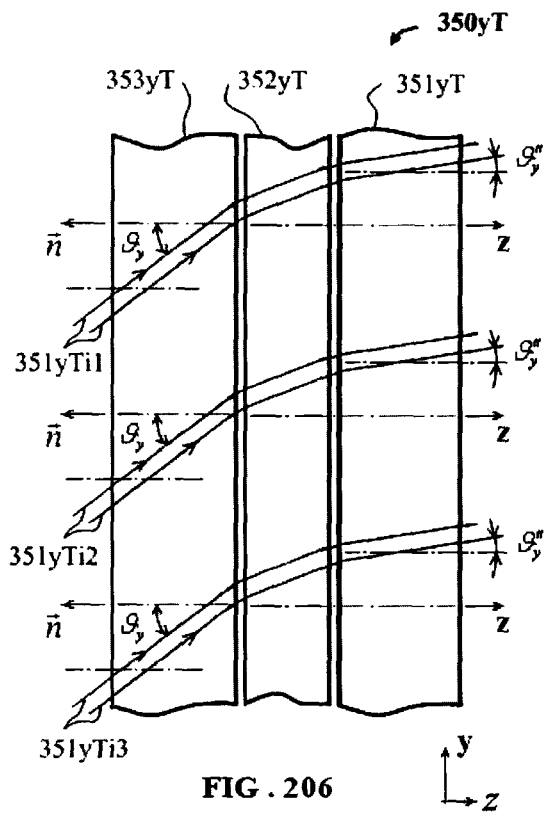

FIG. 206 represents, in an incremental plane coinciding with plane yz, a Cartesian two-dimensional sector 350yT of an extended P-element, including sectors of a first electrode 351yT, a second electrode 352yT, and a third electrode 353yT, as well as characteristic ion trajectories 351xMi1, 351xMi2, and 351xMi3 which occur in sector 350yT during operation of the P-element in telescopic mode, an angle of ion flux dip $\vartheta'_y$, and an angle of ion flux refraction $\vartheta''_y$.

FIGS. 207 to 210 represent schematic examples of implementations of two-set P-elements 360A, 360B, 370 and 370y, without vertical limiting electrodes.

Figure 207:
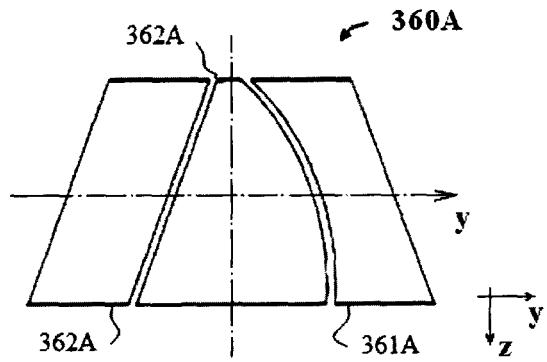

FIG. 207 represents a P-element 360A, in which a gap spacing between a first electrode 361A and a second electrode 362A is configured as a segment of a thin ring, a gap spacing between the second electrode 362A and a third electrode 363A is configured as a rectilinearly fine slot which is non-perpendicular to coordinate axis y.

Figure 208:
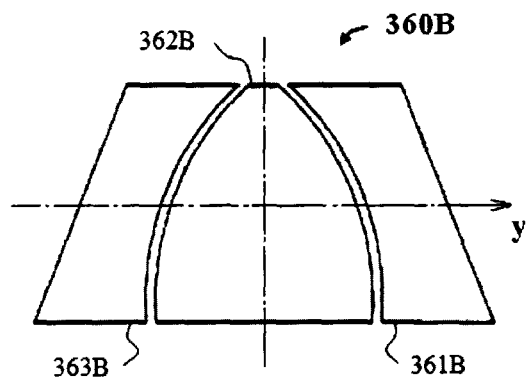

FIG. 208 represents a P-element 360B, in which gap spacings between a first electrode 361B and a second electrode 362B and between the second electrode 362B and a third electrode 363B are configured as segments of two thin rings, which are not symmetric relative to the coordinate axis y.

Figure 209:
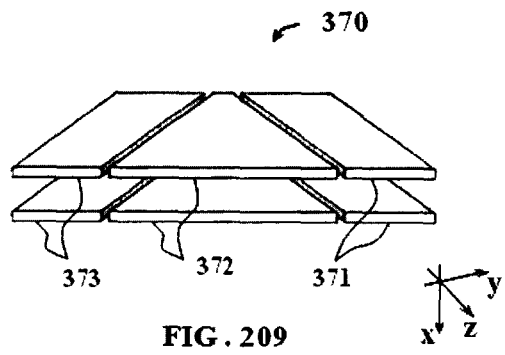

FIG. 209 represents a P-element 370, wherein gap spacings between a first electrode 371 and a second electrode 372, and between the second electrode 372 and a third electrode 373 are configured as straight-line thin slots, which are not symmetric relative to coordinate axis y.

Figure 210:
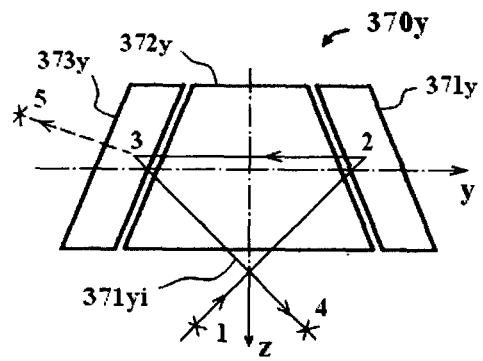

FIG. 210 represents, in a horizontal plane coinciding with coordinate plane yz, a P-element 370y which is a yz projection of P-element 370. When a first electrode 371y and a second electrode 372y, as well as the second electrode 372y and a third electrode 373y, are used in a mode of reflection, they are characterized by the ion motion trajectory 371yi passing through points 1, 2, 3, and 4 in the P-element 370y. When the first electrode 371y and the second electrode 372y are used in a mode of reflection, while the second electrode 372y and third electrode 373y are used in a mode of refraction, then the characteristic ion motion trajectory 371yi passes through points 1, 2, 3 and 5 in the P-element 370y. Coupled P-elements may be used in a mode of double mirror, in a mode of refraction-reflection, and in a multifunctional mode.

Figure 211:
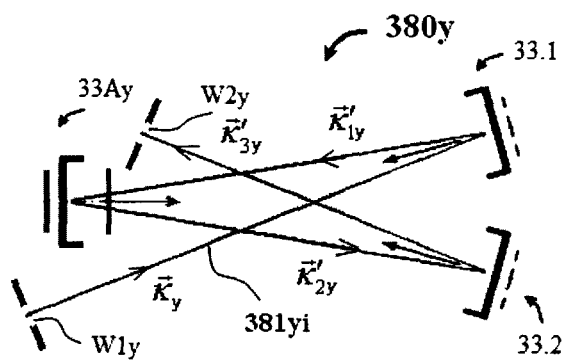
FIGS. 211-232 represent diagrams of IO reflection arrangements with a curved main axis useful with TOF IB-channels.
Figure 212:
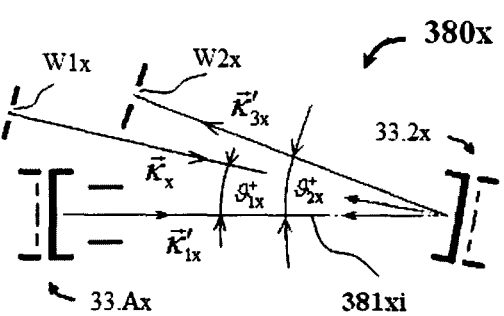
Figure 213:
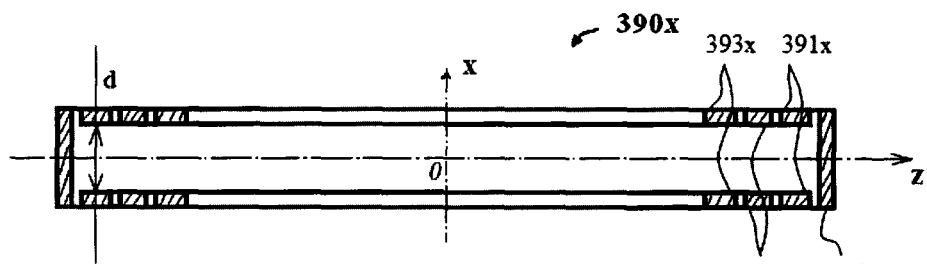

To build an IO channel system in a multireflecting mode or in a mode with a curved main axis, one or more of the control subsystems shown in FIGS. 135 to 151 may be used, and/or one or more P-elements, in particular, those shown in the preceding figures. FIGS. 211 and 212 show an IO diagram of a three-reflecting time-of-flight-dispersing (TOF) IB-channel in projections on coordinate plane yz and xz, respectively. FIG. 211 shows:

a three-reflecting IB-channel 380y;
three single-zone local P-elements of reflection 33.1, 33Ay, and 33.2;
an input gate W1y;
an output gate;
an averaged trajectory 381yi of motion of ion packets including: a dip vector and input $\vec{K}_y$; a vector of first reflection $\vec{K}'_{1y}$; a vector of second reflection $\vec{K}'_{2y}$; and a vector of third reflection and output $\vec{K}'_{3y}$. FIG. 212 shows:

a three-reflecting IB-channel 380x;
three single-zone local P-elements of reflection 33.1, 33Ax, and 33.2;
an input gate W1x;
an output gate W2x;
an averaged trajectory 381xi of motion of ion packets including: a dip vector and input $\vec{K}_x$; a vector of first reflection $\vec{K}'_{1y}$; a vector of second reflection $\vec{K}'_{2x}$; and a vector of third reflection and output $\vec{K}'_{3x}$;

an angle of ion flux input-reflection $\vartheta'_{1x}$ relative to the first local P-element of reflection 33.1; and an angle of ion flux input-reflection $\vartheta'_{3x}$ relative to the third P-element of reflection 33.2. FIGS. 213 to 217 show flat P-multireflectors of wide configuration for TOF IB-channels in projections on the coordinate plane. In FIG. 213 the elevation profile in a vertical plane of a single type of second-order curvilinear P-multireflector 390x is shown. P-multireflector 390x includes four electrodes 391xn, 391x, 392x and 393x and has a distance d between electrode linings.

Figure 214:
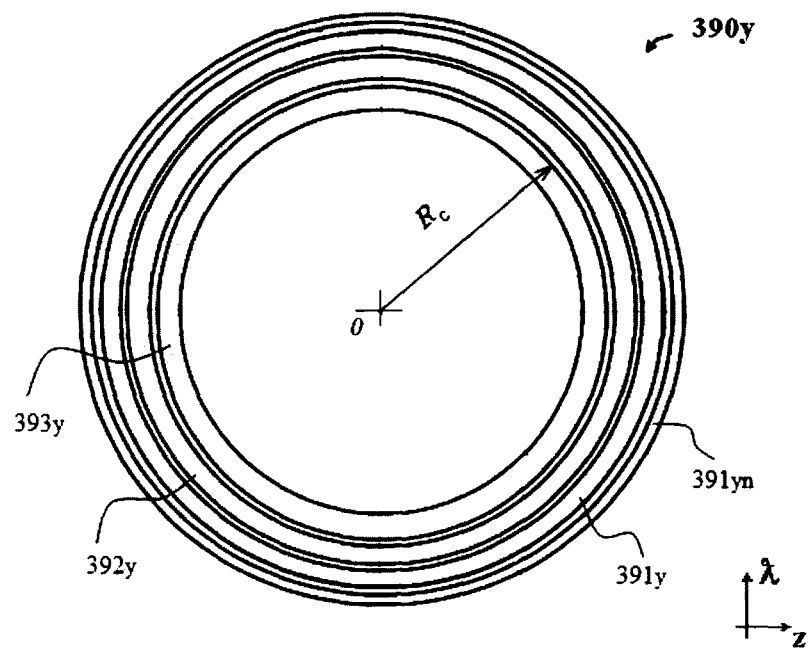
Figure 215:
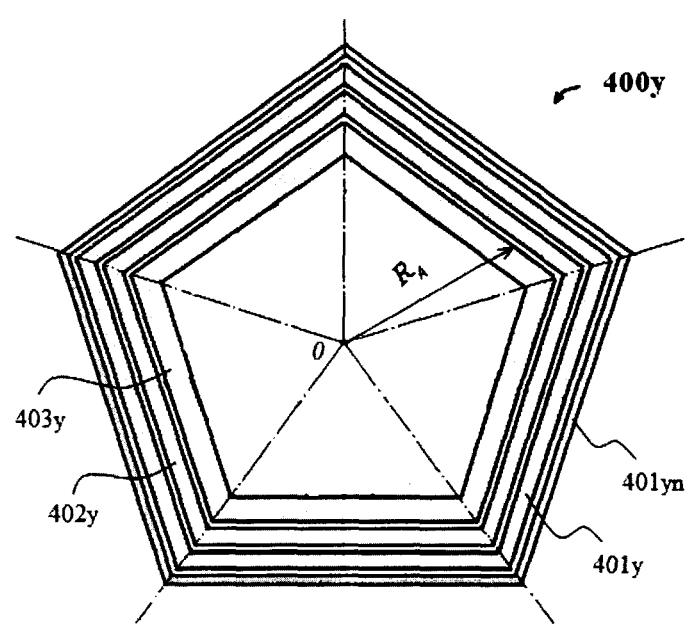
Figure 216:
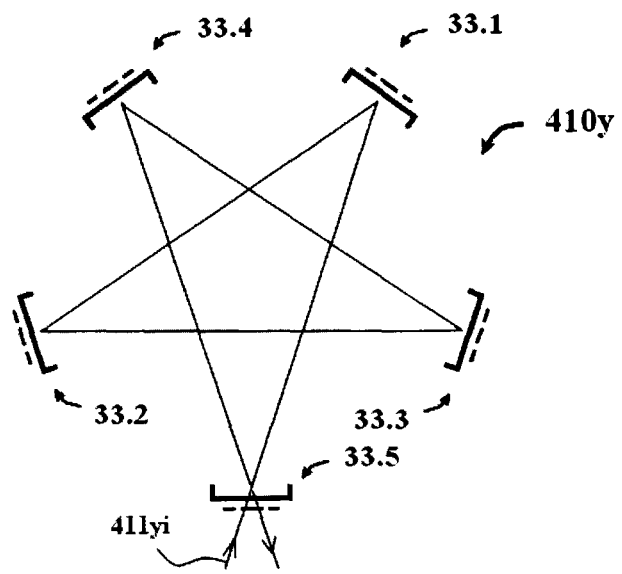

In FIG. 214 a single type of second-order curvilinear P-multireflector 390x is shown in a horizontal plane. The P-multireflector 390x includes four electrodes 391yn, 391y, 392y, and 393y, where adjacent facing frontal lines of electrodes are illustrated by circles, and $R_c$ denotes the distance from the geometrical center of the circles to the nearest inter-electrode gap spacing of the P-multireflector. FIG. 215 shows a single type of n-faced P-multireflector 400y including four electrodes 401yn, 401y, 402y and 403y and a distance $R_A$ from the geometrical center of the P-multireflector 400y to the nearest inter-electrode gap spacing of the P-multireflector. FIG. 216 shows a disjunctive n faced P-multireflector 410y including five local P-elements of reflection 33.1, 33.2, 33.3, 33.4, and 33.5, singly arranged as local P-elements of reflection in alternating an mode on each face, forming sectoral groups of reflecting P-elements, of a pentahedral polygon and a typical ion motion trajectory 411yi.

Figure 217:
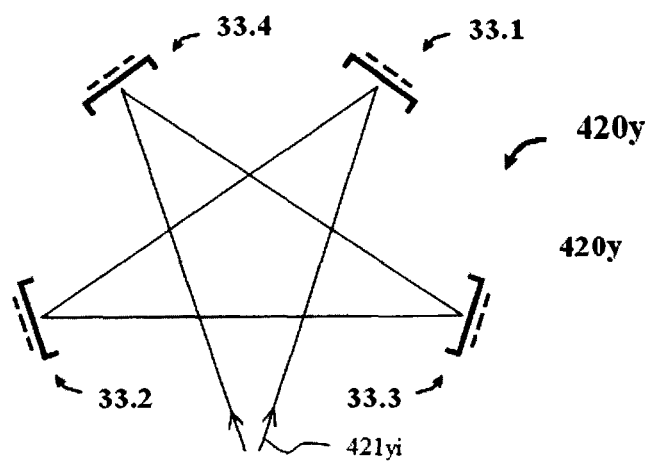

Each P-multireflectors 390x, 390y, 400y, and 410 has one or more lateral holes to input and output ions fluxes. FIG. 217 shows a j/n-sectoral/disjunctively faced n faced P-multireflector 420y, with j/n=4/5 and with four local P-elements of reflection 33.1, 33.2, 33.3, and 33.4, arranged in alternating modes on the four faces of a regular (equal faces) pentahedral polygon and a typical ion motion trajectory 421yi. FIGS. 218 to 232 show, in schematic view, extended P-multireflectors, designed to disperse TOF ions packets.

Figure 218:
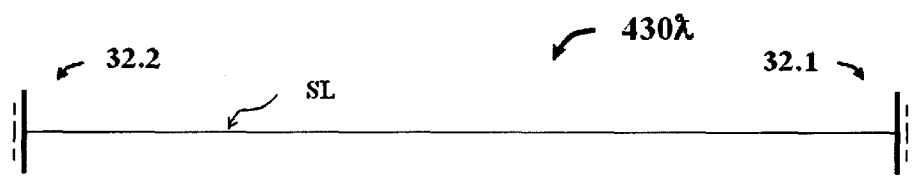
Figure 219:
Figure 220:
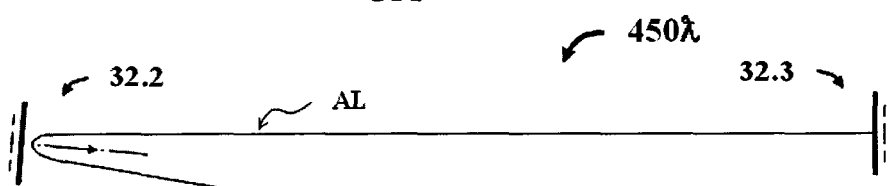
Figure 221:
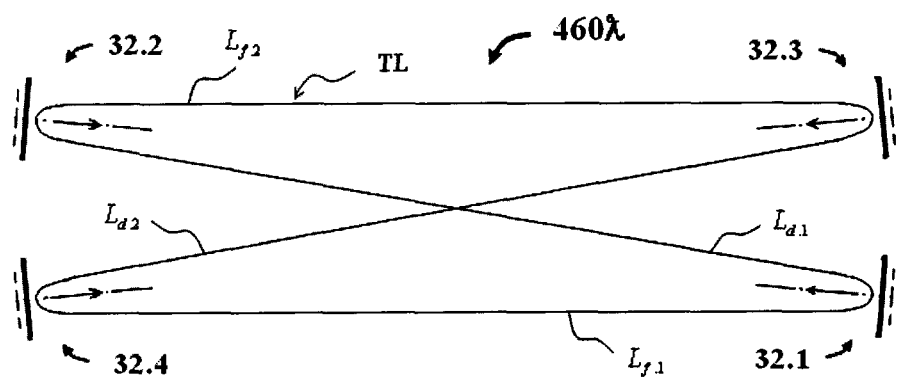
Figure 222:
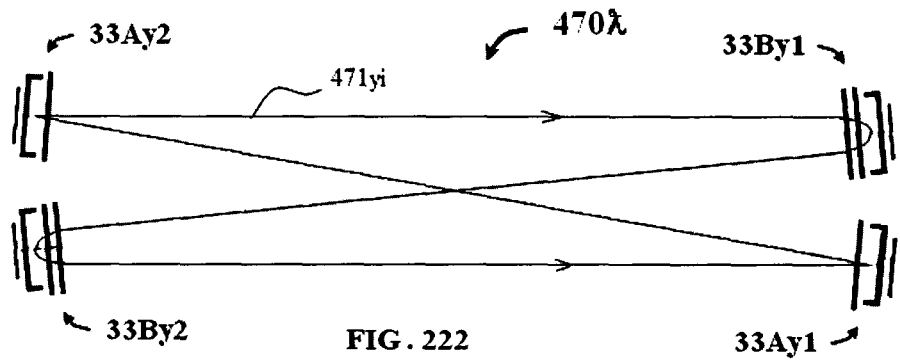
Figure 223:
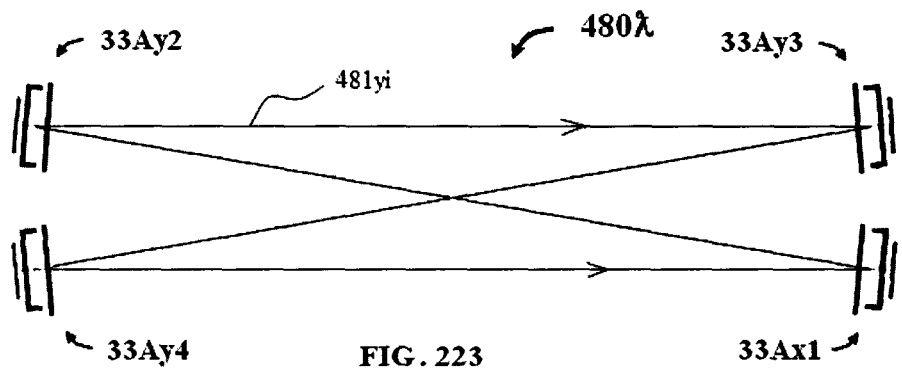
Figure 224:
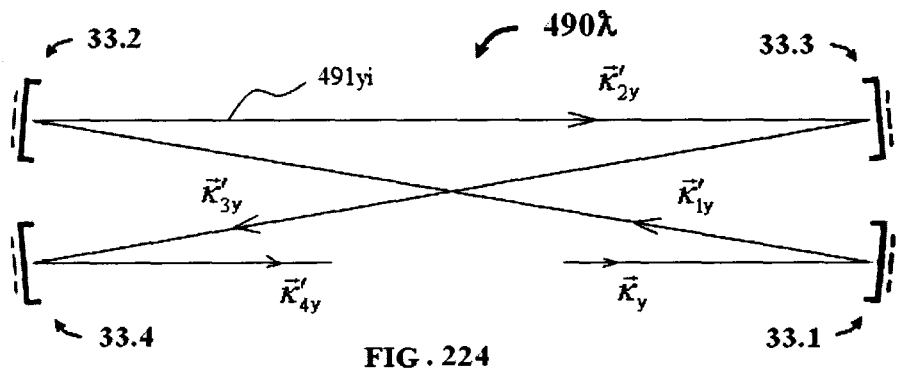

In FIGS. 218 to 221, in projections on a base plane D, are schematically shown the main types of extended P-multireflectors and their relevant typical lines each of which corresponds to a typical averaged ion motion trajectory in a specified P-multireflector. FIG. 218 shows a rectilinearly reflecting P-multireflector 430D with IO elements of reflection 32.1 and 32.2, arranged opposite one another such that their axial vectors are antiparallel in one plane (in the mean plane of the P-multireflector). A typical line SL of P-multireflector 430D is shaped in an orthogonal section. FIG. 219 shows a loop-shaped reflecting P-multireflector 440D with IO elements of reflection 32.1 and 32.2, arranged opposite one another such that their axial vectors are antiparallel in one plane (in mean plane of P-multireflector). A typical line CL of P-multireflector 440D is loop shaped. FIG. 220 shows an arc-wise reflecting P-multireflector 450D with IO elements of reflection 32.1, 32.2, and 32.3 and an arc-wise typical line AL of P-multireflector 450D. FIG. 221 shows a double-loop reflecting P-multireflector 460D, comprising: IO elements of reflection 32.1, 32.2, 32.3, and 32.4 and a typical line TL of P-multireflector 460D, having a two-loop shape. Constituent parts of typical line TL include a head-on frontal part $L_{f.1}$, arranged between the modules of reflection 32.1 and 32.4, a back-head frontal part $L_{f.2}$, arranged between modules of reflection 32.2 and 32.3, a first diagonal part $L_{d.1}$ arranged between modules of reflection 32.1 and 32.2, and a second diagonal part $L_{d.2}$, arranged between modules of reflection 32.3 and 32.4. FIGS. 222 to 232 show some examples related to specific IO elements of reflection and their spatial arrangement in double-loop-reflecting P-multireflector 460D shown in FIG. 221. Additionally, FIGS. 222 to 224 show versions of flat P-multireflectors, in projections on the base planes D of P-multireflectors, which coincide with coordinate planes yz, wherein IO elements of reflection of the P-multireflectors are of a local type (local type of IO element of reflection—mirror).

Figure 225:
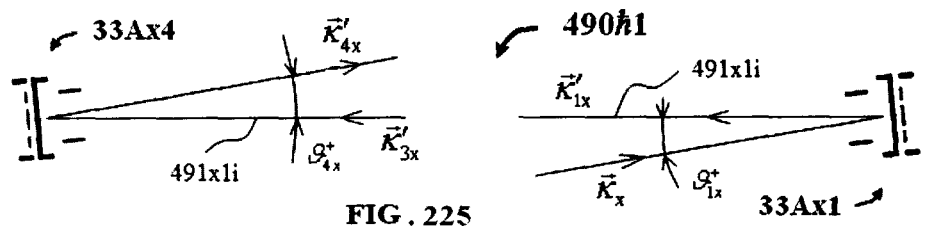
Figure 226:
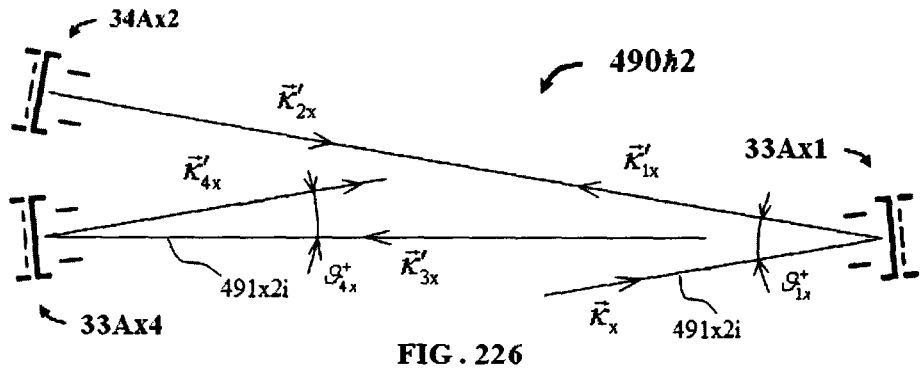

FIG. 222 shows a closed-loop P-multireflector 470D with local P-elements of reflection 33Ay1, 33Ay2, 33By1, and 33By2 and a typical ion motion trajectory 471yi therein. Local P-elements of reflection 33By1 and 33By2 are configured as vertical two-zone modules, and the trajectory of ion motion between them passes on another plane relative to other ion motion trajectories. FIG. 223 shows a closed-loop P-multireflector 480D with single-zone local P-elements of reflection 33Ay1, 33Ay2, 33Ay3, and 33Ay4, and a typical ion motion trajectory 481yi therein. Local P-elements of reflection 33Ay1, 33Ay2, 33Ay3, and 33Ay4 are arranged in one plane which is the base plane of P-multireflector 480D, their mean planes coincide, and ion motion trajectories between them pass on a single plane. FIG. 224 shows a non-closed-loop P-multireflector 490D comprising:

local single-zone P-elements of reflection 33.1, 33.2, 33.3, and 33.4, a dip vector and input $\vec{\kappa}_y$, a vector of first reflection $\vec{\kappa}'_{1y}$, a vector of second reflection $\vec{\kappa}'_{2y}$, a vector of third reflection $\vec{\kappa}'_{3y}$, and a vector of fourth reflection and output $\vec{\kappa}'_{4y}$ all of which are averaged vectors of ion flux motion trajectory directions 491yi; and a typical ion motion trajectory 491yi in the P-multireflector 490D. P-multireflector 490D is configured with an optional feature for arranging the averaged vector of path ion flux direction in different planes before the vector entering the field and after it leaves the field of the control subsystem, as with hetero-planar input-output). The output and input mean planes of first and fourth P-elements 33.1 and 33.4 intercross at an angle $\bar{\omega}$ (not shown in the Figures). The spatial arrangements and orientations of the local P-elements of reflection may be implemented in different manners. FIG. 225 shows projections on coordinate plane xz of a rectangular Cartesian system of coordinates, which plane coincides with a longitudinal-incremental plane h, of: a P-multireflector 490h1 (one possible projection of P-multireflector 490D on the longitudinal-incremental plane h); a dip vector and input $\vec{\kappa}_x$, a vector of first reflection $\vec{\kappa}'_{1x}$, a vector of third reflection, and a vector of fourth reflection and output $\vec{\kappa}'_{4x}$, all of which are averaged vectors of directions of ion flux motion trajectory 491x1i; an angle of ion flux input-reflection $\vartheta^+_{1x}$ from the first P-element of reflection 33Ax1; and an angle of ion flux input-reflection $\vartheta^+_{4x}$ from fourth P-element of reflection 33Ax4. All local P-elements of reflection, including 33Ax1 and 33Ax4, are arranged in one plane, which is a base plane of P-multireflector 480h1. FIG. 226 shows projections on coordinate plane xz of a rectangular Cartesian system of coordinates, which plane coincides with the longitudinal-incremental plane h, of: a control subsystem 490h2 (one possible projections of P-multireflector 490D on the longitudinal-incremental plane h); a dip vector and input $\vec{\kappa}_x$, a vector of first reflection $\vec{\kappa}'_{1x}$, a vector of second reflection $\vec{\kappa}'_{2x}$, a vector of third reflection $\vec{\kappa}'_{3x}$, and a vector of fourth reflection and output $\vec{\kappa}'_{4x}$; an angle of input-reflection $\vartheta^+_{1x}$ from the first P-element of reflection 33Ax1; and an angle of ion flux input-reflection $\vartheta^+_{4x}$ from the fourth P-element of reflection 33Ax4. All local P-elements of reflection, with the exception of local P-element of reflection 33Ax2, are arranged in one plane, which is the base plane of P-multireflector 480h2. Local P-element of reflection 33.2 is arranged off the base plane of P-multireflector 480h2, such that its output and input mean planes are arranged at an angle (not shown in the Figures), relative to the base plane of P-multireflector 480h2.

Figure 227:
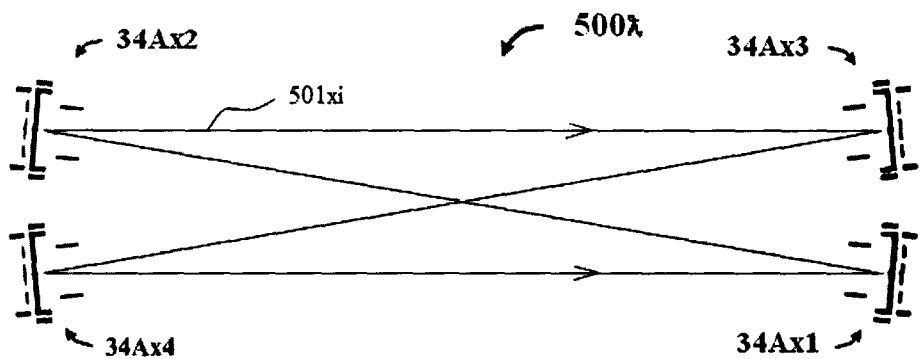
Figure 228:
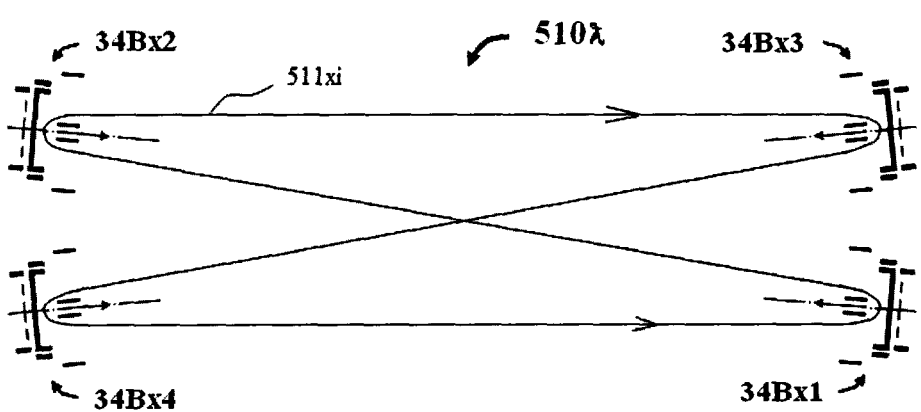
Figure 229:
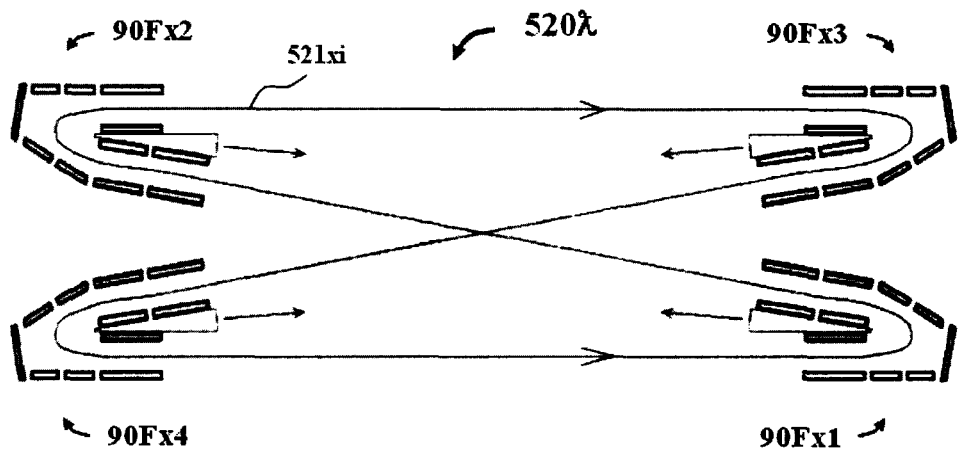

In FIGS. 227 to 229 there are shown some examples of implementation of double-loop-reflecting incremental P-multireflectors. FIG. 227 shows an incremental P-multireflector 500D with extended single-zone P-elements of reflection 34Ax1, 34Ax2, 34Ax3, and 34Ax4, and with a typical ion motion trajectory 501xi therein. FIG. 228 shows an incremental P-multireflector 510 D with extended two-zone P-elements of reflection 34Bx1, 34Bx2, 34Bx3, and 34Bx4, and with a typical ion motion trajectory 511xi therein. FIG. 229 shows an incremental P-multireflector 520D with extended two-zone P-elements of reflection 90Fx1, 90Fx2, 90Fx3, and 90Fx4 (which are examples of selection and arrangement of extended P-elements of reflection), and with a typical ion motion trajectory 521xi therein.

Figure 230:
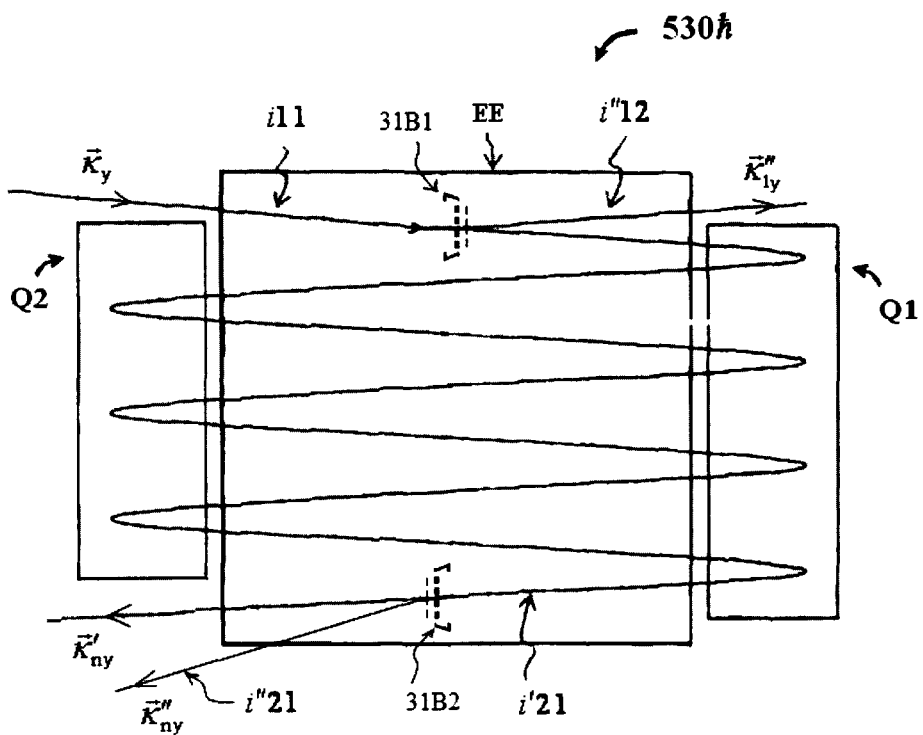

FIG. 230 schematically represents projections on the longitudinal-incremental plane h of: a general view of an incremental P-multireflector 530h with extended adjacent P-elements of reflection Q1 and Q2; a dip vector and input $\vec{k}_y'$, a vector of refraction $\vec{k}_{1y}'$ on an upper (first) IO element of refraction 31B1, a vector of refraction on a lower (second) IO element of refraction 31B2 and output $\vec{k}_{ny}'$, and a vector of reflection in the incremental P-multireflector 530h and output $\vec{k}_{ny}'$, all of which are averaged vectors of ion flux motion directions; a descending (straight) branch of trajectory i11, a refracted branch of trajectory i"12 on the upper (first) IO element of refraction 31B1, a left backward branch of trajectory i'21, and a left backward branch i"21 of trajectory, refracted on the lower (second) IO element of refraction 31B2; and a common mean electrode EE of P-multireflector 530h. Upper (first) IO element of refraction 31B1 and lower (second) IO element of refraction 31B2 are configured with optional features allowing their use in a multifunctional mode, or at least in two modes selected from the group comprising refraction, reflection and field-free modes.

Descending (straight) branch of trajectory i11 may originate from the ion source or from any other IO object. Left backward branch of trajectory i'21 or left backward branch i"21 of ion flux motion trajectory, refracted on lower (second) IO element of refraction 31B2, may be directed to the detector or to the input of any other IO object.

Figure 231:
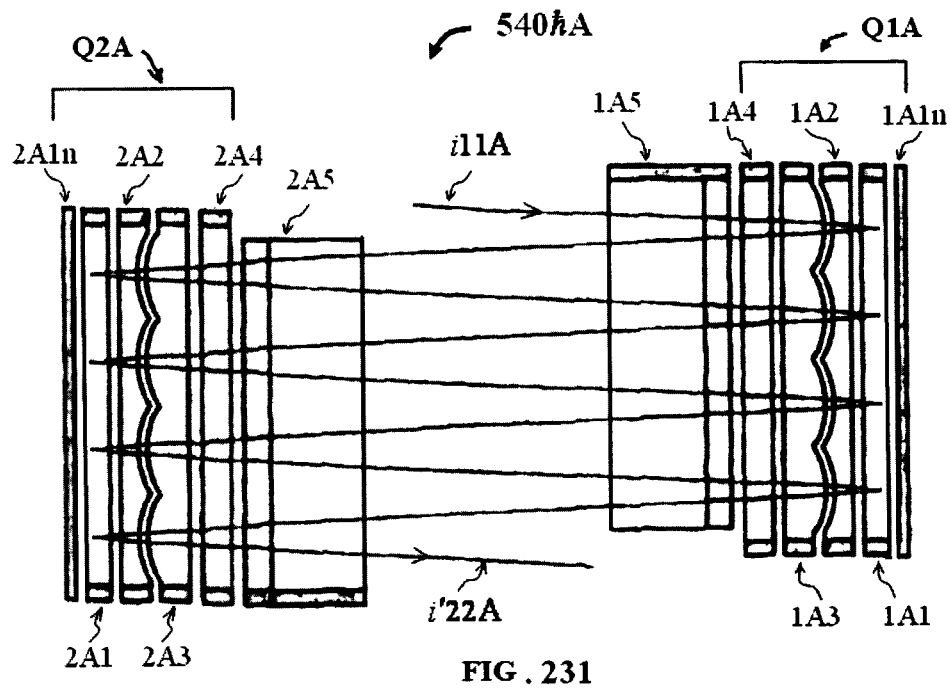
Figure 232:
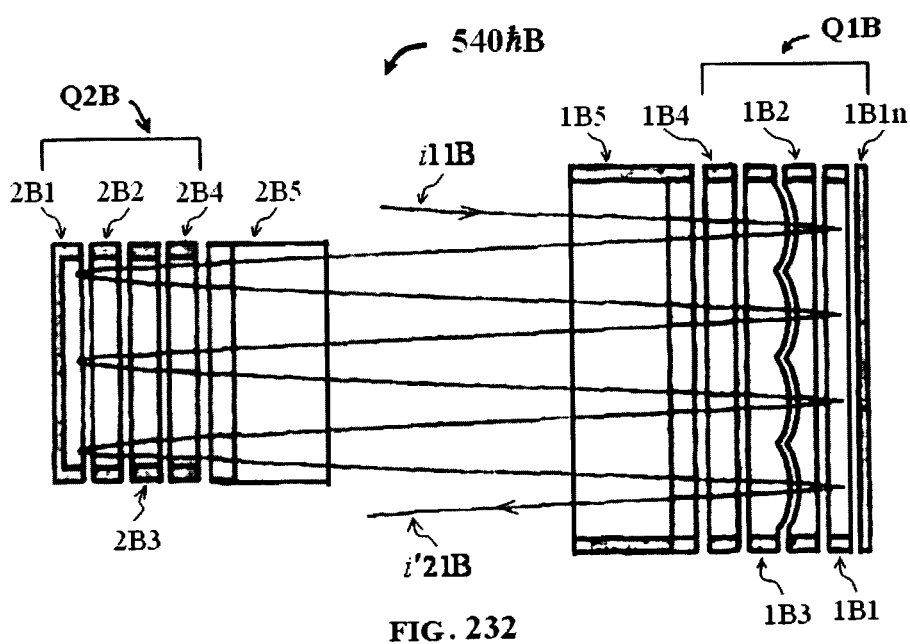

FIGS. 231 and 232 schematically represent projections on the longitudinal-incremental plane h of some types of extended configurations of P-multireflectors, in profile, on a plane of adjacent extended P-elements of reflection.

FIG. 231 represents: an incremental P-multireflector 540hA; a descending (straight) branch of trajectory i11A; a right backward branch of trajectory i'22A of extended P-elements of reflection Q1A and Q2A; electrodes 1A1n, 1A1, 1A2, 1A3, 1A4, and 1A5 of extended P-element of reflection Q1A; and electrodes 2A1n, 2A1, 2A2, 2A3, 2A4, and 2A5 of extended P-element of reflection Q2A. Electrode gap spacing between electrodes 1A2 and 1A3, as well as electrode gap spacing between electrodes 2A2 and 2A3 are configured as alternating segments of a second-order curve. Inter-electrode gap spacing between other electrodes are arranged rectilinearly. Electrodes 1A4 and 2A5 are integral parts of the common mean electrode.

FIG. 232 represents: an incremental P-multireflector 540hB having a typical ion motion trajectory 511xi therein; a descending (straight) branch of trajectory i11B; a right backward branch of trajectory i'22B of extended P-elements of reflection Q1B and Q2B; electrodes 1B1n, 1B1, 1B2, 1B3, 1B4, and 1B5 of extended P-element of reflection Q1B; electrodes 2A1n, 2B1, 2B2, 2B3, 2B4, and 2B5 of extended P-element of reflection Q2B and a typical ion motion trajectory 501xi therein. Electrode gap spacing between electrodes 1B2 and 1B3 are configured as alternating segments of a second-order curve. Inter-electrode gap spacing between other electrodes are arranged rectilinearly. Electrodes 1B4 and 2B5 are integral parts of the common mean electrode.

Figure 233:
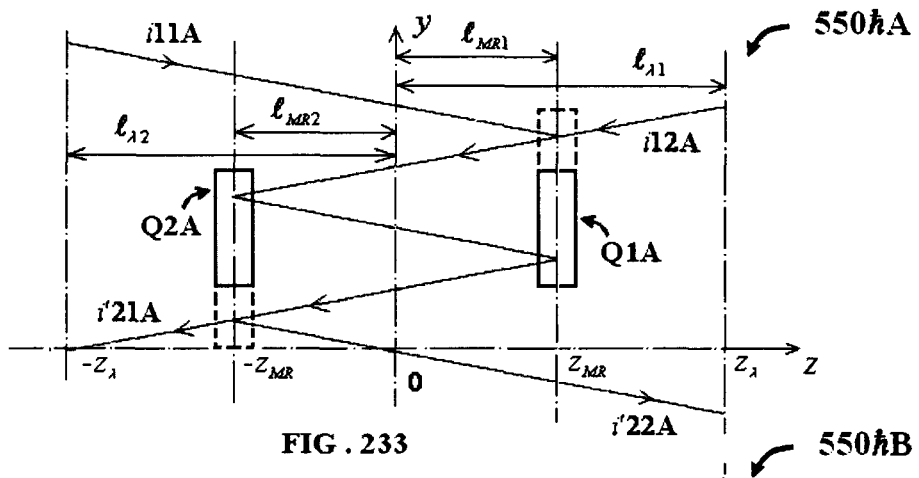
Figure 234:
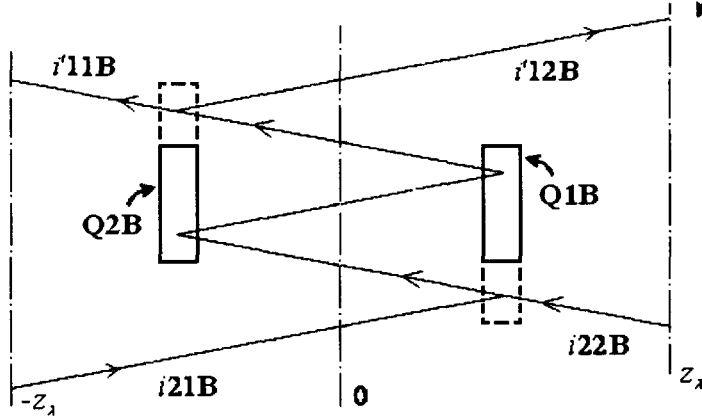
Figure 235:
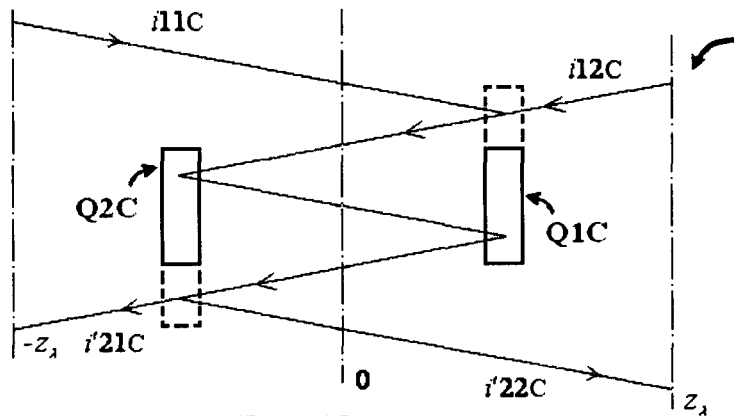

FIGS. 233 to 238 schematically represent projections on longitudinal-incremental plane h of some types of extended configurations of P-multireflectors, in profile, on a plane of adjacent extended P-elements of reflection. FIGS. 233 to 235 show P-multireflectors including optional features for input and output of ion flux from two different end sides, as in a double-sided through mode $R_W$. FIG. 233 shows: an incremental P-multireflector 550hA; a right upper descending (straight) branch i12A of trajectory; a left upper descending (straight) branch i11A of trajectory; a right lower backward branch i'22A of trajectory; a left lower backward branch i'21A of trajectory; a right extended P-element of reflection Q1A; a left extended P-element of reflection Q2A; a right operation zone of P-multireflector/(layer of $\{P_{\mu(s)}\}$-group) which is a zone of right trajectory between coordinates $\{-z_{MR}, z_\lambda\}$; a left operation zone of P-multireflector/(layer of $\{P_{\mu(s)}\}$-group) which is a zone of left trajectory between coordinates $\{-z_\lambda, z_{MR}\}$; a distance $l_{MR1}$ from the laterally incremental plane to the edge electrode slot on the side of ion reflections of right extended P-element of reflection Q1A; a distance $l_{\lambda 1}=2l_{MR1}$ from the laterally incremental plane to the plane $(z_\lambda)$; a distance $l_{MR2}$ from the laterally incremental plane to the edge electrode slot on the side of ion reflections of the left extended P-element of reflection Q2A; and a distance $l_{\lambda 2}=2l_{MR2}$ from the laterally incremental plane to the plane $(-z_\lambda)$. Preferably $l_{MR1}=l_{MR2}$ and $l_{\lambda 1}=l_{\lambda 2}$. FIG. 234 shows: an incremental P-multireflector 550hB; a right upper descending (straight) branch i12B of trajectory; a left upper descending (straight) branch i11B of trajectory; a right lower backward branch i22B of trajectory; a left lower backward branch i21B of trajectory; a right extended P-element of reflection Q1B; and a left extended P-element of reflection Q2B. Incremental P-multireflector 550hC shown in FIG. 235 is perfectly identical to the incremental P-multireflector 550hA.

Figure 236:
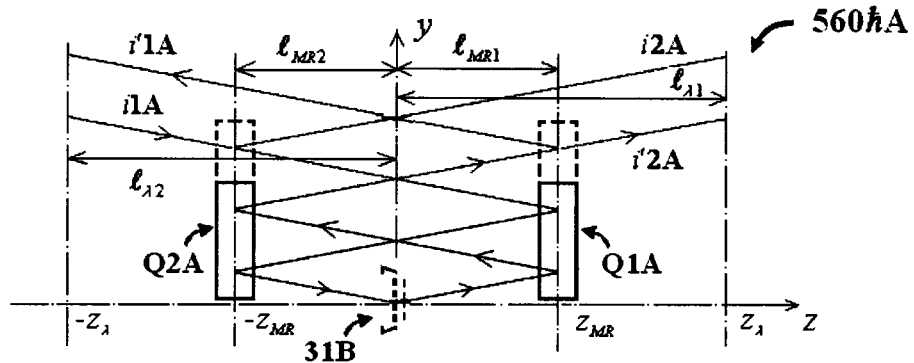
Figure 237:
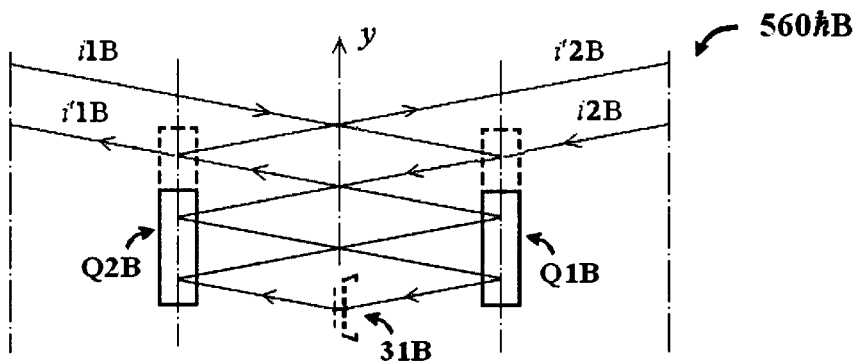
Figure 238:
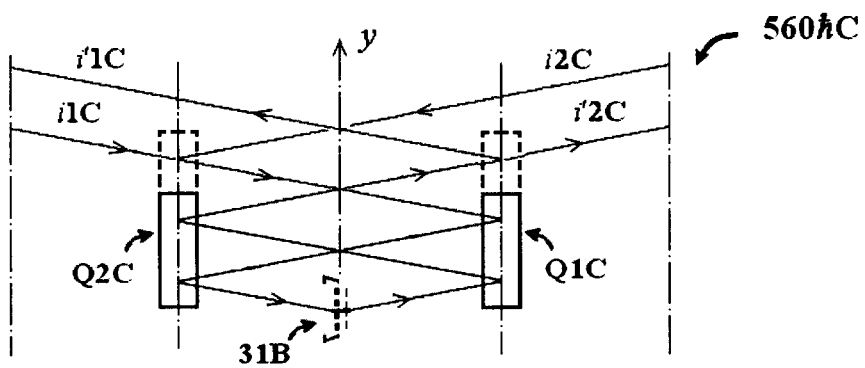

Direct adjacent ion flux transitions between the P-multireflectors/(layers of $\{P_{\mu(s)}\}$-group) 550hA, 550hB, and 550hC are preferred in their serial arrangement:

1) between P-multireflectors/(layers $\{P_{\mu(s)}\}$-group) 550hA and 550hB: from i'21A to i22B, from i'21A to i21B, from i'22A to i21B, and from i'22A to i22B; and 2) between P-multireflectors/(layers $\{P_{\mu(s)}\}$-group) 550hB and 550hC: from i'11B to i12C, from i'11B to i11C, from i'12B to i11C, and from i'12B to i12C. FIGS. 236 to 238 show P-multireflectors configured with an optional feature for input and output of the ion flux from one of its ends, i.e., in single recurring $R_{iV}^{(m)}$-mode. FIG. 236 shows: an incremental P-multireflector 560hA; a right descending (straight) branch of trajectory i2A; a left descending (straight) branch of trajectory i1A; a right backward branch of trajectory i'2A; a left backward branch of trajectory i'1A; a right extended P-element of reflection Q1A; a left extended P-element of reflection Q2A; a right operation zone of P-multireflector/(layer of $\{P_{\mu(s)}\}$-group), or, stated differently, a zone of right trajectory between the coordinates $\{-z_{MR}, z_\lambda\}$; a left operation zone P-multireflector/(layer of $\{P_{\mu(s)}\}$-group), or, stated differently, a zone of left trajectory between coordinates $\{-z_\lambda, z_{MR}\}$; a distance $l_{MR1}$ from a laterally incremental plane to an edge electrode slot on the side of ion reflection by right extended P-element of reflection Q1A; a distance $l_{\lambda 1}=2l_{MR1}$ from the laterally incremental plane to plane $(z_\lambda)$; a distance $l_{MR2}$ from the laterally incremental plane to an edge electrode slot on the side of ion reflection by left extended P-element of reflection Q2A; and a distance $l_{\lambda 2}=2l_{MR2}$ from the laterally incremental plane to plane $(-z_\lambda)$. Distances $l_{MR1}=l_{MR2}$ and $l_{\lambda 1}=l_{\lambda 2}$ are preferred. FIG. 237 shows: an incremental P-multireflector 560hB; a right descending (straight) branch i2B of trajectory; a left descending (straight) branch i1B of trajectory; a right backward branch i'2B of trajectory; a left backward branch i'1B of trajectory; a right extended P-element of reflection Q1B; and a left extended P-element of reflection Q2B. FIG. 238 shows an incremental P-multireflector 560hC perfectly identical to incremental P-multireflector 560hA.

Direct adjacent ion flux transitions between the P-multireflectors/(layers $\{P_{\mu(s)}\}$-group) 560hA, 560hB, and 560hC, are preferred in their serial arrangement:
1) between P-multireflectors/(layers $\{P_{\mu(s)}\}$-group) 560hA and 560hB: from i'1A to i1B, from i'1A to i2B, from i'2A to i2B, and from i'2A to i1B;
2) between P-multireflectors/(layers $\{P_{\mu(s)}\}$-group) 560hB and 560hC: from i'1B to i1C, from i'1B to i2C, from i'2B to i2C, and from i'2B to i1C.

In FIGS. 239 to 252, projections on the base planes D of P-multireflectors of some preferred types of ion flux transitions between two adjacent extended P-multireflectors are schematically shown. FIGS. 239 to 243 show ion flux transitions in projective-parallel, symmetrically-heteroplanar directions of channel ion flux. subsystems of transfer configured as control subsystems with projective-parallel, symmetrically hetero-planar inputs-outputs are mainly used to transfer the channel ion flux. This structure makes it possible to transfer the channel ion flux via frontal segments of typical lines of two double-loop reflecting P-multireflectors or via typical lines of two rectilinearly reflecting P-multireflectors. FIG. 239 shows: a typical line $SL_{11}$ having a first ultimate boundary $P_{11}$ and a second ultimate boundary $P_{12}$; a typical line $SL_{21}$ having a first ultimate boundary $P_{21}$ and a second ultimate boundary $P_{22}$; a first boundary $P_{u1}$ of ion flux transfer; a second boundary $P_{12}$ of ion flux transfer; an angle of input-reflection $\vartheta^+_{1A1}$ relative to typical line $SL_{11}$; an angle of input-reflection $\vartheta^+_{2A1}$ relative to typical line $SL_{21}$; and a length $\Lambda_Q$ of typical line $SL_{11}$ and $SL_{21}$. First boundary $P_{u1}$ of ion flux transfer and second boundary $P_{12}$ of ion flux transfer are located outside of typical line $SL_{11}$ and typical line $SL_{21}$, respectively. FIG. 240 shows: a typical line $SL_{11}$; a typical line $SL_{21}$; an angle of input-reflection $\vartheta^+_{2n1}$ relative to typical line $SL_{11}$; and an angle of input-reflection $\vartheta^+_{2R1}$ relative to typical line $SL_{21}$. First and second boundaries of ion flux transfer coincide with a first ultimate boundary $P_{11}$ of typical line $SL_{11}$ and with a second ultimate boundary $P_{22}$ of typical line $SL_{21}$, respectively. FIG. 241 shows: a typical line $SL_{11}$; a typical line $SL_{21}$; an angle of input-reflection $\vartheta^+_{1C1}$ relative to typical line $SL_{11}$; an angle of input-reflection $\vartheta^+_{2C1}$ relative to typical line $SL_{21}$; a first boundary $P_{m1}$ of ion flux transfer; and a second boundary $P_{m2}$ of ion flux transfer. FIG. 242 shows: a typical line $SL_{11}$; a typical line $SL_{21}$; an angle of refraction $\vartheta''_{D1}$ relative to typical line $SL_{11}$; an angle of refraction $\vartheta''_{2D1}$ relative to typical line $SL_{21}$; a first boundary $P_{x1}$ of ion flux transfer; and a second boundary $P_{x2}$ of ion flux transfer. FIG. 243 shows: a first typical line $TL_{11}$ and its frontal segment $L_{f11}$; a second typical line $TL_{21}$ and its frontal segment $L_{f21}$; an angle of input-reflection $\vartheta^+_{1E1}$ relative to frontal segment $L_{f11}$; an angle of input-reflection $\vartheta^+_{2E1}$ relative to frontal segment $L_{f21}$; a first boundary $P_{11}$ of ion flux transfer; and a second boundary $P_{x2}$ of ion flux transfer.

Figures 250, 251, 252:
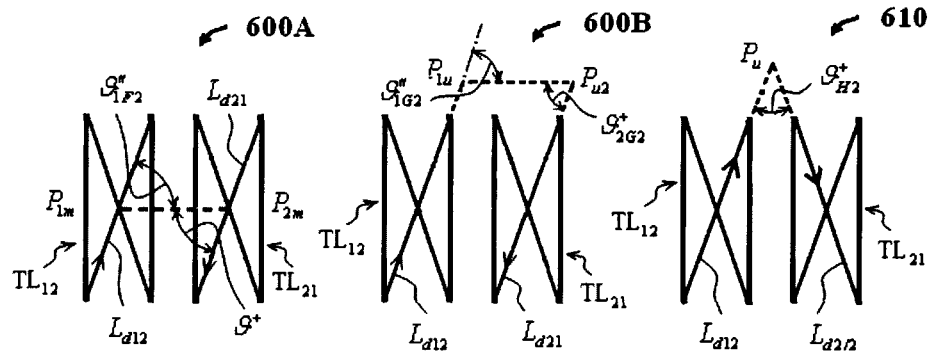
Figures 253, 254:
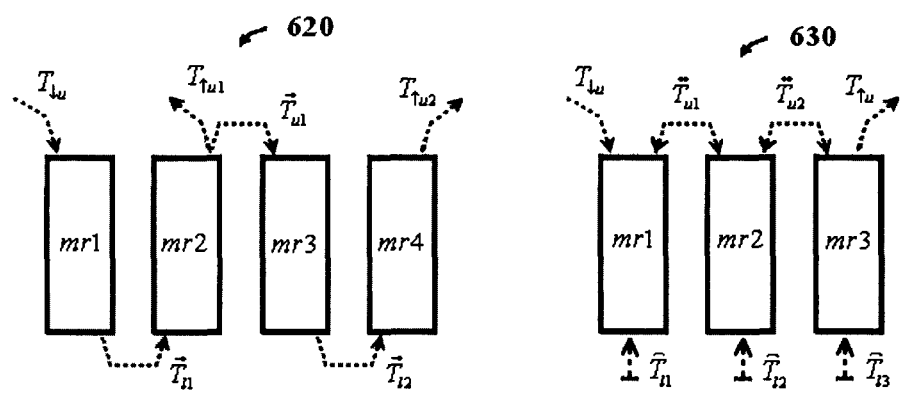
Figures 255, 256:
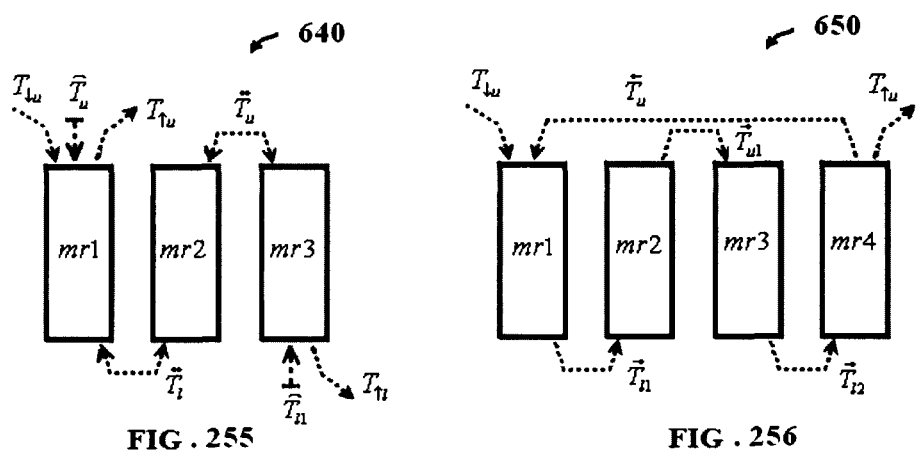
Figure 257:
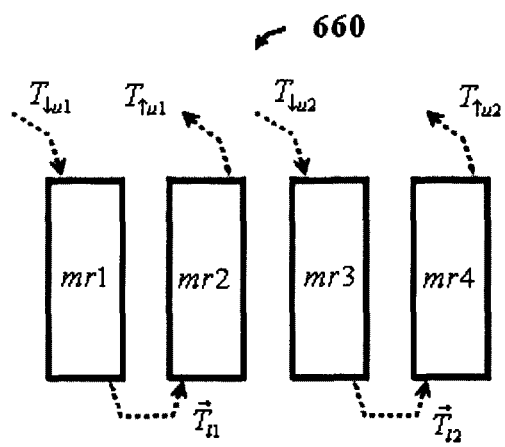
Figure 258:
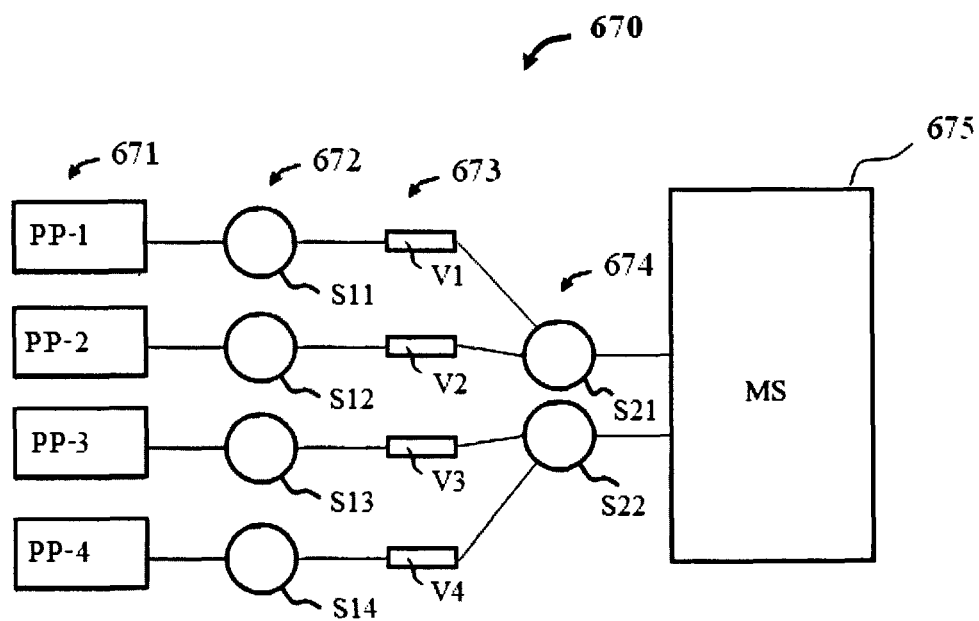
FIG. 258 represents an example of MS parallel-multiple-fluxes operation.

The examples shown in FIGS. 240 to 243 demonstrate that the assertions outlined above are true for all extended P-multireflectors. Increasing angles of input-reflection turn into angles of refraction, allowing IO elements of refraction to be used in transfer subsystems instead IO elements of reflection. FIGS. 244 to 248 show ion flux transfers in symmetrically single-plane projective-parallel directions of channel ion flux. Subsystems of transfer with single-plane projective-antiparallel input-output are mainly used to transfer the channel ion flux. This makes it possible to transfer the channel ion flux via frontal segments of typical lines of two double-loop reflecting P-multireflectors or via typical lines of two rectilinearly reflecting P-multireflectors. FIG. 244 shows: a typical line $SL_{11}$; a typical line $SL_{22}$; an angle of input-reflection $\vartheta^+_{1A2}$ relative to typical line $SL_{11}$; and an angle of refraction $\vartheta''_{2A2}$ relative to typical line $SL_{22}$. A first boundary $P_{u1}$ of ion flux transfer and a second boundary $P_{12}$ of ion flux transfer are located outside of typical line $SL_{11}$ and typical line $SL_{22}$, respectively. FIG. 245 shows: a typical line $SL_{11}$; a typical line $SL_{22}$; an angle of input-reflection $\vartheta^+_{1B2}$ relative to typical line $SL_{11}$; an angle of input-reflection $\vartheta^+_{2B2}$ relative to typical line $SL_{22}$; a first boundary $P_{m1}$ of ion flux transfer; and a second boundary $P_{m2}$ of ion flux transfer. FIG. 246 shows: a typical line $SL_{11}$; a typical line $SL_{22}$; an angle of refraction $\vartheta''_{1C2}$ relative to typical line $SL_{11}$; an angle of input-reflection $\vartheta^+_{2C2}$ relative to typical line $SL_{22}$; a first boundary $P_{m1}$ of ion flux transfer; a second boundary $P_{m2}$ of ions flux transfer; a first boundary $P_{x1}$ of ion flux transfer; and a second boundary $P_{u2}$ of ions flux transfer. Second boundary $P_{u2}$ of ion flux transfer is located outside of typical line $SL_{22}$. FIG. 247 shows: a typical line $SL_{11}$; a typical line $SL_{22}$; an angle of input-reflection $\vartheta^+_{1D2}$ relative to typical line $SL_{11}$; an angle of input-reflection $\vartheta^+_{2D2}$ relative to typical line $SL_{22}$; a first boundary $P_{u1}$ of ions flux transfer; and a second boundary $P_{u2}$ of ions flux transfer. FIG. 248 shows: a first typical line $TL_{11}$ and its frontal segment $L_{f11}$; a second typical line $TL_{22}$ and its frontal segment $L_{f22}$; an angle of input-reflection $\vartheta^+_{1E2}$ relative to frontal segment $L_{f11}$; an angle of input-reflection $\vartheta''_{2E2}$ relative to frontal segment $L_{f22}$; a first boundary $P_{11}$ of ion flux transfer; a second boundary $P_{x2}$ of ion flux transfer. FIGS. 249 to 252 show ion flux transfers by nonadjacent frontal characteristic lines into double-loop-reflecting P-multireflectors. FIG. 249 shows: a first typical line $TL_{12}$ and its diagonal segment $L_{d12}$; a second typical line $TL_{22}$ and its diagonal segment $TL_{d22}$; an angle of input-reflection $\vartheta^+_{1E2}$ relative to diagonal segment $L_{d12}$; an angle of input-reflection $\vartheta''_{2E2}$ relative to diagonal segment $L_{d22}$; a first boundary of ion flux transfer; and a second boundary $P_{x2}$ of ion flux transfer. FIG. 250 shows: a first typical line $TL_{12}$ and its diagonal segment $L_{d12}$; a second typical line $TL_{21}$ and its diagonal segment $L_{d21}$; an angle of refraction $\vartheta''_{2F1}$ relative to diagonal segment $L_{d21}$; an angle of input-reflection $\vartheta^+_{2F2}$ relative to diagonal segment $L_{d12}$; a first boundary $P_{1m}$ of ion flux transfer; and a second boundary $P_{2m}$ of ion flux transfer. FIG. 251 shows: a first typical line $TL_{12}$ and its diagonal segment $L_{d12}$; a second typical line $TL_{21}$ and its diagonal segment $L_{d21}$; an angle of refraction $\vartheta''_{1G2}$ relative to diagonal segment $L_{d12}$; an angle of input-reflection $\vartheta^+_{2G2}$ relative to diagonal segment $L_{d21}$; a first boundary $P_{u1}$ of ion flux transfer; and a second boundary $P_{u2}$ of ion flux transfer. FIG. 252 shows: a first typical line $TL_{12}$ and its diagonal segment $L_{d12}$; a second typical line $TL_{21}$ and its diagonal segment $L_{d2/2}$; and an angle of input-reflection $\vartheta^+_{H2}$ relative to diagonal segment $L_{d12}$ and relative to diagonal segment $L_{d2/2}$. FIGS. 253 to 257 schematically show projections of some preferred embodiments of ion flux transfer between several extended P-multireflectors, the projections being on a longitudinal-incremental plane h of a P-multireflector. FIG. 253 shows: a P-multireflector mr1, a P-multireflector mr2, a P-multireflector mr3, and a P-multireflector mr4; a symbol of transfer $T_{\downarrow u1}$ of incident ion flux into P-multireflector mr1; a symbol of first adjacent direct lower transfer $\overset{\shortrightarrow}{T}_{l1}$ of ion flux from P-multireflector mr1 into P-multireflector mr2; a symbol of first upper output $T_{\uparrow u1}$ of ion flux from P-multireflector mr2; a symbol of first adjacent direct upper transfer $\overset{\shortrightarrow}{T}_{u1}$ of ion flux from P-multireflector mr2 into P-multireflector mr3; a symbol of second adjacent direct lower transfer $\overset{\shortrightarrow}{T}_{l2}$ of ion flux from P-multireflector mr3 into P-multireflector mr4; and a symbol of second upper output $T_{\uparrow u2}$ of ion flux from P-multireflector mr4. FIG. 254 shows: a P-multireflector mr1, a P-multireflector mr2, and a P-multireflector mr3; a symbol of transfer $T_{\downarrow u1}$ into P-multireflector mr1 of incident ion flux; a symbol of first lower double transfer $\overset{\leftrightarrow}{T}_{l1}$; a symbol of first adjacent two-way upper transfer $\overset{\leftrightarrow}{T}_{u1}$ of ion flux between P-multireflector mr1 and P-multireflector mr2; a symbol of second lower counter-flow transfer $\overset{\leftrightarrow}{T}_{l2}$; a symbol of second upper adjacent two-way transfer $\overset{\leftrightarrow}{T}_{u2}$ of ion flux between P-multireflector mr2 and P-multireflector mr3; a symbol of third lower counter-flow transfer $\overset{\leftrightarrow}{T}_{l3}$; and a symbol of upper output $T_{\uparrow u}$ of ion flux from P-multireflector mr3. FIG. 255 shows: a P-multireflector mr1, a P-multireflector mr2, and a P-multireflector mr3; a symbol of transfer $T_{\downarrow u1}$ into P-multireflector mr1 of incident ion flux; a symbol of adjacent two-way lower transfer $\overset{\leftrightarrow}{T}_{l}$ of ion flux between P-multireflector mr1 and P-multireflector mr2; a symbol of adjacent two-way upper transfer $\overset{\leftrightarrow}{T}_{u}$ of ion flux from P-multireflector mr2 into P-multireflector mr3; a symbol of upper double transfer $\overset{\leftrightarrow}{T}_{u}$; a symbol of lower counter-flow transfer $\overset{\leftrightarrow}{T}_{l}$; a symbol of upper output $T_{\uparrow u}$ of ion flux from P-multireflector mr1; and a symbol of lower output $T_{\downarrow l}$ of ion flux from P-multireflector mr3. FIG. 256 shows: a P-multireflector mr1, a P-multireflector mr2, a P-multireflector mr3, and a P-multireflector mr4; a symbol of transfer $T_{\downarrow u1}$ into P-multireflector mr1 of incident ion flux; a symbol of first adjacent lower direct transfer $\overset{\shortrightarrow}{T}_{l1}$ of ion flux from P-multireflector mr1 into P-multireflector mr2; a symbol of first upper direct transfer $\overset{\shortrightarrow}{T}_{u1}$ ion flux from P-multireflector mr2 into P-multireflector mr3; a symbol of second adjacent lower direct transfer $\overset{\shortrightarrow}{T}_{l2}$ of ion flux from P-multireflector mr3 into P-multireflector mr4; a symbol of far reverse upper transfer $\overset{\leftarrow}{T}_{u}$ of ion flux from P-multireflector mr4 into P-multireflector mr1; and a symbol of upper output $T_{\uparrow u}$ of ion flux from P-multireflector mr4. The system of P-multireflectors shown in FIG. 256 is configured to have an optional feature for use in a running-multicyclic mode. FIG. 257 shows: a P-multireflector mr1, a P-multireflector mr2, a P-multireflector mr3, and a P-multireflector mr4; a symbol of transfer $T_{\downarrow u1}$ into P-multireflector mr1 of incident ion flux; a symbol of first adjacent lower direct transfer $\overset{\shortrightarrow}{T}_{l1}$ of ion flux from P-multireflector mr1 into P-multireflector mr2; a symbol of first upper output $T_{\uparrow u1}$ of ion flux from P-multireflector mr2; a symbol of transfer $T_{\downarrow u2}$ into P-multireflector mr3 of incident ion flux; a symbol of second adjacent lower direct transfer $\overset{\shortrightarrow}{T}_{l2}$ of ion flux from P-multireflector mr3 into P-multireflector mr4; and a symbol of second upper output $T_{\uparrow u2}$ of ion flux from P-multireflector mr4. The system of P-multireflectors shown in FIG. 257 is configured to have an optional feature for use in a two channel mode. FIG. 258 shows: a first chromatographic line comprising a pump PP-1, a switch S11, and a chromatographic column V1; a second chromatographic line comprising a pump PP-2, a switch S12, and a chromatographic column V2; a third chromatographic line comprising a pump PP-3, a switch S13, and a chromatographic column V3; a fourth chromatographic line comprising a pump PP-4, a switch S14, and a chromatographic column V4; a switch S21 integrating the output of the first and second chromatographic lines into one of MS channels or MS paths; and a switch S22 integrating the output of the third and fourth chromatographic lines into one of MS channels or MS paths. The system shown in FIG. 258 describes one potential application of multichannel and/or multipath mass-spectrometry.

The method of mass spectroscopy and device for its implementation as described herein allow for developing a MS with enhanced resolution power as compared to known prototypes:

a) Processes of parallel spectrometry in a MS channel with two or more multipath ion fluxes, as well as processes of spectrometry of one off-axis path ion flux, facilitate a reduction of time-of-flight and transverse space aberrations;

b) Processes of ion flux multi-reflection by means of channel IO multi-reflector subsystems described herein allow for an increase in space capacity of an ion flux by preventing the crossing over of an ion flux path, and preventing the lighter ions from going ahead of heavier ions by one or more laps or cycles, resulting in increased time-of-flight ion dispersion by mass;

c) Processes of ion flux refraction and/or reflection by means of control subsystems described herein allow for efficient management of the ion flux structure and for origination of diverse MS devices having minimized resource intensity and smaller geometrical dimensions, resulting in substantially reduced equipment mass and costs while providing enhanced resolution power as compared to known spectrometer prototypes.

Example of Mass-Spectrometer (MS) Operation

To date, a nonmagnetic mass-spectrometer with IB-channel of rotational symmetry relative to a straight axis (hereinafter referred to as TOF MS-F1) has been developed; it is shown in FIGS. 133 and 134, and described with respect to the mentioned figures.

The TOF MS-F1 functions as follows: from an annular entrance gate 68 W2, thin ion packages are entered into a local IO refraction module comprising electrodes 65, 66, and 67 together with an input electrode 68 and with an electrode diaphragm 64, having a surface exposed to the electrodes. Transverse velocity of ions coming from exit window 68 is relatively low because it is mainly due to their thermal movement at temperature 3000 K. At that energy, the scattering does not exceeds De=0.1 eV. In certain cases, e.g., at secondary ions emission where total energy scattering (corresponding to a sum of transverse V| and longitudinal V|| velocity components) reaches De=100 eV, the transverse component of velocity vector reaches up to 0.1 of velocity vector value, i.e., it corresponds to De=10 eV. Ions coming from the source "windows" are substantially (defined as: to a large extent, as known in the art) accelerated by electric fields and acquire some energy (and thus the velocity) which in ion mirror area reaches at least E=1 кeV. This energy is mainly attributed to the longitudinal velocity component. Ions packages acquire extra transverse velocity components and transverse dispersion by energy in moving outside of the main mass-spectrometer axis. At that acquired extra transverse velocity components are directed towards to the main mass-spectrometer axis.

At some point, the main axis is crossed over by ions having equal energy, so that ions having energy of a certain range pass into the opening 64Θ of input diaphragm 64. From input diaphragm 64 ions enter into a local IO reflection module comprising electrodes 61, 62, and 63 together with reflecting electrode-limiter 61n and with electrode diaphragm 64, which has a surface exposed to the electrodes. Ion packages, reflected in a non-uniform axisymmetric (axially symmetrical) electrostatic field, enter into an annular output window 64W1 which is also the window of an annular detector. Dispersion by ions mass and energy occurs along the whole path of ions, and, initially, a single thin ion package disintegrates. In a reflection area, high-energy ions moving in a longitudinal direction penetrate more deeply into the electrostatic reflecting field as compared to the low-energy ions, allowing ions to be focused by energy on the surface of output window 64W1, or, stated differently, on the surface of the ion detector. Thus, at the surface of output window 64W1, ions enter in the form of thin packages, each of which contains ions of uniform mass.

The size guide for the mass-spectrometer TOF MS-F1 is as follows: the inside diameter of ring-shaped electrodes is 40 mm and the distance from the plane of the ion source to the end mirror electrode is 380 mm.

Pilot testing proved that the TOF MS-F1 has the relative sensitivity threshold=$10^{-5}$; resolution power at a level of 50% spectral peak is 650 and the mentioned values are not extreme for such MS. These TOF MS-F1 performance characteristics are record setting in efficiency and substantially differ from prototype values of known nonmagnetic time-of-flight mass-spectrometers of such small size.

The enhanced TOF MS-F1 sensitivity level and resolution power are achieved through distinguishing features of its mass-spectrometry process and through a device differing the process from known prototype processes and devices for their implementation:

1) To reflect ions, as in other mass-spectrometry processes, a non-uniform axisymmetric electrostatic field, which is a particular case of a doubly symmetrical field, is used. The spatial distribution of the field is decided-on consistently for all TOF MS-F1 components aimed at optimizing management, focusing ion packages and maximizing sensitivity and mass-spectrometry resolution power;

2) Ions packages are delivered from the annular entrance gate 68W2, and electrode 64 comprises a diaphragm 64Θ at its center and an annular output window 64W1;

3) Incident and reflected ion fluxes are separated by geometry; a double angular space ion focusing process is performed on the surfaces of annular output window 64W1.

The contribution of annular entrance gate 68 W2 to enhancing the resolution power of TOF MS-F1 may be approximately evaluated based on the fact that, under otherwise equal conditions, the sensitivity level of TOF MS-F1 depends on the source area, such that the greater the source area, the higher the sensitivity level. Thus, the resolution power depends on the source width, such that the greater the source width, the lesser the resolution power. Under certain conditions for annular and circular windows, the source width and area are determined, respectively, by:

Ring width: $d_k = \lambda(r_{k2} - r_{k1})$;

circle diameter: $d_o = \lambda r_o$, where: $r_{k2}$ and $r_{k1}$ are, respectively, diameters of outer and inner circles of the annular window, and where $r_o$ is the radius of a circular window. All other parameters being equal, when only the widths of the entrance gates are different, e.g.: $r_{k2} = 2r_o$, $r_{k1} = r_o$, the area of an annular window is three times larger than the area of a circular window.

The most important features distinguishing the method disclosed herein from known prototypes include potential control of the strength of transverse spatial dispersion by energy, where the TOF MS-F1 may operate in different modes, the two main operation modes being as follows:

1. Obtain mass spectra using a large diaphragm opening diameter having low transverse dispersion by energy, such that practically all ions of the initial package are passed through the diaphragm opening. In this case, the TOF MS-F1 operates in a mode of obtaining mass spectra within a large range of the energy spectrum of the initial ion package.

2. Obtain mass spectra using a small diaphragm opening diameter having high transverse dispersion by energy. This operation mode, at adequate potential gradients in TOF MS-F1 constituent elements, allows for obtaining mass spectra in diverse constricted sections of the energy spectrum of the initial ion package.

The invention claimed is:

1. A method of mass-spectrometry, comprising:
ionizing a substance sample in an ionic source block, formation an ion flux in MS,
managing motion of said ion flux including mass dispersion by at least one of the ion flux by mass/charge ratio, by means of at least one of a magnetic field and an electric field; said magnetic field and said electric field generated by groups of ion-conducting blocks comprising ion-conducting IB-channels with boundary surfaces and IO channel systems, where IB-channels are part of a MS-channel with its own MS-channel IO system;
wherein said MS channel comprises at least one said ion-conducting IB-channel and at least one ionic source IB-channel of said ionic source block connected in series,
wherein said IO channel system of each said ion-conducting IB-channel comprises at least one of: a subsystem with a curved main axis in a cross-space dispersing mode, a subsystem with a curved main axis, in a multi-reflecting mode, and any other subsystem, hereinafter named as a management subsystem,
registering ions in said ion flux using at least one detector group of a detector system; and controlling and managing of all blocks of a mass-spectrometer as well as supporting data processing in said mass spectrometer using a controller-computer subsystem,
wherein said forming and said management of said ionic source block connected in series,
wherein said IO channel system of each said ion-conducting IB-channel comprises at least one of a control subsystem, a subsystem with a curved main axis in a cross-space dispersing mode, and a subsystem with a curved main axis in a multi-reflecting mode, and
wherein said generating and said controlling said motion are carried out by at least one of:
(a) parallel mass-spectrometry in a said MS-channel using at least one mode selected from: channel-multipath ion flux including a mode with multi-cell section surfaces, off-axis channel-single-path ion flux, including a mode with double-cell section surfaces;
(b) control of said ion flux using an electric IO channel system comprising at least one of an IO element enabling selection of a specified spatial orientation of said IO element relative to at least one other IO element and relative to a direction of an averaged vector of said ion flux entering said IO element, a flat unary P-multireflector, a three-dimensional P-multireflector, a cascade-multilayered multireflector, an extended P-element of refraction, a three-dimensional P-element of reflection, a P-element of non-uniform height, and a P-element of reflection with a two-dimensional reflection zone.

2. The method of claim 1 that enable single-channel and multichannel mass-spectrometry, wherein said ion flux comprises at least one single-path ion flux which passes through said MS-channel, wherein each said path ion flux is detected by an individual detector of said detector system.

3. The method of claim 2, wherein said path ion fluxes comprises at least two path ion fluxes, each received from a different source, and injected into at least one of said groups of ion conducting blocks through a different output gate of an ionic source system.

4. The method of claim 3, wherein said at least two path ion fluxes exiting from at least one said output gate of said ionic source system are supplied in at least one of: independently of one another, and in a time correlation function relative to one another.

5. The method of claim 2, wherein values of said mass dispersion and of energy dispersion of said ion flux are regulated by energy spectrometry performed concurrently with mass-spectrometry, and mass-spectrometry at specified range intervals of an energy spectrum of said ion flux.

6. The method of claim 1, wherein one cyclicity mode used in passage of said ion flux is selected from the group consisting of single-cycle ion passage, and multi-cycle ion passage through at least some said IB-channels.

7. The method of claim 5, wherein said mass-spectrometry is performed using a mode selected from the group consisting of: single-staged mode, MS/MS mode, and MS⟨n⟩-mode.

8. The method of claim 7, wherein cross-spatial space focusing of said ion flux is performed on a detector surface, at least along one of two cross-spatial space directions.

9. The method of claim 7, wherein cross-spatial space focusing of said ion flux is performed along a path of motion of said ion flux by means of pulsating voltage.

10. The method of claim 7, wherein said mass spectrometry comprises) time-of-flight mass-spectrometry, selected from the group consisting of MS⟨n⟩-type and MS/MS-type, and is performed by an nested time mode.

11. A nonmagnetic management subsystem for control of charged particle flux, selected from a group of functional versions consisting of:
  (a) a subsystem of refraction comprising at least one IO element of refraction;
  (b) a subsystem of reflection comprising n local IO elements of reflection, where: n is an integer number and n≤3 and including no more than two local P-elements of reflection and extended IO elements of reflection;
  (c) a mixed subsystem of reflection and refraction, comprising said subsystems (a) and (b); and
  (d) a multifunctional subsystem, comprising one of said subsystems (a), (b) and (c), wherein at least one IO element is multifunctional and enables selection of at least two operation modes selected from the group consisting of: refracting, reflecting and field-free, said nonmagnetic management subsystem including at least one IO element selected from the group consisting of: IO element enabling selection of a specified spatial orientation of said IO element relative to at least one other IO element and relative to a direction of an averaged vector of said ion flux entering said IO element, a flat unary P-multireflector, a three-dimensional P-multireflector, a cascade-multilayered multireflector, an extended P-element of refraction, a three-dimensional P-element of reflection, a P-element of non-uniform height, and a P-element of reflection with a two-dimensional reflection zone.

12. The management subsystem of claim 11, comprising a local IO element having at least one of functional and design characteristics, wherein said local IO element is selected from the group of functional characteristic IO elements consisting of: a local IO elements of refraction, a local IO lens, a local telescopic IO element, a local IO prism, a local cylindrical condenser, a local plane condenser, a local IO mirror, a single-zone local IO element of reflection, a vertical double-zone local IO element of reflection, a horizontal double-zone local IO element of reflection, a joint group of local IO elements of reflection wherein each pair of reflecting elements shares a common electrode, and a local multifunctional IO element, wherein said local IO element is selected from the group of design characteristic IO elements consisting of: a local two-dimensional IO element, a Cartesian two-dimensional IO element on a plane, a condenser of non-uniform height on a plane, a plane condenser, a Cartesian two-dimensional IO element on a surface, a condenser of non-uniform height on a surface, a cylindrical condenser, a local three-dimensional IO element, a local doubly symmetric IO element, a sectorial transbending IO element, a sectorial transaxial IO element, a V-shaped IO element, a conic IO element, a crossed IO element, a boxlike IO element, a transbending-mixed IO element, a crossed-mixed IO element, a boxlike-mixed IO element, and a heterogenic-mixed IO element.

13. The management subsystem of claim 11, comprising at least one extended IO element selected from the group consisting of single-staged and array-staged extended IO elements, having at least one of functional and design features, where said extended IO element is selected from the group of functional feature IO elements consisting of: an extended IO element of refraction, an extended IO lens, an extended telescopic IO element, an extended IO prisms, an extended IO element of reflection, a single-zone extended IO element of reflection, a vertical double-zone extended IO element of reflection, a horizontal double-zone extended IO element of reflection, a joint group of extended IO elements of reflection,
  wherein each pair of reflection elements shares a common electrode, and an extended multifunctional IO element,
  wherein said extended IO element is selected from the group of design characteristic IO elements consisting of: an extended two-dimensional IO element, a Cartesian two-dimensional IO element on a plane, a condenser of non-uniform height on a plane, a plane condenser, a Cartesian two-dimensional IO element on a surface, a condenser of non-uniform height on a surface, a cylindrical condenser, an extended three-dimensional IO element, an extended doubly symmetric IO element, an alternating sectorial transbending IO element, an alternating sectorial transaxial IO element, an alternating V-shaped IO element, an alternating conic IO element, an alternating crossed IO element, an alternating boxlike IO element, an alternating transaxial bending-mixed IO element, an alternating crossed-mixed IO element, an alternating boxlike-mixed IO element, and an alternating heterogenic-mixed IO element.

14. The management subsystem of claim 11, wherein said at least one IO element comprises a doubly symmetric IO element, and electrode operating surfaces of said IO element are arranged as at least one of planar operating surfaces, concave operating surfaces, and a pair of parallel identical planar operating surfaces such that adjacent facing frontal lines of at least one electrode pair are described by sections of second-order curves.

15. The management subsystem of claim 11, wherein said at least one IO element comprises an axisymmetric IO element, and electrode operating surfaces of said IO element are selected from the group consisting of: cylinder surfaces diaphragm-electrode surfaces; surfaces as sectors of cones; and revolving surfaces, generated by rotation of components thereof about a straight axis and described by segments of second-order curves, wherein at least one electrode of said IO element comprises at least one hole for ion flux passage.

16. The management subsystem of claim 15, wherein said electrode operating surfaces comprise diaphragm-electrode operating surfaces having one of planar and concave forms.

17. The management subsystem of claim 11, wherein said IO element comprises an IO element of reflection having an cover electrode, such that it is located perpendicular to an axis/plane of symmetry of an adjacent electrode of said IO element.

18. The management subsystem of claim 11, comprising a P-element configured to allow ions in said charged particle flux to move on portions of an M-surface proximate said P-element.

19. The management subsystem of claim 18, wherein said P-element comprises a first P-element comprising one of a P-element of reflection and a multifunctional P-element, and additionally comprises at least one IO element of refraction configured as a second P-element, such that output and input mean planes of said first and second P-elements are substantially parallel.

20. The management subsystem of claim 11, comprising a P-element configured to allow ions in said charged particle flux to move proximate a longitudinal-vertical plane of said P-element.

21. The management subsystem of claim 20, wherein said P-element comprises at least one P-element being one of a P-element of reflection and a multifunctional P-element, and additionally comprises at least one IO element of refraction configured as a P-element.

22. The management subsystem of claim 21, wherein longitudinal-vertical planes of said at least one P-element and said IO element of refraction are substantially parallel.

23. The management subsystem of claim 11, wherein said at least one IO element comprises a first IO element and a second IO element, defining:

an angle $\beta_{(12)1}$ between vectors read counterclockwise from a unitary vector $n_{(12)}$, directed from said first IO element towards said second IO element and arranged on a line interconnecting effective points of reflection/refraction on a path ion flux of said first and second IO elements, towards a unitary axial vector $n_1$ of said first IO element, wherein said angle $\beta_{(12)1}$ is within the range $$0 \beta_{(12)1} \frac{\pi}{2};$$

and an angle $\beta_{(12)2}$ between vectors read counterclockwise from said unitary vector $n_{(12)}$ towards a unitary axial vector $n_2$ of said second IO element, wherein said angle $\beta_{(12)2}$ is within the range $$\pi \beta_{(12)2} \frac{3\pi}{2}.$$

24. The management subsystem of claim 23, wherein said angle $\beta_{(12)1}$ is within the range $$0 \beta_{(12)1} \frac{\pi}{2},$$

and said angle $\beta_{(12)2}$ is within the range $$\frac{\pi}{2} \beta_{(12)1} \pi.$$

25. The management subsystem of claim 23, comprising first, second, and third identical IO elements, configured such that:

said angle $\beta_{(12)1}$ is within the range $$\frac{3\pi}{2} \beta_{(12)1} 2\pi;$$

said angle $\beta_{(12)2}$ is within the range $$\pi \beta_{(12)2} \frac{3\pi}{2};$$

an angle $\beta_{(23)2}$, defined between vectors read counterclockwise from a unitary vector $n_{(23)}$, directed from said second IO element towards said third IO element and arranged on a line interconnecting effective points of reflection/refraction on a path ion flux of said second and said third IO elements, towards said unitary axial vector $n_2$, is within the range $$\frac{3\pi}{2} \beta_{(23)2} 2\pi;$$

and an angle $\beta_{(23)3}$, defined between vectors, read counterclockwise from said unitary vector $n_{(23)}$ towards a unitary axial vector $n_3$ of said third IO element, is within the range $$\pi \beta_{(23)3} \frac{3\pi}{2}.$$

26. The management subsystem of claim 25, wherein said first, second, and third identical IO elements are configured such that said angle $\beta_{(12)1}$ is within the range $$0 \beta_{(12)1} \frac{\pi}{2}.$$

said angle $\beta_{(12)2}$ is within the range $$\pi \beta_{(12)2} \frac{3\pi}{2},$$

said angle $\beta_{(23)2}$ is within the range $$\frac{3\pi}{2} \beta_{(23)2} 2\pi,$$

and said angle $\beta_{(23)3}$ is within the range $$\frac{\pi}{2} \beta_{(23)3} \pi.$$

27. The management subsystem of claim 25, wherein said first, second, and third identical IO elements are configured such that said angle $\beta_{(12)1}$ is within the range $$\frac{3\pi}{2} \beta_{(12)1} 2\pi,$$

said angle $\beta_{(12)2}$ is within the range $$\pi \beta_{(12)2} \frac{3\pi}{2},$$

said angle $\beta_{(23)2}$ is within the range $$\frac{3\pi}{2} \beta_{(23)2} 2\pi,$$

and said angle $\beta_{(23)3}$ is within the range $$\frac{\pi}{2} \beta_{(23)3} \pi.$$

28. The management subsystem of claim 11, comprising a multi-element P-element arranged in a horizontal-straight-line and configured to allow arrangement of said averaged vector of said charged particle flux on an M-surface proximate said P-element.

29. The management subsystem of claim 28, wherein output and input mean planes of P-elements forming part of said management subsystem are parallel to each other.

30. The management subsystem of claim 28, comprising two P-elements having output and input mean planes intersecting at an angle $\overline{\omega}$, and configured to allow substantial coinciding of a line of intersection of said mean planes with said averaged vector of said path ion flux at a midway point between said P-elements, wherein said angle $\overline{\omega}$ is within the range $$0 \varpi \frac{\pi}{2}.$$

31. The management subsystem of claim 30, performed as a reflection subsystem wherein the projections $\theta'_{1y}$ and $\theta'_{2y}$, correspond to angles $\theta'_1$ and $\theta'_2$ on its base plane (superposed by coordinate plane yz) and projections $\theta'_{1x}$ and $\theta'_{2x}$, corresponding to angles $\theta'_1$ and $\theta'_2$, on their longitudinal-incremental plane (superposed by coordinate plane xz), on the assumption that $\theta'_1 = \theta'_2$ are determined respectively by formulas:

$$\vartheta'_{1y} = \vartheta'_{2y} = \operatorname{arctg}\left[(tg\vartheta)\sin\frac{\varpi}{2}\right]; \vartheta'_{1x} = \vartheta'_{2x} = \operatorname{arctg}\left[(tg\vartheta)\cos\frac{\varpi}{2}\right],$$

wherein: $\theta'_1$—angle of input-reflection of one P-element e, $\theta'_2$—angle of input-reflection of the other P-element.

32. The management subsystem of claim 28, additionally comprising at least one IO element of refraction configured as a series of single IO lens elements.

33. The management subsystem of claim 32, wherein said at least one IO element of refraction is a P-element of refraction, having at least one of input and output mean planes which are substantially parallel to at least one of input and output mean planes of symmetry of at least one of two adjacent P-elements of reflection.

34. The management subsystem of claim 12, comprising a multi-element P-element arranged in a vertical straight-line and configured to allow arrangement of said averaged vector of said charged particle flux on a longitudinal-vertical plane proximate said P-element.

35. The management subsystem of claim 34, comprising two P-elements having longitudinal-vertical planes which are substantially parallel to each other.

36. The management subsystem of claim 34, comprising two P-elements having longitudinal-vertical planes intersecting at an angle $\overline{\omega}_\perp$ and configured to allow coinciding of a line of intersection of said longitudinal-vertical-planes with said averaged vector of said path ion flux at a midway point between said P-elements, wherein said angle $\overline{\omega}_\perp$ is within the range $$0 \varpi_\perp \frac{\pi}{2}.$$

37. The management subsystem of claim 36, performed as a subsystem of reflection, where projections $\theta'_{\perp 1y}$ and $\theta'_{\perp 2y}$, correspond to angles $\theta'_{\perp 1}$ and $\theta'_{\perp 2}$ on its base plane (superposed by coordinate plane yz) and projections $\theta'_{\perp 1x}$ and $\theta'_{\perp 2x}$ correspond to angles $\theta'_{\perp 1}$ and $\theta'_{\perp 2}$ on their longitudinal-incremental plane (superposed by coordinate plane xz), on the assumption that $\theta'_{\perp 1} = \theta'_{\perp 2}$, are determined respectively by formulas:

$$\vartheta'_{\perp 1y} = \vartheta'_{\perp 2y} = \operatorname{arctg}\left[(tg\vartheta_\perp)\cos\frac{\varpi_\perp}{2}\right];$$

$$\vartheta'_{1x} = \vartheta'_{2x} = \operatorname{arctg}\left[(tg\vartheta_\perp)\sin\frac{\varpi_\perp}{2}\right],$$

$\theta'_{2x} = 2\pi - \theta'_{1x}$, where: $\theta'_1$—angle of entry-reflection of one P-element e, $\theta'_2$—angle of entry-reflection of other P-element.

38. The management subsystem of claim 34, additionally comprising at least one IO element of refraction.

39. The management subsystem of claim 38, wherein said at least one IO element of refraction is a P-element of refraction having at least one of input and output mean planes which are substantially parallel to at least one of input and output mean planes of symmetry of at least one of two adjacent P-elements of reflection.

40. The management subsystem of claim 11, comprising a multi-element P-element configured to allow arrangement of said averaged vector of said charged particle flux in different planes before entering a field of said management subsystem and after leaving said field of said management subsystem, wherein input and output are of a hetero-planar type.

41. The management subsystem of claim 40, comprising a projecting-parallel symmetrically hetero-planar input-output, said management subsystem being selected from the group consisting of horizontal-straight-line and vertical straight-line management subsystems.

42. The management subsystem of claim 11, comprising a multi-element P-element configured to allow arrangement of said averaged vector of said charged particle flux in one plane, equivalent to arrangement before entering a field of said management subsystem and after leaving said field of said management subsystem.

43. The management subsystem of claim 42, comprising antiparallel input-output and selected from the group consisting of horizontal-straight-line and vertical straight-line management subsystems, mentioned in this invention.

44. The management subsystem of claim 43, wherein said input-output converges at an scalene angle.

45. The management subsystem of claim 11, comprising at least one diaphragm-electrode including at least one hole, wherein a configuration of said at least one hole is selected from the group consisting of: round, oval, quadrupole, and quadrupole with rounded edges.

46. The management subsystem of claim 45, wherein said at least one hole of said diaphragm-electrode is configured to cross over at least one of mean plane and a symmetry axis of said management subsystem, and wherein at least one said diaphragm-electrode is configured to control a size and a configuration of said at least one hole, thereby causing changes in functional features of said management subsystem.

47. A P-multireflector for controlling an ion flux configured to allow at least four ion flux reflections in an electric field, comprising two modes of operation selected from the group consisting of an incremental mode of narrow shape and a unary mode shape, wherein, when said P-multireflector comprises a P-multireflector of narrow shape, said P-multireflector is selected from the group consisting of: straight-line-reflecting, one-loop-reflecting, arc-wise-reflecting, and two-loop-reflecting, and Wherein, when said P-multireflector comprises a unary P-multireflector of wide shape, said P-multireflector is selected from the group consisting of second-order curvilinear and n-faced.

48. The P-multireflector of claim 47, comprising a local IO element having at least one of functional and design features, wherein said local IO element is selected from the group of functional characteristic IO elements consisting of: a local IO element of refraction, a local IO lens, a local telescopic IO element, a local IO prism, a local cylindrical condenser, a local plane condenser, a local IO mirror, a single-zoned IO element of reflection, a vertically double-zoned IO element of reflection, a horizontally double-zoned local IO element of reflection, a joint group of a local IO element of reflection wherein each pair of reflecting elements shares a common electrode, and a local multifunctional IO element, and wherein said local IO element is selected from the group of design characteristic IO elements consisting of: a local two-dimensional IO element, a Cartesian two-dimensional IO element on a plane, a condenser of non-uniform heights on a plane, a plane condenser, a Cartesian two-dimensional IO element on a surface, a condenser of non-uniform heights on a surface, a cylindrical condenser, a local three-dimensional IO element, a locally doubly symmetric IO element, a sectoral transbending IO element, a sectoral transaxial IO element, a V-shaped IO element, a conic IO element, a crossed IO element, a boxlike IO element, a transbending-mixed IO element; a crossed-mixed IO element; a boxlike-mixed IO element, and a heterogenic-mixed IO element.

49. The P-multireflector of claim 47, comprising at least one extended IO element selected from the group consisting of single-extended and array-extended IO elements, having at least one of functional and design features, wherein said extended IO element is selected from the group of functional feature IO elements consisting of: an extended IO element of refraction, an extended IO lens, an extended telescopic IO element, an extended IO prism, an extended IO element of reflection, a single-zoned extended IO element of reflection, a vertically double-zoned extended IO element of reflection, a horizontally double-zoned extended IO element of reflection, a joint group of extended IO elements of reflection wherein each pair of reflection element shares at least one common electrodes, and wherein said extended IO element is selected from the group of design characteristic IO elements consisting of: an extended two-dimensional IO element, a Cartesian two-dimensional IO element on a plane, a condenser of non-uniform height on a plane, a planar condenser, a Cartesian two-dimensional IO element on a surface, a condenser of non-uniform height on a surface, a cylindrical condensers, an extended three-dimensional IO element, an extended doubly symmetric IO element, an alternating sectoral transbending IO element, an alternating sectoral transaxial IO element, an alternating V-shaped IO element, an alternating conic IO element, an alternating crossed IO element, an alternating boxlike IO element, an alternating transaxial-bending-mixed IO element, an alternating crossed-mixed IO element, an alternating boxlike-mixed IO element, and an alternating heterogenic-mixed IO element.

50. The P-multireflector of claim 47, configured as a single type second-order curvilinear P-multireflector comprising one group of electrodes, wherein adjacent facing frontal lines of electrodes in said group are defined by segments of second-order curves and at least one electrode comprises at least one hole for passing of said ion flux.

51. The P-multireflector of claim 47, configured as a single sectoral type second-order curvilinear P-multireflector comprising one group of electrodes wherein adjacent facing frontal lines of electrodes in said group of electrodes are described by segments of second-order curves.

52. The P-multireflector of claim 47, configured as a second order curvilinear P-multireflector, wherein a type of second-order curvilinear structure is selected from the group consisting of: single-zoned, vertically double-zoned, and three-dimensional.

53. The P-multireflector of claim 47, configured as a second order curvilinear P-multireflector, wherein a distance between a geometric center of said P-multireflector and a nearest electrode gap is substantially greater than a mean distance between electrodes.

54. The P-multireflector of claim 47, configured as a single type n-faced P-multireflector comprising one group of electrodes, wherein adjacent facing frontal lines of electrodes in said group of electrodes are defined by continuous lines, each of which generates an n-isofaced polygon, wherein each electrode in said group of electrodes comprises-segments, and wherein said group of electrodes comprises at least one hole for input-output of said ion flux.

55. The P-multireflector of claim 47, configured as a j/n-single sectoral type n-faced P-multireflector, comprising j faced sectoral segments and n−1 faces.

56. The P-multireflector of claim 47, configured as a disjunctive n-faced P-multireflector, comprising a group of n local P-elements of reflection arranged in alternating modes on each face of an n-polyhedral polygon, where P-elements are mentioned in claim 48.

57. The P-multireflector of claim 47, configured as a j/n-sectoral/disjunctively-faced n-faced P-multireflector, comprising j-faced sectoral segments of a disjunctively-faced n-faced P-multireflector including n−1 faces, where P-multireflectors are mentioned in this invention.

58. The P-multireflector of claim 47, wherein types of n-faced categories have the number of faces decided-on referring to the equation $$n \approx \frac{2\pi R}{3d}$$

wherein: n—number of faces (n—odd integer and n≥5), d—mean distance between electrode armatures (gap width), R—distance from the geometric center of the P-multireflector to the first electrode gap.

59. The P-multireflector of claim 47, comprising a unary type element configured to allow representation of reflected paths of ion motion outside a field of said P-multireflector in projections on a base plane of said P-multireflector as reflected from a single effective surface of reflection having a section described by a second-order curve.

60. The P-multireflector of claim 47, comprising a unary type element which is selected from the group consisting of single-zoned and vertically double-zoned types.

61. The P-multireflector of claim 47, comprising at least two P-multireflectors, mentioned in this invention of at least one of local types and extended types, wherein each of said local types and said extended types of P-multireflector is configured to allow ions to move along a generic line in accordance with requirements to input and output fluxes, reflecting from each P-element of reflection, wherein the relation of the width (longitudinal size)—$L_Q$ of the P-multireflector to its thickness (transverse size)—$L_{MRh}$, in a projection to its base plane, is limited within the range $$1.5 \leq \frac{L_Q}{L_{MRh}} \leq 100,$$

wherein a drift space (field-free space) is generated between the P-elements of reflection.

62. The P-multireflector of claim 61, configured as a rectilinearly reflecting P-multireflector comprising two single-zoned P-elements of reflection facing each other, wherein antiparallel axial vectors of said P-elements are located in one plane, and wherein said P-multireflector is configured to allow said ions to move along a path whose projection onto a base plane of said P-multireflector comprises a substantially linear segment.

63. The P-multireflector of claim 61, configured as a loop-shaped reflecting P-multireflector configured to allow said ions to move along a path whose projection to a base plane of said P-multireflector is configured as a loop-shaped line, wherein said P-multireflector comprises at least one double-zoned P-element of reflection.

64. The P-multireflector of claim 61, configured as an arc-wise reflecting P-multireflector configured to allow said ions to move along a path whose projection on a base plane of said P-multireflector is configured as a V-shaped line, and wherein said P-multireflector comprises two end P-elements of reflection arranged at ends of said V-shaped line and a middle P-element of reflection arranged atop said V-shaped line, wherein said middle P-element of reflection comprises a double-zoned P-element of reflection and said end P-elements of reflection comprise single-zoned P-elements of reflection.

65. The P-multireflector of claim 64, wherein a distance from one of said end P-elements of reflection to said middle P-element of reflection is many times as large as a distance between said two end P-elements of reflection, and wherein a drift space is generated between said end P-elements of reflection and said middle P-element of reflection.

66. The P-multireflector of claim 61, configured as a two-loop-reflecting P-multireflector configured to allow said ions to move along a trajectory whose projection onto a base plane of said P-multireflector is defined by a curved line comprising two loops with one common vertex comprising a nodal point of triangular segments, such that one of four P-elements of reflection are arranged at each outer vertex of each said loop.

67. The P-multireflector of claim 66, wherein its two-loop-wise reflecting types have the width (longitudinal size) $L_Q$-thickness (transverse size) $L_{MRh}$ ratio of the P-multireflector plotted on the projections to its base plane confined within the range $$1.5 \leq \frac{L_Q}{L_{MRh}} \leq 100;$$

and a drift space (field-free space) is generated between the P-elements of reflection within the midway of its length.

68. The P-multireflector of claim 66, wherein said two-loop-reflecting P-multireflector is arranged symmetrically relative to an interloop plane of said generic line and to a geometric mean plane separating heterolooped P-elements of reflection into different sides of said interloop plane.

69. The P-multireflector of claim 64, arranged in incremental mode and comprising at least two extended P-elements of reflection, mentioned in this invention.

70. The P-multireflector of claim 69, wherein linear axes of said at least two extended P-elements of reflection are parallel to each other.

71. The P-multireflector of claim 69, wherein said at least two extended P-elements of reflection comprise two mutually conjugate P-elements, one of which is a Cartesian two-dimensional P-element and the other of which is a three-dimensional P-element.

72. The P-multireflector of claim 69, wherein said at least two extended P-elements of reflection comprise two mutually conjugate P-elements, both of which are three-dimensional P-elements.

73. The P-multireflector of claim 69, further comprising at least one IO element of refraction selected from the group consisting of local IO elements of refraction and extended IO elements of refraction, mentioned in this invention.

74. The P-multireflector of claim 73, wherein said at least one IO element of refraction comprises a local IO element of refraction.

75. The P-multireflector of claim 74, comprising at least two local IO elements of refraction which alternate relative to increments of reflection.

76. The P-multireflector of claim 73, comprising at least two identical local IO elements of refraction configured as sectoral-transbending IO elements.

77. The P-multireflector of claim 69, further comprising an extended IO element of refraction affecting said ion flux along a path of each increment of reflection of said P-multireflector, said extended IO element of refraction being located in a drift space and comprising an extended IO lens element, mentioned in this invention.

78. The P-multireflector of claim 69, arranged in a recurring one-path $R_{iV}^{(m)}$-mode, where i=1 at the first type and i=2 at the second type of the mode and additionally comprises a management subsystem, mentioned in this invention,
wherein the input and output are performed on one of the end side: upper end surface, at (m)=(U) and on the lower end side facing to the upper end side at (m)=(L).

79. The P-multireflector of claim 69, configured to allow ion flux input and output from two different end sides in two-paths using $R_{H}$-mode.

80. The P-multireflector of claim 61, wherein a unary mode of narrow configuration comprises at least two local P-mirrors, mentioned in this invention.

81. The P-multireflector of claim 80, arranged in a non-closed two-loop-reflecting mode with an entry-exit of projection-parallel symmetrically non-coplanar type.

82. The P-multireflector of claim 80, wherein all of said at least two local P-mirrors are arranged proximate a base plane of said P-multireflector.

83. The P-multireflector of claim 80, wherein a second of said at least two P-mirrors is arranged in one diagonal segment of a looping line with an entry P-mirror located outside of a base plane of said P-multireflector, and where exit and entry mean planes of said second of said at least two P-mirrors are arranged at acute plane angles within the range larger than zero and less than $$\frac{\pi}{4}$$

relative to said base plane, such that said acute plane angles are equal to each other.

84. The P-multireflector of claim 83, comprising at least four P-mirrors, wherein: exit and entry mean planes of a second and a third of said at least four P-mirrors coincide;
exit and entry mean planes of a first and said second of said at least four P-mirrors intersect at the angle $\bar{\omega}_{12}$, such that an intersection line of said exit and entry mean planes coincides with an averaged vector of a path ion flux at a midway point between said first and said second P-mirrors;
mean planes of a field symmetry of said third and a fourth of said at least four P-mirrors intersect at the angle $\bar{\omega}_{34}$, such that an intersection line of said mean planes coincides with said averaged vector of said path ion flux at a midway point between said third and said fourth P-mirrors such that $\bar{\omega}_{12}=\bar{\omega}_{34}$.

85. The P-multireflector of claim 80, wherein all of said at least two P-mirrors are arranged on a base plane of said P-multireflector, wherein input and output mean planes of said at least two P-mirrors are parallel to each other, and wherein in order to input said ion flux into said P-multireflector and to output said ion flux therefrom, said P-multireflector is configured to allow supply of electric potential in two modes into at least one of said P-mirrors and to provide an additional multifunctional IO element.

86. The P-multireflector of claim 80, wherein at least two of said P-mirrors are mutually conjugate, are arranged in one diagonal segment of said generic line, are configured as double-zoned P-mirrors, and are configured to allow arrangement of incoming and reflected ion motion paths on different parallel planes.

87. The P-multireflector of claim 80, arranged horizontally continuously and configured to allow arrangement of said averaged vector of said ion flux path along an M-surface of said P-elements.

88. The P-multireflector of claim 80, arranged vertically continuously and configured to allow arrangement of said averaged vector of said ion flux path along a longitudinal-vertical plane of said P-elements.

89. The P-multireflector of claim 80, configured to minimize intercrossing of different branches of said ion flux path.

90. The P-multireflector of claim 61, further comprising an IO element of refraction located in a drift space and selected from a group consisting of P-elements of refraction having rotational symmetry, mentioned in this invention.

91. An IB-channel of ions of a conducting type, comprising one of an IB-channel of an ion conducting block and an ion conducting IB-channel for forming and controlling motion of a channel ion flux comprising at least two boundary surfaces selected from the group consisting of:
(i) at least two boundary surfaces selected from the group consisting of a surface set, a conditionally specified surface, and a surface coinciding with a boundary electrode of an IO channel system, and provided with at least one gate port for passing said channel ion flux consisting of said selected boundary surfaces;
(ii) an IO channel system, wherein said ion conducting IB-channel comprises at least one control subsystem arranged with a curved main axis in at least one of cross-space dispersing mode and multi-reflecting mode, wherein said IB-channel is configured to be used in at least one of a channel-multipath ion flux including modes with multi-cell section surfaces and an off-axis single-path channel ion flux, including modes with doubly connected section surfaces;
and wherein said IB-channel includes at least one member selected from the group consisting of: an IO elements making it possible to select a specified spatial orientation of said IO element relative to other IO elements and relative to a direction of an averaged vector of ion flux entering said IO element; a flat single-syllable P-multireflector; a three-dimensional P-multireflector; a cascade-multilayered multireflector; an extended P-element of refraction; a three-dimensional P-element of reflection; a P-element of non-uniform height; and a P-element of reflection with a two-dimensional reflection zone.

92. The IB-channel of claim 91, wherein at least one of said at least two boundary surfaces has a rotational symmetry relative to a straight axis of said IB-channel.

93. The IB-channel of claim 92, configured to be used in a control mode including one of a single-path mode and a channel-multipath ion flux mode, wherein sections of path components on said at least one of said at least two boundary surfaces are selected from: spheroidal (elliptic) surfaces and ring surfaces, whose centers are arranged at a center of boundary surface rotational symmetry; surfaces of at least one segment of said rings; at least one of said rings; surfaces of rings arranged concentrically and in series relative to said center of boundary surface rotational symmetry; and surfaces comprising no less than two segments of different rings from the said groups of rings.

94. The IB-channel of claim 92, configured to allow an axis of rotational symmetry of said at least one of said at least two boundary surfaces to cross-over over a boundary section of said single-path channel ion flux $O_O$-crossing mode.

95. The IB-channel of claim 92, configured to allow arrangement of a boundary section of said single-path channel ion flux to be off-axis of an axis of rotational symmetry of said at least one of said at least two boundary surfaces in $O_E$-crossing mode.

96. The IB-channel of claim 92, configured to allow arrangement of boundary sections of path components of said multipath channel ion flux to be off-axis of an axis of rotational symmetry of said at least one of said at least two boundary surfaces in $O_{EE}$-crossing mode.

97. The IB-channel of claim 92, configured to allow an axis of rotational symmetry of said at least one of said at least two boundary surfaces to cross-over a boundary section of one path component of said multipath channel ion flux in $O_{OE}$-crossing mode.

98. The IB-channel of claim 91, comprising a conducting boundary surface with a mean plane, and configured to be used to control at least one of a single-path and said channel multipath ion flux, wherein sections of path components on said boundary surface are selected from the group consisting of: integral surfaces; surfaces of quadrupole tube sections whose centers are located at a geometric center of said boundary surface; surfaces of at least one segment of said surfaces of quadrupole tube sections; surfaces of quadrupole strips, arranged parallel to a mean plane of said boundary surface; surfaces of sections of quadrupole tube groups whose centers are located at said geometric center of said boundary surface; surfaces including at least two segments of surface sections of different quadrupole tubes in said quadrupole tube groups.

99. The IB-channel of claim 98, configured to allow said mean plane of said boundary surface to cross-over a boundary section of said single-path channel ion flux in $P_P$-crossing mode.

100. The IB-channel of claim 98, configured to allow arrangement of a boundary section of said single-path channel ion flux outside said mean plane of said boundary surface in $P_E$-crossing mode.

101. The IB-channel of claim 98, configured to allow said mean plane of said boundary surface to cross-over said boundary sections of path components of said multipath ion flux in $P_{PP}$-crossing mode.

102. The IB-channel of claim 98, configured to allow arrangement of said boundary sections of path components of said multipath channel ion flux outside said mean plane of said boundary surface in $P_{EE}$-crossing mode.

103. The IB-channel of claim 98, configured to allow said mean plane of said boundary surface to cross-over said boundary sections of path components of said multipath channel ion flux in $P_{PE}$-crossing mode.

104. The IB-channel of claim 91, comprising a doubly symmetrical boundary surface and including two mutually perpendicular planes of symmetry wherein an intersection line of said mutually perpendicular planes comprises a main axis of said boundary surface.

105. The IB-channel of claim 104, configured to be used to control at least one of a single-path channel ion flux and a multipath channel ion flux, wherein sections of path components on said boundary surface are selected from the group consisting of: integral surfaces and surfaces of quadrupole tube sections whose centers are located at a geometric center of said boundary surface; surfaces including at least one segment of the said surfaces of said quadrupole tube sections; surfaces of quadrupole strips arranged parallel to said mean plane of said boundary surface; surfaces of sections of a quadrupole tube group whose centers are located at said geometric center of said boundary surface; and surfaces including at least two segments of surface sections of different quadrupole tubes in said quadrupole tube group.

106. The IB-channel of claim 104, configured to allow said main axis of said boundary surface to cross over a boundary section of in $S_O$-crossing mode.

107. The IB-channel of claim 104, configured to allow at least one of: arrangement of a boundary section of said single-path channel ion flux outside said mean plane of said boundary surface in $S_E$-crossing mode; and said mean plane of said boundary surface to cross over said boundary section of said single-path channel ion flux in $S_P$-crossing mode.

108. The IB-channel of claim 104, configured to allow said channel ion flux to cross-over said boundary surface in at least one of $S_{PP}$-mode, $S_{EE}$-mode, and $S_{PE}$-mode.

109. The IB-channel of claim 104, configured to allowing said channel ion flux to cross-over said boundary surface in at least one of $S_{OP}$-mode, $S_{OE}$-mode, and $S_{OPE}$-mode.

110. The IB-channel of claim 91, wherein a plane of any of said at least two boundary surfaces is approximately perpendicular to said axis of symmetry of a field of respectively adjacent electrodes.

111. The IB-channel of claim 91, wherein any of said at least two boundary surfaces comprises symmetry which corresponds to field symmetry of an adjacent IO element.

112. The IB-channel of claim 91, wherein at least one of an input surface and an output surface is located outside of a field of electrodes.

113. The IB-channel of claim 91, wherein output surfaces are superposed onto a surface of an output electrode.

114. The IB-channel of claim 91, wherein input surfaces are superposed onto a surface of an input electrode.

115. The IB-channel of claim 91, wherein said at least two boundary surfaces comprise at least two input surfaces for said channel ion flux to enter into said IB-channel, hereinafter a-surfaces, as well as at least one output surface, wherein said output surface confines a limit of channel ion flux transfer, said output surface being selected from the group consisting of output d-surfaces to detector elements of a detector system and to q-surfaces for transferring said channel ion flux into other IB-channels.

116. The IB-channel of claim 115, comprising an IO channel system of a linear type with a straight axis and comprising: a diaphragm-electrode located along a straight axis of a symmetry surface of a first group of input electrodes, a second group of electrodes, and a said output surface, wherein a front side of said output surface of output faces at least one of said input surfaces.

117. The IB-channel of claim 115, comprising an IO channel system of a reflecting type with a straight axis and comprising: a diaphragm-electrode located along a straight axis of symmetry of an input surface of a first group of electrodes, an output surface comprising a hole on said axis for said channel ion flux to path through in a forward direction, and a second group of electrodes, wherein said second group of electrodes together with said output surface, which faces said second group of electrodes, form a local reflecting IO element.

118. The IB-channel of claim 115, comprising an IO channel system of a double-mode type with a straight axis and comprising: a diaphragm-electrode located along a straight axis of symmetry of an input surface, a first group of electrodes, a first surface of output comprising a hole provided on said axis for said channel ion flux to pass through in a forward direction, a second group of electrodes, and a second surface of output, wherein a front side of said first surface of output faces an opposite direction than said input surface, while a front side of said second surface of output faces said surface of input.

119. The IB-channel of claim 115, having a straight axis of symmetry and comprising output d-surfaces which confines the limit of channel ion flux transfer to a relevant detector elements as said channel ion flux leaves said IB-channel.

120. The IB-channel of claim 119, comprising a diaphragm-electrode having a hole therein, wherein configuration of said hole is selected from a group consisting of round, oval, quadrupole, and a configuration in which a geometric center is located on said straight axis of symmetry, and wherein said diaphragm-electrode is configured to allow control of at least one of a size and a configuration of said hole.

121. The IB-channel of claim 120, configured to vary electric potential in at least one electrode and to control at least one of a cross-space dispersion value by energy and a dispersion value by mass.

122. The IB-channel of claim 91, comprising an IO channel system with a curved main axis in cross-space dispersing mode, including a management subsystem mentioned in this invention, at least one cross-space dispersing IO element selected from the group consisting of refracting conic fields, magnetic and/or nonmagnetic conic fields, prismatic conic fields, and V-shaped conic fields.

123. The IB-channel of claim 91, comprising an IO channel system configured as a management subsystem, mentioned in this invention, and configured to transfer said ion flux from a surface of input to a surface of output of said IB-channel.

124. The IB-channel of claim 91, comprising an IO channel system of single type functional in a multireflecting mode and comprising a P-multireflector, mentioned in this invention.

125. The IB-channel of claim 124, wherein a conventional end surface of said IB-channel and of said P-multireflector is an end surface of said P-multireflector onto which said ion flux enters from an ionic source block, while an opposite end surface is a conventional lower end side of said P-multireflector and of said IB-channel.

126. The IB-channel of claim 124, that comprises a management subsystem, mentioned in this invention, unified in a LS-group of transferring subsystems,
wherein each transferring subsystem comprises of SSTO—subsystem of external or internal transfer, hereinafter SSTO series, and uses at least one of the refracting, reflecting and field-free modes that features transferring the channel ion flux into the one among: reception from the entry with $W_a$—entry surface of the IB-channel and injection into the P-multireflector; cross transfer; bypath transfer; output from the P-multireflector and transfer into one of $W_{qm}$ transfer q-surfaces, arranged from the lower side end at $W_{qm}=W_{qL}$, from the upper end side at $W_{qm}=W_{qU}$ when leaving the IB-channel, and into two $W_{qm}$ transfer q-surfaces arranged from two end sides when leaving the IB-channel,
wherein $W_{qm}$ transfer q-surface are to transfer ion flux from the IB-channel into e.g. another IB-channel, and where the whole LS-group enables at least one passage of ion flux through fields generated by one-cycle P-multireflector.

127. The IB-channel of claim 126, wherein its LS-group is performed with additional option feature allowing to use it for transfer the channel ion flux from the P-multireflector, at least, into one of $W_{dm}$ output d-surfaces (arranged, at least, from one (lower) of side ends at $W_{dm}=W_{dL}$, or from the upper side end at $W_{dm}=W_{dU}$, as leaving the IB-channel), herewith the $W_{dm}$—output d-surfaces confine the limit of channel ion flux transfer to detector group arranged as appropriate.

128. The IB-channel of claim 91, comprising an IO channel system of cascade-multilayered type functional in a multireflecting mode and comprising at least two P-multireflectors, wherein each P-multireflector constitutes one junction of a $\{P_{\mu(s)}\}$ group and base planes of said P-multireflectors mentioned in this invention are arranged approximately parallel to each other, and wherein IO subsystems of said cascade-multilayered type IO channel system function in said multireflecting mode are of two categories:
cascade-single-array-multilayered type subsystems functional in a multireflecting mode comprising said P-multireflectors arranged in a single junction; and
cascade-multi-train-multijunction type subsystems functional in a multireflecting mode comprising at least two said P-multireflectors of said cascade-single-array-multilayered type and functional in said multireflecting mode.

129. The IB-channel of claim 128, wherein said at least two P-multireflectors are configured such that ones of said P-multireflectors functional in an increment mode are arranged in a single array while P-multireflectors of a planar type are arranged one above the other, wherein an input end side of said IB-channel and said $\{P_{\mu(s)}\}$-group of cascade-single-array-multilayer type functional in said multireflecting mode comprises a conventional end side onto which said ion flux enters from a side of an ionic source block, while an opposite end side is a conventional lower end side of said IB-channel and of said $\{P_{\mu(s)}\}$-group of cascade-single-array-multilayer type.

130. The IB-channel of claim 129, comprising a two-loop-wise path type having a four-mirror mode, comprising at least one unclosed layer, and configured to allow receipt of said ion flux from one adjacent layer and to transfer said ion flux backwards into at least one of said adjacent layer and another layer.

131. The IB-channel of claim 130, wherein said unclosed layer comprises an input-output of a projection-parallel symmetrically hetero-planar mode.

132. The IB-channel of claim 130, wherein said layers comprise unclosed layers with an input-output of a projection-parallel symmetrically hetero-planar mode and configured to transfer said ion flux from one layer into another.

133. The IB-channel of claim 128, wherein facing adjacent sides of layers of said $\{P_{\mu(s)}\}$-group are approximately parallel to one another and adjoin one another on at least one side, while upper output end sides of said layers facing away from each other and lower end sides facing away from each other are arranged on a single level.

134. The IB-channel of claim 128, wherein parts of at least two adjacent electrodes of two adjacent ones of said P-multireflectors associated with two adjacent layers of said $\{P_{\mu(s)}\}$-group are arranged on two sides of one substrate and are arranged symmetrically relative to said substrate.

135. IB-channel comprises a management subsystem mentioned in this invention, united in LS-group of transferring subsystems,
wherein each said transferring subsystem comprises at least one management subsystem,
wherein the transferring subsystems are performed in expanded SSTO series, where SSTO is a subsystem of external or internal transferring, as well as, in expanded SSTA series, where SSTA is a subsystem of adjacent transferring, forming the $\{A_{m(j)}\}$-subgroup, wherein the subsystems of external and internal transferring, with assistance of at least one of operation modes, mentioned in this invention (refracting, reflecting and field-off), are performed to enable transferring the channel ion flux into the one among: reception from the output, i.e. from the entry $W_a$—surface of IB-channel and then input into the $\{P_{\mu(s)}\}$-group; cross transfer; distant back transfer; bypath transfer; output from the $\{P_{\mu(s)}\}$-group and transfer to one of $W_{qm}$—transfer q-surfaces arranged from the lower end side at $W_{qm}=W_{qL}$, from the upper end side at $W_{qm}=W_{qU}$ when leaving the IB-channel, and into two $W_{qm}$—transfer q-surfaces arranged from two end sides when leaving the IB-channel, wherein the $W_{qm}$—transfer q-surfaces are to transfer ion flux from the IB-channel into, e.g. another IB-channel, wherein the whole LS-group enables at least one passage of ion flux through fields generated by $\{P_{\mu(s)}\}$-group.

136. The IB-channel of claim 135, wherein said $\{A_{m(j)}\}$-subgroup of its LS-group is performed with an additional feature of allowing said sequential passage (transferring) of ion flux through layers of $\{P_{\mu(s)}\}$-group, wherein subscripts s and j, possessing the value within the range $1 \leq s \leq c$, $1 \leq j \leq b$ and $b=c-1$, confine respectively serial numbers of $P_{\mu(s)}$—layers in the $\{P_{\mu(s)}\}$-group and $A_{m(j)}$—SSTA in the $\{A_{m(j)}\}$-subgroup given (increasing) in direction towards from the input to the output of the IB-channel, wherein: c—overall quantity of layers in the $\{P_{\mu(s)}\}$-group (equal to the number of its last layer); b—overall quantity of SSTA in $\{A_{m(j)}\}$-subgroup (equal to the number of its last SSTA); subscript m assumes two values (m=U, L) and determines the SSTA arrangement from the upper end side (upper SSTA—at m=U), or from the lower end side (lower SSTA—at m=L) of $\{P_{\mu(k)}\}$-group and IB-channel.

137. The IB-channel of claim 134, wherein said $\{P_{\mu(s)}\}$-group comprises a unilateral layer of recurring $P_{\mu(s)} \equiv P_{iVs}^{(m)}$-mode (first type at i=1 or second type at i=2 and additionally comprises a management subsystem, mentioned in this invention), wherein input and output of said ion flux are achieved only from one end side: upper end side, at (m)=(U) or from its lower end side, that is opposite to its upper end side at (m)=(L).

138. The IB-channel of claim 134, wherein said $\{P_{\mu(s)}\}$-group comprises a layer of $P_{\mu(s)} \equiv P_{Ws}$ two layer through mode, in which at least one of ion flux input and may be achieved from two end sides.

139. The IB-channel of claim 136, wherein LS-said group is configured to be used for transferring channel ion flux from said $\{P_{\mu(s)}\}$-group to at least one boundary surface of output (arranged on at least one of the lower side at $W_{dm}=W_{dL}$, the upper side at $W_{dm}=W_{dU}$, as leaving said IB-channel, wherewith said boundary surfaces of output $W_{dm}$ and $W_{dm2}$—output d-surfaces confine a limit of said channel ion flux transferring to detector elements of appropriate arrangement.

140. The IB-channel of claim 136, wherein said $\{P_{\mu(s)}\}$-group and $\{A_{m(j)}\}$-subgroup are configured to be used in one of a $(P_{\mu(n)}^{(m)} P_{\mu(n+1)}^{(m)})$-mode of transferring said channel ion flux in a forward direction to said $\{P_{\mu(s)}\}$-group and a mode of transferring said channel ion flux from one layer $P_{\mu(n)}^{(m)}$ to a following adjacent layer $P_{\mu(n+1)}^{(m)}$.

141. The IB-channel of claim 136, configured to turn-on a mode of transferring the $\{P_{\mu(a)}^{(m)} P_{\mu(b)}^{(m)}\}$ said channel ion flux from one layer to another layer preceding said one layer (a b) and a mode of remote transferring (a b+1) of said channel ion flux from a last layer of said $\{P_{\mu(s)}\}$-group into a first layer of said $\{P_{\mu(s)}\}$-group for repeated traversal through layers of said $\{P_{\mu(s)}\}$-group.

142. The IB-channel of claim 141, wherein at least one of its said SSTO and SSTA is performed with option feature to use it in retransferring mode.

143. The IB-channel of claim 141, further comprising additionally the upper SSTO, performed with option feature to use it in retransferring mode.

144. The IB-channel of claim 141, wherein, at least, one of said mentioned SSTO, SSTA and additional upper SSTO is performed with option feature allowing to retransferring, between the upper end sides of the layers of the $\{P_{\mu(s)}\}$-group.

145. The IB-channel of claim 141, configured to be used in a running multicyclic mode and comprising a $\{P_{Ws}\}$-group with even-numbered layers and the $\{A_{mj}\}$-subgroup.

146. The IB-channel of claim 128, comprising, at at least one side of an operating zone of one of said P-multireflectors one of a surface of input and a surface of output.

147. The IB-channel of claim 146, wherein said LS-group (at least one of its SSTO and SSTA) is configured to allow transferring of said channel ion flux towards said surface of output of said IB-channel from outside a surface of an ion flux section within said operating zone of said one of said P-multireflectors.

148. The IB-channel of claim 147, wherein said LS-group is configured to allow transferring of said channel ion flux between any of said surface-sections within operating zones of two of said P-multireflectors.

149. The IB-channel of claim 148, wherein said portion is configured to allow transferring of said channel ion flux between two of said P-multireflectors along projective-parallel symmetrically heteroplane directions of said channel ion flux, wherein a transferring subsystem which transfers said channel ion flux is configured as a management subsystem provided with an input-output in projective-parallel symmetrically heteroplane mode.

150. The IB-channel of claim 149, wherein said portion is configured to allow transferring of said channel ion flux by frontal components of typical lines of two P-multireflectors of two-loop-reflecting type.

151. The IB-channel of claim 149, wherein said portion is configured to allow transferring of said channel ion flux along projective-parallel diagonal segments of generic lines of two-loop-wise reflecting P-multireflectors.

152. The IB-channel of claim 148, wherein said portion is configured to allow transferring of said channel ion flux between two layers of said $\{P_{\mu(s)}\}$-group, along antiparallel, single-plane directions of said channel ion flux, wherein a transferring subsystem for transferring said channel ion flux is configured as a management subsystem of single plane mode with antiparallel input-output.

153. The IB-channel of claim 152, wherein said portion is configured to transfer said channel ion flux along frontal segments of generic lines of two-loop-wise reflecting P-multireflectors.

154. The IB-channel of claim 152, wherein said portion is configured to transfer said channel ion flux along diagonal segments of generic lines of two-loop-wise reflecting P-multireflectors.

155. The IB-channel of claim 148, wherein said portion is configured to transfer said channel ion flux within operating zones of two layers of said $\{P_{\mu(s)}\}$-group along directions of single-planes intersecting at an angle of said channel ion flux.

156. The IB-channel of claim 155, wherein a transferring subsystem for transferring said channel ion flux is configured as a management subsystem of single plane and single reflecting mode.

157. The IB-channel of claim 155, wherein a transferring subsystem for transferring said channel ion flux is configured as a management subsystem of single plane and doubly reflecting mode.

158. The IB-channel of claim 126, wherein a portion thereof is configured to equalize an ion flight time on upper and lower trajectories of said path ion flux arranged in ion packages.

159. The IB-channel of claim 91, wherein at least one electrode of at least one extended P-element of reflection is configured to supply pulsating voltage to said at least one P-element of reflection to implement at least one of ion input into said P-multireflector and ion output from said P-multireflector.

160. The IB-channel of claim 91, configured to control space focusing of ion flux along a direction of ion motion in said path ion flux.

161. The IB-channel of claim 91, wherein at least one electrode of at least one extended reflection P-element is configured to supply pulsating voltage to said at least one extended reflection P-element to control space focusing of ion flux along a direction of said path ion flux.

162. A mass-spectrometer (MS) comprising:
 (i) MS-blocks including: an ionic source block, a group of ion conducting blocks, comprising a block-structured docking group, and an analyzing-dispersing block, wherein all said blocks comprise IB-channels with boundary surfaces and IO channel systems, wherein each said IB-channel associated with one of said blocks is a part of an MS-channel with an MS-channel IO system comprising ion conducting IB-channels of ion conducting blocks in complex with an ion source IB-channel of an ion source block, and wherein said IO channel system of said ion-conducting IB-channel function as one of: a management subsystem, a subsystem with a curved main axis in a cross-space dispersing mode, a subsystem with a curved main axis, in a multi-reflecting mode,
 (ii) a detector system,
 (iii) a control-computer system;
 configured to be used at least in one of:
 channel-multipath ion flux mode with multi-cell section surfaces, and an off-axis single-path channel ion flux mode with double-cell section connected surfaces;
 comprising at least one of an IO element enabling selection of a specified spatial orientation of said IO element relative to at least one other IO element and relative to a direction of an averaged vector of said ion flux entering said IO element, a flat unary P-multireflector, a three-dimensional P-multireflector, a cascade-multilayered multireflector, an extended P-element of refraction, a three-dimensional P-element of reflection, a P-element of non-uniform height, and a P-element of reflection with a two-dimensional reflection zone.

163. The MS of claim 162, wherein said block-structured docking group comprising at least a preshaping block and a distributing-accelerating block group.

164. The MS of claim 163, wherein said MS-block comprises at least one IB channel configured in a mode selected from a group consisting of: channel-single-path mode, and channel multipath mode and wherein at least one MS-channel is configured to allow said path ion flux to pass from said ions source to at least one d-surface defining a limit of channel ion flux transfer with respect to a detector element of said detector system.

165. The MS of claim 164, wherein at least one of its ion-conducting IB-channels is decided-on among the series mentioned in this invention.

166. The MS of claim 162, wherein each said path ion flux corresponds to one individual detector in a detecting element of said detector system.

167. The MS of claim 162, wherein when configured in channel multipath mode, said ion paths are configured to be used in at least one mode of independently of one another and alternatively in a specified time frame.

168. The MS of claim 162, configured in channel multipath modes, wherein each pair of said IB-channels in each said block is configured as at least one of a bound pair and a separate pair.

169. The MS of claim 162, wherein, when configured in multichannel mode, said ion channels are configured to be used in at least one mode of independently of one another and in a specified time frame.

170. The MS of claim 162, wherein each said output gate of said surface-electrode of a preceding said IB-channel is an output gate of a subsequent said IB-channel.

171. The MS of claim 170, wherein a reverse side of an output electrode surface of said preceding IB-channel is an input electrode surface of a next nearest IB-channel.

172. The MS of claim 162, configured in module-block-structured mode and configured to allow a simplified arrangement of modular equipment and reconfiguration of block patterns of said MS thereby providing a wide variety of modularity limits and resolution powers.

173. The MS of claim 162, wherein said ionic source IB-channel, mentioned in this invention, comprises at least one ion source each said ion source being adjacent to one output aperture of said ionic source, selected from the group consisting of: holes; screening tubes with skimmers; screening tubes without skimmers; and devices for preliminary forming of at least one path ion flux, wherein quantity number, configuration, and arrangement of holes of said devices conform to boundary surfaces.

174. The MS of claim 173, wherein said ionic source IB-channel additionally comprises a transient controlling source unit comprising at least one electrode with output surfaces for transferring said path ion flux.

175. The MS of claim 174, wherein the ions source of ionic source IB-channel is decided-on among the series comprising any ionic source providing forming of ion flux, e.g., electronic ionization (EI), chemical ionization (CI), electron capture (EC), electric field ionization (FI), ionization with heat spray, ionization under atmospheric pressure, electrospray, ionization under atmospheric pressure (APESI), chemical ionization under atmospheric pressure (APCI), photoionization under atmospheric pressure (APPI), inward laser desorption: mass-spectrometry, matrix-activated laser desorption/ionization (MALDI), gas-filled MALDI, atmospheric MALDI, bombardment by fast atoms (FAB), field desorption—desorption in electric field (FD, plasma desorption (PD), ionization in inductively coupled plasma (ICP), thermal ionization, glow discharge ionization and spark ionization, plasma and glow discharge ionization, corona discharge and ionization in process of laser ablation.

176. The MS of claim 173, wherein said ionic source IB-channel is configured to allow forming of ion flow exiting said ionic source IB-channel in at least one of a pulsed flow of ions packages and a continuous ion flow.

177. The MS of claim 176, wherein said block-structured docking group comprises a block-structured docking group adjacent said ionic source block comprising at least one parallel pre-shaping IB-channel, which pre-shaping IB-channel comprises at least one structural elements configured to allow intermediate configuration, acceleration, and control of ion flux forming.

178. The MS of claim 177, wherein said pre-shaping IB-channel comprises at least one section selected from a group consisting of: ion pre-traps; flux drift tubes of asymmetrical cells of ion mobility, DC/field comprising input and output gates with ion gate valves; refracting P-elements; and diaphragms-apertures.

179. The MS of claim 178, wherein said ion pre-trap is configured to:
select certain quantities of ions generated by said ionic source IB-channel;
to store said quantities of ions; and
to output said store ions from said ion pre-trap and input said stored ions into at least one subsequent said MS block.

180. The MS of claim 179, wherein said ion pre-trap is selected from a group consisting of a controlling electrode group with an electric field, a short unit of guiding quadrupole, and a diaphragm-aperture.

181. The MS of claim 180, wherein said block-structured docking group additionally comprises a distributing-accelerating block arranged behind a performing block which comprises at least one distributing-accelerating IB-channel, wherein one of said distributing-accelerating block and said distributing-accelerating IB-channel comprises at least one pre-analyzing-guiding accelerator configured to allow guiding of said ion flux towards an analyzing-dispersing IB-channel which comprises at least two accelerating electrodes with at least, one output gate.

182. The MS of claim 181, wherein said at least one output gate of said pre-analyzing-guiding accelerator is covered with a fine mesh.

183. The MS of claim 181, configured to confine an angle $\beta_{(12)1}$ defined between output directions of said ion flux from the said ionic source IB-channel and from said pre-analyzing-guiding accelerator within the range of $$0 \leq \beta_{(12)1} \leq \frac{\pi}{2},$$

and wherein said pre-analyzing-guiding accelerator is arranged radially with radial ion output when $\beta_{(12)1} \approx 0$ and is arranged orthogonally when $$\beta_{(12)1} \approx \frac{\pi}{2}.$$

184. The MS of claim 183, wherein said distributing-accelerating IB-channel is configured to form a pulse ion flux as said ion flux passes through said pre-analyzing-guiding accelerator.

185. The MS of claim 183, wherein said distributing-accelerating IB-channel comprises two segments, wherein one of said two segments is configured to use an alternating voltage while another of said two segments is configured to use a static voltage.

186. The MS of claim 183, wherein said distributing-accelerating IB-channel is configured to form thin ions packages appropriate for time-of-flight mass-analysis of said ion flux as said ion flux passes through said pre-analyzing-guiding accelerator.

187. The MS of claim 186, wherein its distributing-accelerating IB-channel is performed with option feature allowing an orthogonal ions output $$\left(\text{at } \beta_{(12)1} \approx \frac{\pi}{2}\right)$$

its accumulation area is performed as a monofield generating a quadratic electrostatic field, while the edge of earthed electrode of the said monofield is coupled to the earthed fluxgate electrode (mesh) within the area of ions acceleration (palser) with uniform field.

188. The MS of claim 181, wherein said distributing-accelerating IB-channels are configured as static and are configured to allow forming of a continuous ion flux as said ion flux is output from said pre-analyzing-guiding accelerator.

189. The MS of claim 181, wherein said distributing-accelerating IB-channel additionally comprises a pre-analyzing ions accumulator, arranged ahead of said pre-analyzing guiding accelerator and serially connected to said pre-analyzing guiding accelerator, where said pre-analyzing ion accumulator is configured to allow receipt, accumulation, and intermittent emission of said ions in at least one of radial, axial, and orthogonal directions through said apertures.

190. The MS of claim 189, wherein said pre-analyzing ion accumulator is selected from a group consisting of a linear RF-only IC and a curved quadrupole.

191. The MS of claim 173, wherein its detector group comprises one or more ions detector with entrance gate arranged on the entry d-surface, where each path ion flux corresponds, to an individual ion detector of detector element decided-on among the terms series comprising: Faraday cylinder; secondary electron multiplier with at least one dynode; scintillator and photomultiplier; microchannel; microsphere board; at least two slots of detection; at least two anodes.

192. The MS of claim 191, wherein, at least, one ions detector of detecting group is provided with ions separator of certain transmission band and comprises, at least, one of series terms comprising control grids, logical Bradbury-Nielsen terms, plane-parallel deflector (condenser).

193. The MS of claim 191, wherein each ions detector is connected to the system of data acquisition and data-storage provided with analog-to-digital converter (adaptive data compression protocol).

194. The MS of claim 191, wherein at least one ion detector is configured within said MS.

195. The MS of claim 194, wherein said ion detector is configured to allow extension of a dynamic range of said MS through alternative scanning associated with varied intensity of voltage of at least one of a pulsating ionic source and said distributing-accelerating IB-channel.

196. The MS of claim 194, wherein said ion detector is configured to extend a dynamic range of said MS through alternative scanning in varying durations of ion injections into an output gate of said ion source.

197. The MS of claim 194, wherein said ion detector is configured to allow automatic gain control.

198. The MS of claim 181, wherein its analyzing-dispersing block comprises at least, one analyzing-dispersing IB-channel, decided-on among the series comprising the following: toroidal and cylindrical sectoral electrical analyzers; sectoral magnetic analyzers; orbitrap analyzer; Fourier analyzer ICR; static analyzer, e.g., the IO channel system of IB-channel is performed with curved main axis in cross-space dispersing mode, mentioned in this invention; the time-of-flight (TOF IB-channel) analyzer and its IO channel system are performed in one of said modes, mentioned in this invention.

199. The MS of claim 181, further comprising a detecting group arranged on at least side adjacent said analyzing-dispersing IB-channel, wherein said detecting group comprising multiple ion detectors of different types, mentioned in this invention.

200. The MS of claim 198, wherein its block-structured docking group additionally includes an block of fragmentation cell comprising at least, one IB-channel of fragmentation cell-set filled with gas and provided with differential pumping cascades wherein each fragmentation cell is provided at least, with two apertures to access the path ion flux into the fragmentation cell and to exit from it.

201. The MS of claim 200, wherein each its path ion flux corresponds to one individual fragmentation cell (section of fragmentation cells).

202. The MS of claim 201, wherein at least one fragmentation cell is performed with option feature to using it in two modes: passage of ions through fragmentation cell without substantial atomization or with ions atomization (fragmentation) within fragmentation cell (inside of fragmentation cell).

203. The MS of claim 199, wherein said block-structured docking group additionally includes one ion selecting block comprising at least one IB-channel of ion selection, configured to allow sequential reduction of the range of ion mass selection through at least one ion selecting step.

204. The MS of claim 203, wherein said IB-channel of ion selection is selected from a group consisting of: a quadrupole IB-channel; an ion trap; a static IB-channel; and a TOF IB-channel analyzer.

205. The MS of claim 203, comprising a detecting group arranged at least on one side of said IB-channel of ion selection.

206. The MS of claim 203, wherein at least one of said analyzing-dispersing IB-channels and said IB-channel of ion selection comprises means of adjusting a path length and a voltage of ion acceleration.

207. The MS of claim 206, wherein said analyzing-dispersing IB-channel is configured to allow at least one of said ion path length and said voltage to be less than a value for said IB-channel of ion selection.

208. The MS of claim 207, wherein said MS-channel is configured to allow ion time-of-flight through said IB-channel of ion selection to be at least three times as large as ion time-of-flight through said analyzing-dispersing IB-channel.

209. The MS of claim 208, wherein at least one of said IB-channel of ion selection and said analyzing-dispersing IB-channel is nonmagnetic.

210. The MS of claim 208, wherein said IB-channel of ion selection is configured as a time-of-flight IB-channel and said IO channel system is configured in multireflecting mode and selected from the group consisting of: single, single-train-multilayer and multi-row-multilayer modes.

211. The MS of claim 210, wherein said analyzing-dispersing IB-channel mentioned in this invention is configured as a time-of-flight IB-channel with straight axes.

212. The MS of claim 205, wherein said block-structured docking group additionally comprises blocks of additional ion accumulation, comprising at least one IB-channel of additional ions accumulation, configured to allow selection of the ion subsets or at least some of their derivatives.

213. The MS of claim 212, wherein said IB-channel of additional ion accumulation is selected from the group consisting of linear RF-only IC and curved quadrupole.

214. The MS of claim 212, wherein at least one said MS-channel is configured to allow implementation of a series of steps towards for ion flux:
(ab) inject said path ion flux via an IB-channel of said ionic source into a pre-shaping IB-channel;
(bc) eject said path ion flux from said pre-shaping IB-channel and inject said path ion flux into a distributing-accelerating IB-channel;
(cd) eject said path ion flux from said distributing-accelerating IB-channel, inject said path ion flux into said ion selecting IB-channel, and register said path ion flux in at least one detector group at said ion selecting IB-channel;
(de) eject said path ion flux from said ion selecting IB-channel and inject it into a fragmentation cell;
select from the series comprising {(ec) and (ef)}: eject the path ion flux from the cell of fragmentation and inject it depending on the path ion flux composition after the effect of the cell of fragmentation on the ion flux at appropriate option into one of channels: distributing-accelerating IB-channel; IB-channel of additional ion accumulation and storage of taken-off ions masses;
(Q11) at least, one cycle comprising series steps such as (cd), (de) and {(ec) or (ef)} to accumulate ions of specified masses in the IB-channel of additional ion accumulation;
select from the series comprising (fc) and {(fe) and further (ec)}: (fc)-eject the path ion flux from the IB-channel of additional ion accumulation and inject it into the distributing-accelerating IB-channel; {(fe)}: eject the path ion flux from the IB-channel of additional ion accumulation and inject it into cell of fragmentation; and further {(ec)}: eject the path ion flux from the cell of fragmentation and inject it into distributing-accelerating IB-channel;
(Q12) at least, one cycle comprising (Q11) with subsequent selection from (fc) and {(fe) and further (ec)};
(cg) eject the path ion flux from the distributing-accelerating IB-channel and inject it into the analyzing-dispersing IB-channel, as well register the path ion flux at least in one detector group of analyzing-dispersing IB-channel;
at the option, depending on results of step (cg) realization, implement the steps of channel ion flux transfer by means of two of groups of steps: (Q13), at least, one cycle comprising single-stepping implementation of all steps of path ion flux advance as it is specified in (ab)-(cg) mentioned in this claim; select from the series comprising (ge), {(gc) and further (ce)}: eject the path ion flux from the analyzing-dispersing IB-channel and inject it, conforming to appropriate option, into one of channels: into the fragmentation cells; {(eject the path ion flux from the analyzing-dispersing IB-channel inject it into the distributing-accelerating IB-channel) and further (eject the path ion flux from the distributing-accelerating IB-channel and inject it into fragmentation cells)};
(Q14) at least, one cycle comprising implementation of all steps: beginning by the step selected from the group consisting of {(ec), (ef)} and finishing by (cg) step as it is specified in this claim.

215. The MS of claim 212, wherein at least one MS-channel is performed with option feature allowing sequential steps to transferring channel ion flux (second version of extended-multiblock mode):
- (ab); (bc); (cd); (de);
- decided-on among the group of {(ec), (ef)};
- (Q11);
- decided-on among the group of (fc) and {(fe and further (ec)};
- (cg);
  - at the option, depending on results of step (cg) realization implement the steps of channel ion flux transfer by means of one of two groups of steps: (Q23) at least, one cycle comprising sequential implementation of all steps (ab)-(cg) as said in this claim; selection from the series comprising (ge) and {(gc) and further (ce)};
- (Q24) at least, one cycles comprising sequential implementation of all steps: beginning from decided-on among the group of {(ec) or (ef)} to (cg) as said in this claim.

216. The MS of claim 211, wherein at least one MS-channel is performed with option feature allowing sequential steps in transferring channel ion flux by skipping the IB-channel of additional ion accumulation (multiblock mode of operation):
- (ab); (bc); (cd); (de); (ec);
- (Q31) at least, one cycle comprising increments as steps follows: (cd), (de) and (ec);
- step (cg);
  - at the option, depending on results of step (cg) realization implement the steps of channel ion flux transfer by means of one of two groups of steps: (Q33) at least, one cycle comprising sequential implementation of all steps (ab)-(cg) as said in this claim; select from the series comprising (ge) and {(gc) and further (ce)};
- (Q34) at least, one cycle comprising sequential implementation of all steps beginning from (ec) to (cg) as it is specified in this claim.

217. The MS of claim 200, wherein at least, one MS-channel is performed with option features allowing to implement series steps of path ion flux advance by-passing the IB-channel of additional ion accumulation and IB-channel of ions selecting, failing all last mentioned IB-channel inclusive (mean modularity level of operation without ions selecting):
- (ab); (bc); (cg); (ge) or {(gc) and further (ce)}; (ec); (cg);
  - at the option, perform the series steps of path ion flux advance depending on results of (cg) step implementation:
    - at the option, depending on results of step (cg) completion implement the steps of channel ion flux transfer by means of one of two (Q43), (Q44) groups of steps:
- (Q43) at least, one cycle comprising implementation of all steps beginning from (ab) to the last (cg) step mentioned in this claim;
- (Q44) at least, one cycle comprising implementation of all steps (ec); (cg) decided-on among the group of (ge) and {(gc) and further (ce)} mentioned in this claim.

218. The MS of claim 199, wherein at least one MS-channel is performed with option feature allowing a sequential implementation of all steps to transferring the channel ion flux by-passing the IB-channels of additional ion accumulation and the IB-channel of fragmentation cell, failing all last mentioned IB-channels inclusive (mean modularity level of operation without ions fragmentation):
- (ab); (bc); (cd);
- (dc) output the channel ion flux from the ions selecting IB-channel and input it into distributing-accelerating IB-channel;
- (Q51) at least, one cycle comprising implementation of all steps (cd) and (dc);
- step (cg).

219. The MS of claim 199, wherein at least one MS-channel is performed with option feature allowing sequential implementation of all steps to transferring the channel ion flux by-passing the IB-channel of additional ion accumulation, IB-channel of ions selecting and IB-channel of fragmentation cell, failing all last mentioned IB-channels inclusive (small modularity regime of operation): (ab); (bc); (cg).

220. The MS of claim 162, wherein when it is performed as a time-of-flight analyzing-dispersing IB-channel it comprises a data transmitting and data processing system providing parallel reception of child fragments spectra without intermixing the ions spectra representing the primary materials.

* * * * *